(12) United States Patent
Kotman et al.

(10) Patent No.: US 9,886,245 B2
(45) Date of Patent: Feb. 6, 2018

(54) SOFTWARE DEVELOPMENT TOOL USING A WORKFLOW PATTERN THAT DESCRIBES SOFTWARE APPLICATIONS

(71) Applicant: Helix Data Solutions LLC, Hixson, TN (US)

(72) Inventors: Peter Kotman, Byron Center, MI (US); Jeffrey Holst, Hixson, TN (US)

(73) Assignee: Helix Data Solutions LLC, Hixson, TN (US)

( * ) Notice: Subject to any disclaimer, the term of this patent is extended or adjusted under 35 U.S.C. 154(b) by 178 days.

(21) Appl. No.: 15/052,473

(22) Filed: Feb. 24, 2016

(65) Prior Publication Data

US 2017/0242667 A1    Aug. 24, 2017

(51) Int. Cl.
*G06F 9/44* (2006.01)
*G06F 19/18* (2011.01)
*G06F 19/28* (2011.01)

(52) U.S. Cl.
CPC .............. *G06F 8/35* (2013.01); *G06F 8/20* (2013.01); *G06F 19/18* (2013.01); *G06F 19/28* (2013.01)

(58) Field of Classification Search
CPC .............. G06F 8/20; G06F 8/35; G06F 19/18
USPC .......................................................... 717/104
See application file for complete search history.

(56) References Cited

U.S. PATENT DOCUMENTS

| 4,949,253 A | 8/1990 | Chigira et al. |
| 5,287,449 A | 2/1994 | Kojima |
| 5,381,548 A | 1/1995 | Matsuo |
| 6,216,098 B1 * | 4/2001 | Clancey ................. G06Q 10/10 703/6 |
| 6,912,719 B2 | 6/2005 | Elderon et al. |
| 6,964,053 B2 | 11/2005 | Ho et al. |

(Continued)

FOREIGN PATENT DOCUMENTS

| EP | 0320818 A2 | 6/1989 |
| EP | 0315172 A2 | 7/1995 |

OTHER PUBLICATIONS

Proceedings of the Second International Conference on Multiagent Systems: Organic Programming Language GAEA for Multi-Agents—Hideyuki Nakashima, Itsuki Noda, and Kenichi Handa; Cooperative Architecture Project Team ETL; Tsukuba, Japan AAAI 1996—ICMAS-96.*

(Continued)

*Primary Examiner* — Francisco Aponte
(74) *Attorney, Agent, or Firm* — LeonardPatel PC

(57) ABSTRACT

A software development tool uses a workflow pattern that describes software applications. The tool may provide a solution that can automatically generate a well-architected application without compromising its quality or integrity. The tool may have a Data Notation Architecture (DNA) layer and a Resolution Notation Architecture (RNA) layer Genetic Framework that use a workflow pattern that describes software applications. Models may be identified and linked together using a Polymorphic Relational Path Language (PRPL), which is a scripting language that is designed and optimized to resolve various hierarchy and set theory problems that naturally appear in programming. When targeting the Service Area Architecture Pattern (SAAP), this Genetic Framework may greatly reduce the overall cost of virtually every part of the software development lifecycle.

34 Claims, 53 Drawing Sheets

(56) References Cited

U.S. PATENT DOCUMENTS

| | | | |
|---|---|---|---|
| 6,973,639 B2 | 12/2005 | Hashimoto et al. | |
| 7,114,147 B2* | 9/2006 | Ballantyne | G06F 8/76 |
| | | | 707/E17.117 |
| 7,167,844 B1 | 1/2007 | Leong et al. | |
| 7,454,413 B2 | 11/2008 | Lakshminarayanan et al. | |
| 7,467,157 B1 | 12/2008 | Chen et al. | |
| 7,603,388 B2 | 10/2009 | Wood et al. | |
| 8,438,295 B2 | 5/2013 | Shukla et al. | |
| 8,490,052 B2 | 7/2013 | Shukla et al. | |
| 8,631,387 B2* | 1/2014 | Henderson | G06F 8/24 |
| | | | 717/108 |
| 8,707,254 B2* | 4/2014 | Oslake | G06F 8/30 |
| | | | 717/106 |
| 8,726,285 B2* | 5/2014 | Leonelli | G06Q 10/06 |
| | | | 718/102 |
| 9,342,557 B2* | 5/2016 | Kornacker | G06F 17/30442 |
| 9,727,560 B2* | 8/2017 | Chakerian | G06F 17/30011 |
| 2001/0029604 A1 | 10/2001 | Dreyband et al. | |
| 2001/0044932 A1 | 11/2001 | Hashimoto et al. | |
| 2002/0199168 A1 | 12/2002 | Namito | |
| 2003/0069871 A1* | 4/2003 | Yucel | G06F 8/10 |
| | | | 706/60 |
| 2003/0070159 A1 | 4/2003 | Webb | |
| 2003/0163585 A1 | 8/2003 | Elderon et al. | |
| 2004/0046789 A1 | 3/2004 | Inanoria | |
| 2004/0111464 A1 | 6/2004 | Ho et al. | |
| 2005/0289138 A1 | 12/2005 | Cheng et al. | |
| 2006/0236254 A1 | 10/2006 | Mateescu et al. | |
| 2007/0043702 A1 | 2/2007 | Lakshminarayanan et al. | |
| 2007/0261025 A1* | 11/2007 | Seto | G06F 8/20 |
| | | | 717/108 |
| 2008/0027966 A1* | 1/2008 | Parees | G06F 17/30292 |
| 2008/0270979 A1* | 10/2008 | McCool | G06F 8/36 |
| | | | 717/108 |
| 2008/0288950 A1* | 11/2008 | Hammer | G06F 9/5066 |
| | | | 718/104 |
| 2009/0007066 A1* | 1/2009 | Grechanik | G06F 8/72 |
| | | | 717/111 |
| 2009/0164413 A1* | 6/2009 | Polat | G06F 17/30917 |
| 2010/0094926 A1 | 4/2010 | Shukla et al. | |
| 2010/0095272 A1 | 4/2010 | Shukla et al. | |
| 2010/0153933 A1 | 6/2010 | Bohlmann et al. | |
| 2012/0191716 A1 | 7/2012 | Omoigui | |
| 2012/0266131 A1 | 10/2012 | Nojiri et al. | |
| 2013/0125091 A1 | 5/2013 | Hashimoto et al. | |
| 2013/0346982 A1 | 12/2013 | Kalai et al. | |
| 2014/0149961 A1 | 5/2014 | Falk et al. | |
| 2015/0020043 A1 | 1/2015 | Ravindran et al. | |
| 2015/0058627 A1* | 2/2015 | Paffel | G06F 19/322 |
| | | | 713/168 |
| 2016/0246784 A1* | 8/2016 | Chakerian | G06F 17/30011 |
| 2017/0109347 A1* | 4/2017 | Barad | G06F 17/3007 |
| 2017/0132197 A1* | 5/2017 | Balasubramanian | G06F 17/212 |
| 2017/0270197 A1* | 9/2017 | Miracolo | G06F 17/30011 |

OTHER PUBLICATIONS

IBM-developerWorks—Model-driven and pattern-based development using Rational Software Architect: Part 1. Overview of the model-driven development paradigm with patterns; Colin Yu—Nov. 21, 2006.*

Design pattern driven development of embedded applications; Krisztián Holman, Zoltán Szabó-Budapest University of Technology and Economics, Budapest, Hungary. SAMI 2015 o IEEE 13th International Symposium on Applied Machine Intelligence and Informatics o Jan. 22-24, 2015.*

"A Tree Structure that Maps Inheritance Hierarchies of Classes," http://www.java2s.com/Tutorial/Java/0125__Reflection/Atreestructurethatmapsinheritancehierarchiesofclasses.htm (last accessed Feb. 24, 2016).

"ASP.NET MVC Overview," https://msdn.microsoft.com/en-us/library/dc1381412%28v=vs.108%29.aspx (last accessed Oct. 5, 2015).

"Build Cloud Applications without Hand-Coding," Iron Speed Whitepaper, http://www.ironspeed.com/pdf/Build-and-Deploy-Database-Applications-Without-Programming.pdf (Mar. 2010; last accessed Oct. 5, 2015).

A. Jain, "A Complete Guide to Descriptive Programming in QTP (UFT)," http://www.learnqtp.com/descriptive-programming-simplified/ (Jul. 8, 2014; last accessed Feb. 24, 2016).

Dyreson et al., "Morph: A (Shape) Polymorphic XML Query Language," http://db.ucsd.edu/planx2009/camera-ready/unpaginated/13.pdf (2009; last accessed Oct. 2, 2015).

Meijer et al., "Overview of Visual Basic 9.0," Visual Studio 2005, (Feb. 2007; last accessed Oct. 5, 2015).

R. Alur, "Marrying Words with Trees," https://www.cis.upenn.edu/~alur/Pods07.pdf (2007; last accessed Oct. 5, 2015).

Wieser, "Toward Extending Stylesheet Languages with Dynamic Document Rendering Features," http://www.en.pms.ifi.lmu.de/publications/projektarbeiten/Christoph.Wieser/fopra.pdf (Aug. 12, 2005; last accessed Feb. 24, 2016).

XML Path Language (XPath) 3.0 W3C Recomendation, http://www.w3.org/TR/xpath-30/ (Apr. 8, 2014; last accessed Oct. 2, 2015).

Yun et al., "Dynamic Interval-based Labeling Scheme for Efficient XML Query and Update Processing," http://islab.kaist.ac.krichungcw/paper.pdf (2008; last accessed Oct. 5, 2015).

* cited by examiner

FIG. 6
Write
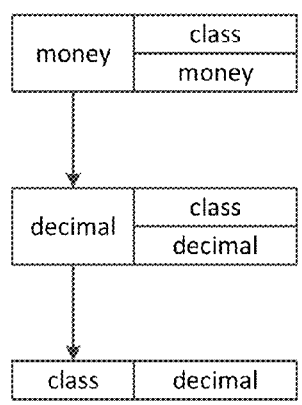
Prewrite
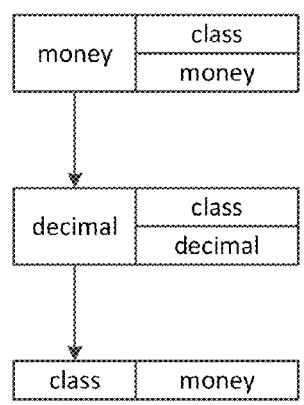
Overwrite
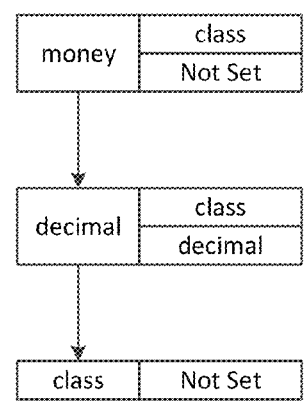
Append
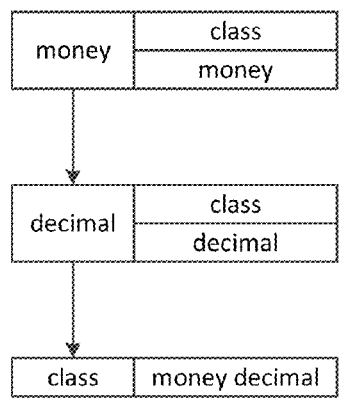
Prepend
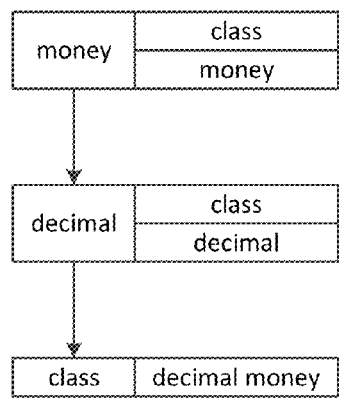

United States~Michigan~Holland/Park~Beach

United States~Michigan~Holland / Park~Beach
         Stem                      Name
              Route

1310  FIG. 13B

Shorthand: United States~Michigan~Holland/Park~Beach [Parent]
                         Reference                     Pattern

Explicit: [Query: United States~Michigan~Holland/Park~Beach,
              Pattern: Parent]

FIG. 16
1600
 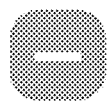  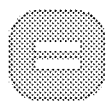
Union  Minus  Intersect  Is Equal To
  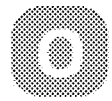 
Extend (Right)  Extend (Left)  Operator  Is Not Equal To
  
Difference  Assigns To

1800

FIG. 24
2400
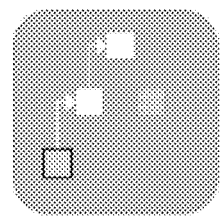
Ancestors + Self
Alpha ~ Beta ~ Gamma
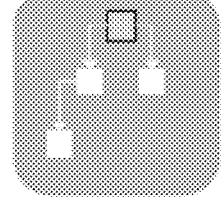
Descendants + Self
Alpha
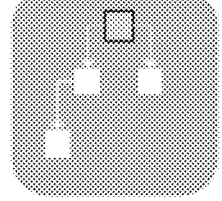
Descendants + Self
Beta
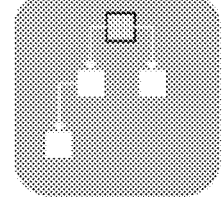
Descendants + Self
Gamma
Worst ← → Best PRPL Node Attribute Composition

PRPL Node Attribute Criteria Composition

| | {Name} | {Value} | {Is Match} | {Match Group} |
|---|---|---|---|---|
| ☐ | Parent~@Is* | True | True | * |
| ☐ | Self~Text | *Favorite* | False | * |
| ☐ | Parent~Name | Dad | True | ParentNameGroup |
| ☐ | Parent~Name | Mom | True | ParentNameGroup |
| ☐ | Self~Prpl-* | * | True | EitherOrNotGroup |
| ☐ | Next~NodeName | *null* | False | EitherOrNotGroup |

3100

Method Adapters

3200

FIG. 37
3700
Class A
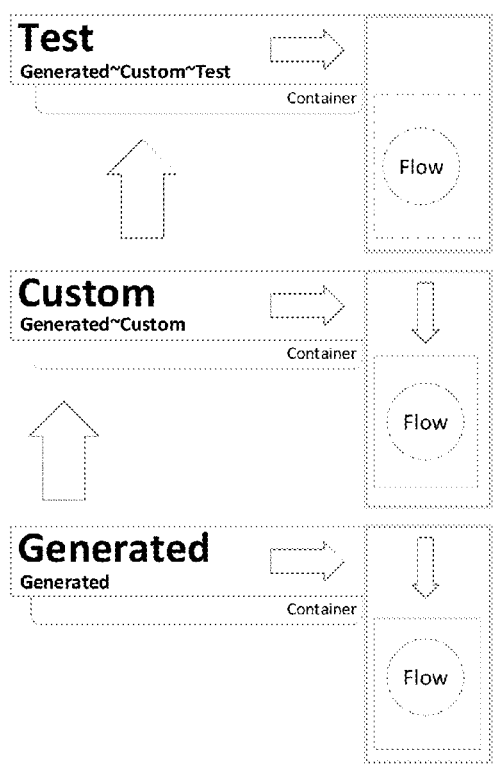
Class B
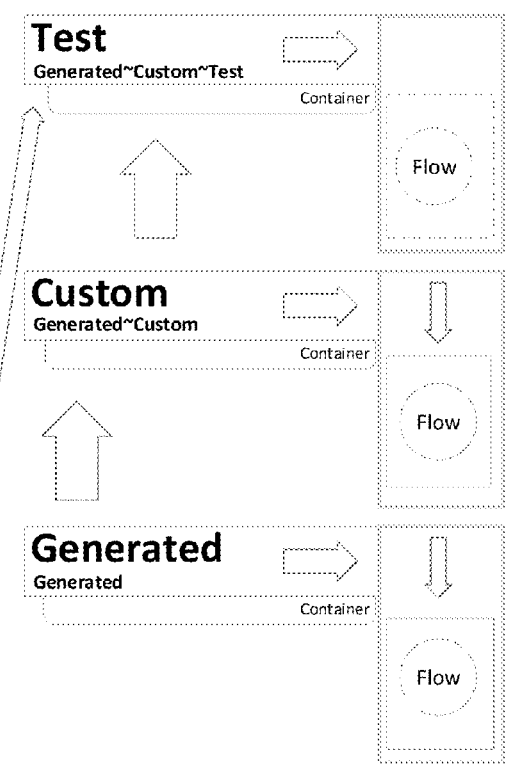

4100

FIG. 43
Dynamic Operator Flow Patterns
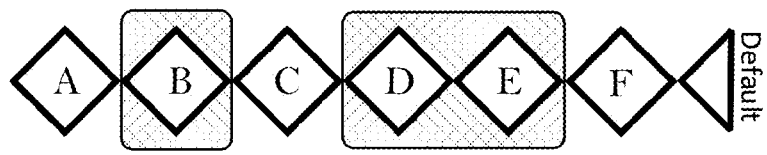
All
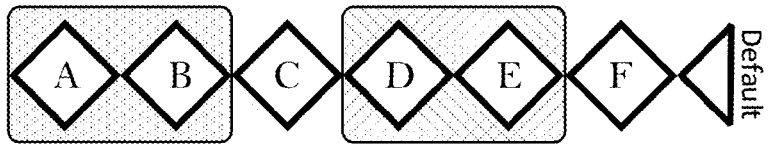
First Group
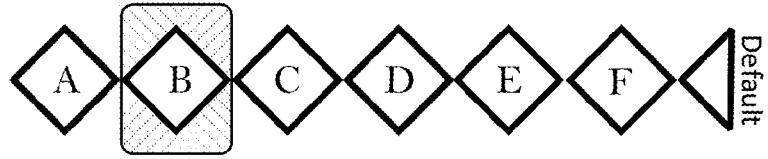
First
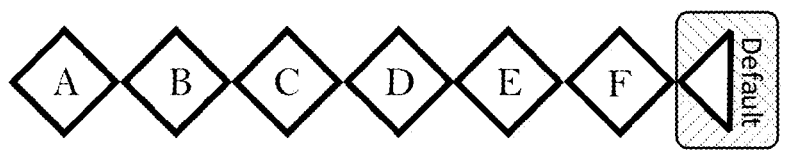
Default Fallback

SOFTWARE DEVELOPMENT TOOL USING A WORKFLOW PATTERN THAT DESCRIBES SOFTWARE APPLICATIONS

FIELD

The present invention generally relates to software development, and more particularly, to a software development tool that uses a workflow pattern that describes software applications.

BACKGROUND

When MS-DOS™ and UNIX™ were developed, utility programs were small and focused in order to manage the tasks of a computer. Computing power was limited compared to modern systems, so software applications were also limited accordingly in complexity and functionality. The utility programs could be combined together to collectively perform somewhat more complex limited tasks that such relatively primitive computers were capable of.

With the advent of visual programming and the web, applications grew in structure, functionality, and complexity. As computing power also increased, software development projects grew in an attempt to solve larger problems. Accordingly, applications were harder to develop and maintain in direct relationship to the size and complexity of the application. The architecture often appeared to resemble that of an old fashioned vacuum tube radio, with wires going everywhere. The general parts were present to carry out the various tasks, but growth necessitated more structure.

As technological progress continues to be made, software solutions are much more sophisticated (at least from an academic standpoint), with well-defined types. Attempts have been made to provide better organization. For instance, in the model-view-view model (MVVM) paradigm, view models, interfaces, and types are grouped together in an attempt to better organize the structures, which was recognized as a best practice in software development. The browser display is driven by the markup (i.e., Hypertext Markup Language (HTML)), which is affected by the JavaScript, which communicates with the web server, whose requests are trafficked through the controller, which calls the corresponding servers, which maps its data from a view model to a model, which is sent to the repository, which communicates with the database. Conversely, the database will respond to the repository, the repository will respond to service, the service will map the models back to the view models, the view model will be sent back to the controller, the controller will respond to the client request, and the JavaScript will read the message and update the model. This process can be seen in more detail in flow diagram 100 of FIG. 1.

Not all actions require this specific structure. Different actions have varying levels of complexity. While there have been some areas of increased efficiency, this is generally on the peripheral edges of software development, and the bulk of the workload still remains.

Manual programming of software tends to be verbose and redundant. Typically, it takes many lines of code for a software developer to describe tasks, and each line of code a developer writes introduces the possibility of errors. Furthermore, generally speaking, the more lines of code that are required, the more programming time that is required; the more programming time that is required, the larger the team that is required; the larger the team that is required, the more oversite that is required. Oversite often comes in the form of coding standards, code reviews, and increased testing. Budget overruns are a major problem in the industry. In short, programming large applications is complex, time-intensive, and expensive.

Projects that may take weeks to describe in requirements may take in excess of a year to implement with a team of developers. The code will vary drastically from one developer to another, despite attempts to adhere to coding standards, which come at great expense. The application needs to be tested extensively and many bugs must be resolved. Finally, after the application has been released, the costs of maintaining or extending the application remain high. Adding a single field to an existing table can take one day or more for a developer familiar with that project. Bringing new developers up to speed often takes months. Moreover, much reverse engineering of a website has to be performed by a skilled developer as knowledge is lost. Even more exasperating, these problems are not limited to the web, but exist almost everywhere in software development today.

In order to attempt to reduce the amount of time required for developing software applications, programs that automatically generate at least some of the code have been developed. However, current applications that automatically generate code still typically require many manual interrelations and rigid templating. Furthermore, code generation is not an answer to software development problems in and of itself. Rather, automatic code generation needs to be done in an appropriate manner in order to be effective.

Conventional development frameworks generally create monolithic, illegible, and rigid code that often has limited scope and breadth. For instance, the Microsoft™ Entity Framework does not provide any support for business rules that are outside of the data layer. Moreover, a large set of specialty knowledge must be maintained. Overriding or extending the generated code from conventional frameworks is problematic, and often impractical. Furthermore, conventional code generation tools have proven to be notoriously troublesome with respect to team integration.

Some end-to-end tools, such as Microsoft Access™, simplify the development of software applications, even for non-software developers. However, this ease of use often comes with a myriad of problems. These problems include limits on the number of users, security limitations, performance issues, and limits as to how software can be extended.

Accordingly, an improved software development tool and approach may be beneficial.

SUMMARY

Certain embodiments of the present invention may provide solutions to the problems and needs in the art that have not yet been fully identified, appreciated, or solved by conventional software development technologies. For example, some embodiments pertain to a software development tool that uses a workflow pattern that describes software applications. Such embodiments may provide a solution that can automatically generate a well-architected application without compromising its quality or integrity. In certain embodiments, a single software architect may describe the problem to be solved once and have the computing system write the application, as opposed to managing a team manually writing tomes of code. In such embodiments, more effort may be put into writing good code rather than testing bad code. Large scale projects that conventionally require an army of developers may be performed by a much smaller team in a fraction of the time, while yielding better results. Each business component of the application may be designed as a small and focused application.

The toolset and methodology of some embodiments may allow developers to quickly deliver software applications that have exceptional performance in areas including, but not limited to:

Integration: integrating the application with other applications may be made easier. The mundane aspects present in almost all software applications can be expressed in a much smaller space.

Performance: the generated portions of the software application can be constructed to make use of asynchronous method calls and other advanced techniques. The use of these methodologies should be relatively simple to apply to the various facets of a given application.

Maintainability: the code may be easier to trace through, sidestepping some of the pitfalls of other modern programming techniques. Applications using this framework will tend to be easier to upgrade and have lower costs of technical debt.

Testability: abstracting the bulk of the predictable code tasks should reduce the number of tests required to be written. Due to how the system components are to be architected, there should be a clearly defined space to manage tests.

Reliability: less code written manually means fewer manually created bugs. The framework of some embodiments will systematically manage the predictable coding tasks.

Scalability: code should be easier to prototype, design, and implement changes in for vertical and horizontal scalability.

Customizability: there are clearly defined spaces in some embodiments to reduce the costs developing code alterations.

Quality: the overall architecture should build upon or extend current best practices for software development.

User Experience: some embodiments may provide a clear and concise methodology to work with $3^{rd}$ party client side frameworks.

Architecture: the pieces of the application may be organized, consistent and predictable. Consequently, the components of the application should be easy to locate and it should be easy to understand the purpose thereof.

Some embodiments include two layers: a Data Notation Architecture (DNA) layer and a Resolution Notation Architecture (RNA) layer. DNA is made up of declarative script (markup) models with services, or put another way, nouns and verbs, respectively. RNA provides instructions on how the code is to be generated, which may enable programming to be performed more rapidly, concisely, and accurately than is currently possible with conventional tools. This DNA/RNA approach is hereinafter called the "Genetic Framework."

The Genetic Framework is a robust pattern framework that does much of the heavy lifting of dynamic binding, code generation definition, type conversions, dynamic logical operations, filtering, and navigation. The pattern framework is important in the code generator, rendered code, and application layers in some embodiments. A sophisticated tagging system is implemented in some embodiments, which is used to manage security, general functionality, navigation, and general system settings. A portion of the framework may be embedded in the database in order to enhance the functionality. This structure could be used to model sophisticated data scenarios, including regression analysis.

The Genetic Framework is unique, providing a way to generate appropriate and well-thought-out code at every level of a given application in some embodiments. The Genetic Framework in some embodiments is also comprehensive. When targeting the Service Area Architecture Pattern (SAAP), which is described in detail later herein, this framework may greatly reduce the overall cost of virtually every part of the software development lifecycle. The Genetic Framework may reduce the number of lines of code a developer has to write. With the Genetic Framework, the targeted code may meet the exacting standards of a skilled software architect with near absolute certainty. The need for testing and review may thus be reduced. This often results in a reduction in the amount of hours required to develop the application and the number of team members required, while at the same time producing a better end software product.

The Genetic Framework of some embodiments is based on a relatively simple set of flexible rules. These rules determine how an application will be structured. The generated code can be quickly adapted to fit a new pattern with the support of this framework. When properly implemented in some embodiments, the generated code will be clean, well-formatted code that is easier to read. The code of some embodiments is well organized and structured, and correctly distributed over multiple files (i.e., not monolithic).

DNA in some embodiments is made up of declarative script (markup) models with services, or put another way, nouns and verbs, respectively. Models have fields and/or properties, and fields may have names, types, lengths, etc. Models and fields may be changed with each successive generation in some embodiments.

Models are identified and linked together using a Polymorphic Relational Path Language (PRPL) tagging system in some embodiments. PRPL in some embodiments is a scripting language that is designed and optimized to resolve various hierarchy and set theory problems that naturally appear in programming. The PRPL language may have a minimal number of rules, be extendable, and be used to query, resolve, and coordinate data from outside data sources. PRPL may also be discrete and work with data sets that have gaps. PRPL may be embedded inside of a Uniform Resource Locator (URL) or Asynchronous JavaScript and XML (AJAX) request in some embodiments.

A database model may be connected to one or more service models. One or more display components may generally represent a given service model. A display model may require multiple actions corresponding to various services, connect to data repositories, and connect to a database in some embodiments. Instead of taking the typical approach of spelling out all of the models and each of the layers, along with each of the corresponding services, the DNA layer can describe these relationships with programmatic precision in some embodiments.

Changes may be made incrementally to the DNA and RNA files in some embodiments. These changes commonly result in the need for a recompilation in order to be reflected in the generated code of the target application. There are a number of common service tasks that can be implemented in some embodiments, including, but not limited to, data mapping (bi-directional), Create, Read, Update, and Delete (CRUD), validation, etc.

The Genetic Framework, SAAP, and PRPL are all innovative in and of themselves. Together, they form a truly powerful tool that can greatly improve the software development process.

In an embodiment, a computer-implemented method includes generating, by a computing system, declarative script models with services using DNA. DNA provides a structure to identify and modify data schemas. The computer-implemented method also includes creating instructions on how corresponding target application code is to be generated, by the computing system, using RNA. A given RNA file categorically qualifies and defines how DNA base pairs are resolved in the corresponding target application code. The computer-implemented method further includes generating rendered code and markup files for a corresponding target application as a part of a Genetic layer to be executed by a computing system associated with the corresponding target application using the RNA to create precompiled RNA.

In another embodiment, a computer program is embodied on a non-transitory computer-readable medium. The program is configured to cause at least one processor to create instructions on how corresponding target application code is to be generated using RNA. A given RNA file categorically qualifies and defines how DNA base pairs are resolved in the corresponding target application code. The computer program is also configured to cause the at least one processor to recursively resolve the RNA using recursive descent. The computer program is further configured to cause the at least one processor to generate rendered code and markup files for a corresponding target application as a part of a Genetic layer to be executed by a computing system associated with the corresponding target application using the RNA to create precompiled RNA.

In yet another embodiment, a computer-implemented method includes generating, by a computing system, declarative script models with services using DNA. DNA provides a structure to identify and modify data schemas.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 6 illustrates example operations of various operators, according to an embodiment of the present invention.

FIG. 13A is a route example illustrating how an example route should be parsed, according to an embodiment of the present invention.

FIG. 13B illustrates an example syntax of how the same query can be written more explicitly.

FIG. 16 illustrates an initial set of target operators, according to an embodiment of the present invention.

FIG. 24 illustrates a polymorphic child pattern, according to an embodiment of the present invention.

FIG. 26 illustrates PRPL node attribute criteria composition, according to an embodiment of the present invention.

FIG. 37 is a service diagram illustrating when a secondary service is requested within a method definition, according to an embodiment of the present invention.

FIG. 43 illustrates dynamic operator flow patterns, according to an embodiment of the present invention.

DETAILED DESCRIPTION OF THE EMBODIMENTS

Figure 1:
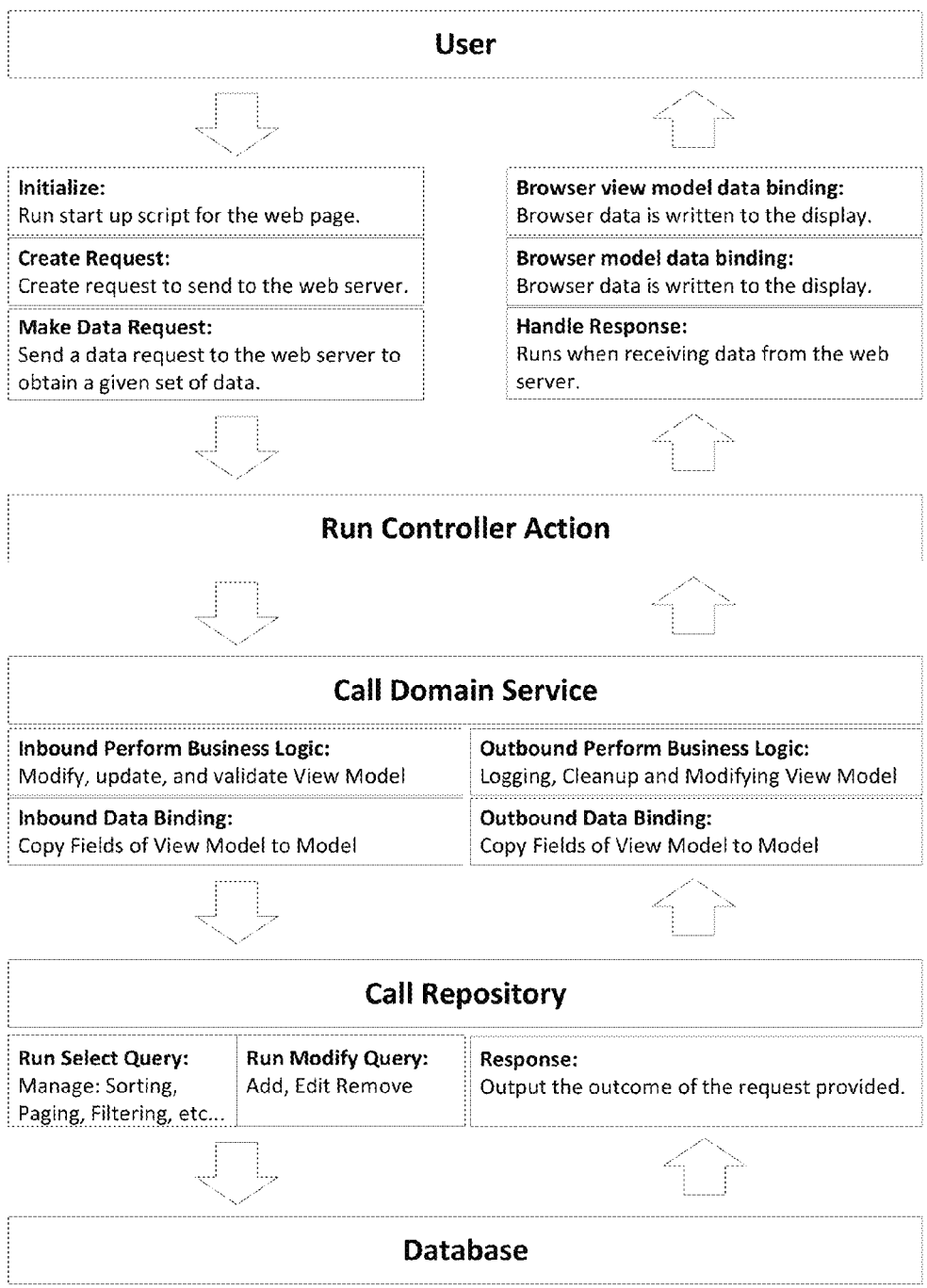
FIG. 1 is a flow diagram illustrating the MVVM model.

Some embodiments of the present invention pertain to a software development tool including a DNA layer and an RNA layer. The software development tool uses a workflow pattern that describes software applications. Such embodiments may be capable of creating full end-to-end code patterns. The Genetic Framework may generate code to build a target application, as well as scripts created and used at runtime.

The Genetic Framework may be flexible because the genetic pattern is customizable. A software engineer or architect may configure the information that is gathered about how a data source (e.g., a database) is built, as well as describe what the target code looks like. As a result, the generated code may follow, extend, or deviate from existing patterns. This makes some embodiments fluid, not rigid like conventional tools.

The novel framework of the tool of some embodiments gives a development team the ability to greatly improve the delivered product. The tool may provide well-managed, organized, structured, and clean code. Cost of oversite, testing, development, and maintenance could drop sharply.

The SAAP pattern may provide improved flexibility and testability. This is the beginning of contextual inheritance—a new three-dimensional methodology of computer programming. Related parts are generally in close proximity. There is a clear path to identify and factor out other patterns. More advanced features, such as dynamic operators, can further extend the power and utility of the framework.

The Genetic Framework provides a means to gather metadata into an organized structure. DNA uses "cascading inheritance" in some embodiments, which is used to elegantly define the meaning of the various nodes of data. The metadata may be organized into base pairs with origin and complement components, which are used to compose the final product. RNA may describe code patterns that are the building block instructions for the generated portions of the target application.

All of this may be tied together with PRPL. PRPL is a specialized programming language that may be used to relate disjointed components. This language provides a relatively simple way to simultaneously query different component types with minimal effort. The language, though it may be limited in scope, is highly flexible and extendible. PRPL may be used to identify, select, and invoke actions. It may also be tied to provide a simple, but powerful, security infrastructure for these disparate components.

Overall Software Development Tool

As discussed above, some embodiments of the Genetic Framework include two layers: the DNA layer and the RNA layer. DNA is made up of declarative script (markup) models with services, or put another way, nouns and verbs, respectively. RNA provides instructions on how the code is to be generated, which may enable programming to be performed more rapidly, concisely, and accurately than currently possible with conventional tools. Precompiled RNA may produce code that is seated in a generated layer of the target application. A controller project in the tool may orchestrate the code generation.

At runtime, Hypertext Markup Language (HTML), JavaScript, and Cascading Style Sheets (CSS) may be created in some embodiments for web applications. However, other languages may be used in certain embodiments, and other applications may be produced, without deviating from the scope of the invention. Each of these generated components may follow a similar methodology of the precompiled library respective to the related display. The client request may indicate what the targeted model/service is. DNA describes the relationships in some embodiments.

In some embodiments, the relationship is defined by DNA referencing other DNA files. A given RNA file may categorically qualify and define how the DNA file is resolved in code. A given DNA may have multiple DNA files or be a complement to different DNA files. The relationships between DNA files may be described using a PRPL tag. This may be observed in some embodiments in four distinct patterns:

(1) Generally, a DNA file will be progressively created for each Genetic Framework layer. A data element may be represented in some embodiments with a data layer, a domain layer, etc. If the DNA file represents a customer, the customer PRPL may read as follows:

App\Customer
App~Domain\Customer
App~Domain~Display\Customer (2) Through a process of multiplication, a DNA layer may create several files. These files may be representative variations of a given data entity, e.g.:
App~Domain\Customer\Delete
App~Domain\Customer\Add
App~Domain\Customer\Edit
App~Domain\Customer\View (3) There may be a relationship between different entity types (i.e., foreign keys). These relationships may be identifiable through some sort of PRPL route. Some relationships may be nested, such as:
App~Domain \Customer~Phone
Non-nested relationships may also be referenced, such as:
App~Domain\Invoice
These relationships may be described explicitly in the respective DNA file.

(4) DNA files may also be created manually at any layer in some embodiments.

In some embodiments, when processing the RNA, DNA is related into base pairs taking each of these scenarios into account. Each RNA file may qualify which DNA base pair can be used to generate a given code file resource. The code file can represent a model, service, visual resource, etc.

User privileges may be used to determine what components will be rendered or blocked. For instance, if "Delete" privileges are required for deleting a record, but not granted to the current user, the corresponding Delete HTML and JavaScript may be excluded from the rendered content. Additionally, the client may also determine what is rendered (e.g., browser, device type, language, etc.).

The initial target platform of some embodiments is the C#4.6 framework and will be implemented using the SAAP pattern. These same technical concepts may be ported to other languages in some embodiments. Even though some of the terminology used in the examples herein is specific to a Microsoft™ implementation, the general concepts are not implementation-specific. In the future, these concepts may be extended to support other development ecosystems, such as Java or Objective-C. The basic concept of some embodiments is to decouple the nouns and verbs, or in the technical vernacular, models and actions. Some embodiments involve a higher level programming language—i.e., a program to make other programs. Managing code in a concise and descriptive manner can be a pivotal part of decreasing the overall cost of developing and maintaining an application.

Figure 2:
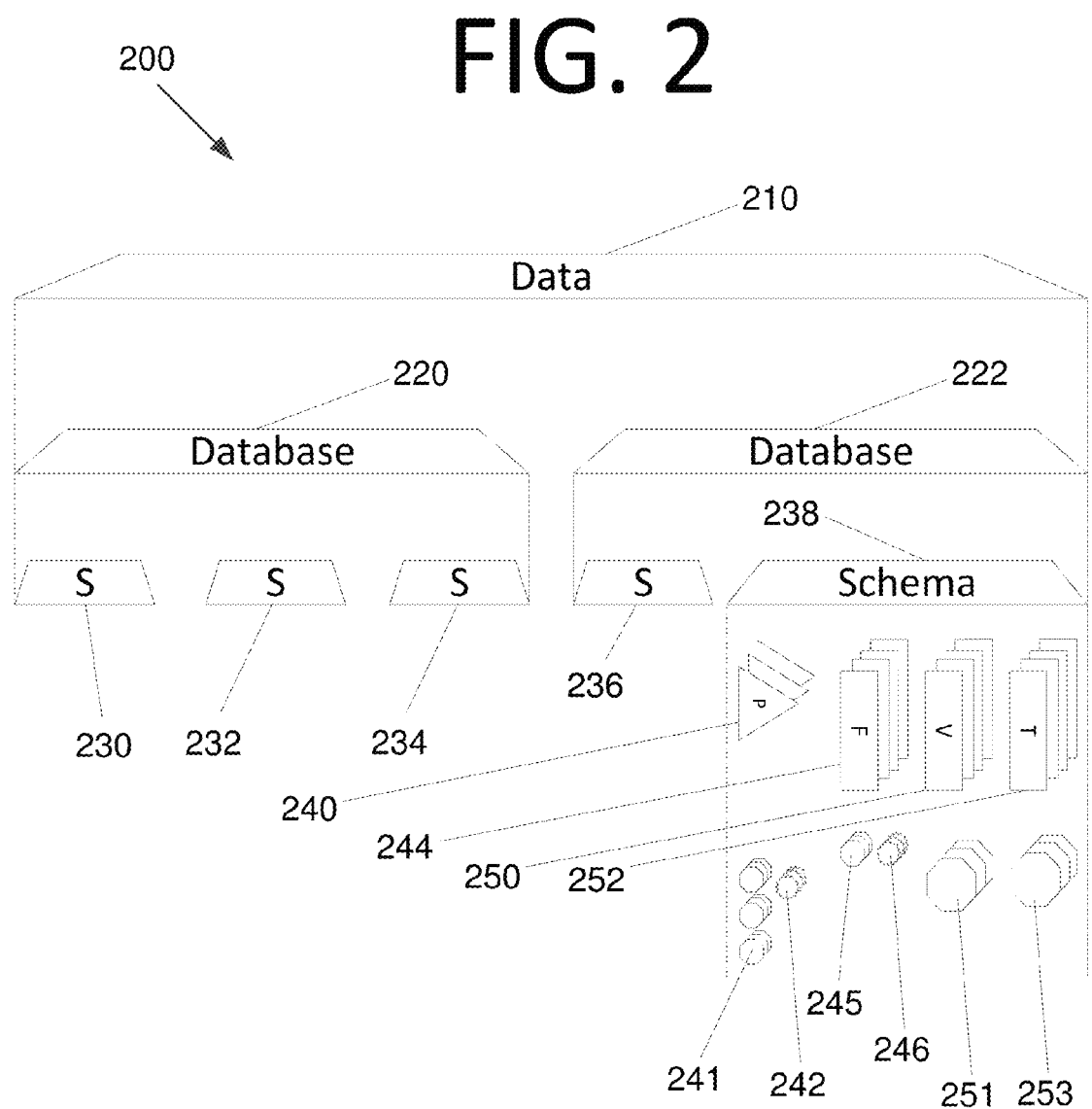
FIG. 2 is an architectural diagram illustrating an SAAP database pattern, according to an embodiment of the present invention.

FIG. 2 is an architectural view illustrating an SAAP database pattern 200, according to an embodiment of the present invention. Data layer 210 holds multiple databases 220, 222. Each database holds multiple schemas. More specifically, database 220 holds schemas 230, 232, 234 and database 222 holds schemas 236, 238. Schemas are definitions of how the database is structured.

Each schema holds procedures, functions, views, and tables. For instance, schema 238 includes procedures 240, functions 244, views 250, and tables 252. Individual procedures, functions, views, and tables hold columns and parameters, along with corresponding metadata associated with respective database objects. Procedures 240 have "in" parameters 241 and "out" parameters 242. Views 250 and tables 252 have columns 251 and 253, respectively. Functions 244 have columns 245 and parameters 246.

DNA may provide the instructions on how to build many of the predictable aspects of the application (e.g., a web application). There are four major components in some embodiments: library references, information reflective of relevant database structures, declarative markup, and script templates. More specifically, library references are included as dependences of the project. Information reflective of the relevant database structures is compiled. This provides the layout of a given database's schema, views, tables, functions, procedures, etc.

Declarative markup provides the metadata for the construction of the repository, domain, controller, client scripts, and markup. Each markup script associates the database to a unit of work, and ultimately, the use display. Script templates include a series of C#, XML, and text files that provide the definition on how the code is to be laid out in some embodiments. These templates may be resolved using PRPL.

The DNA layer includes one or more data sources and possesses the data to be used by the target application in some embodiments. Some databases may be self-descriptive, and others may not be. Relational databases, such as SQL Server™ and Oracle™, are self-descriptive, meaning that they hold their own schema. Certain databases, including NoSQL databases such as Mongo DB™, are generally freeform, or non-descriptive. Properly distributing the schema content over multiple files improves readability, simplifying defect detection.

Figure 3:
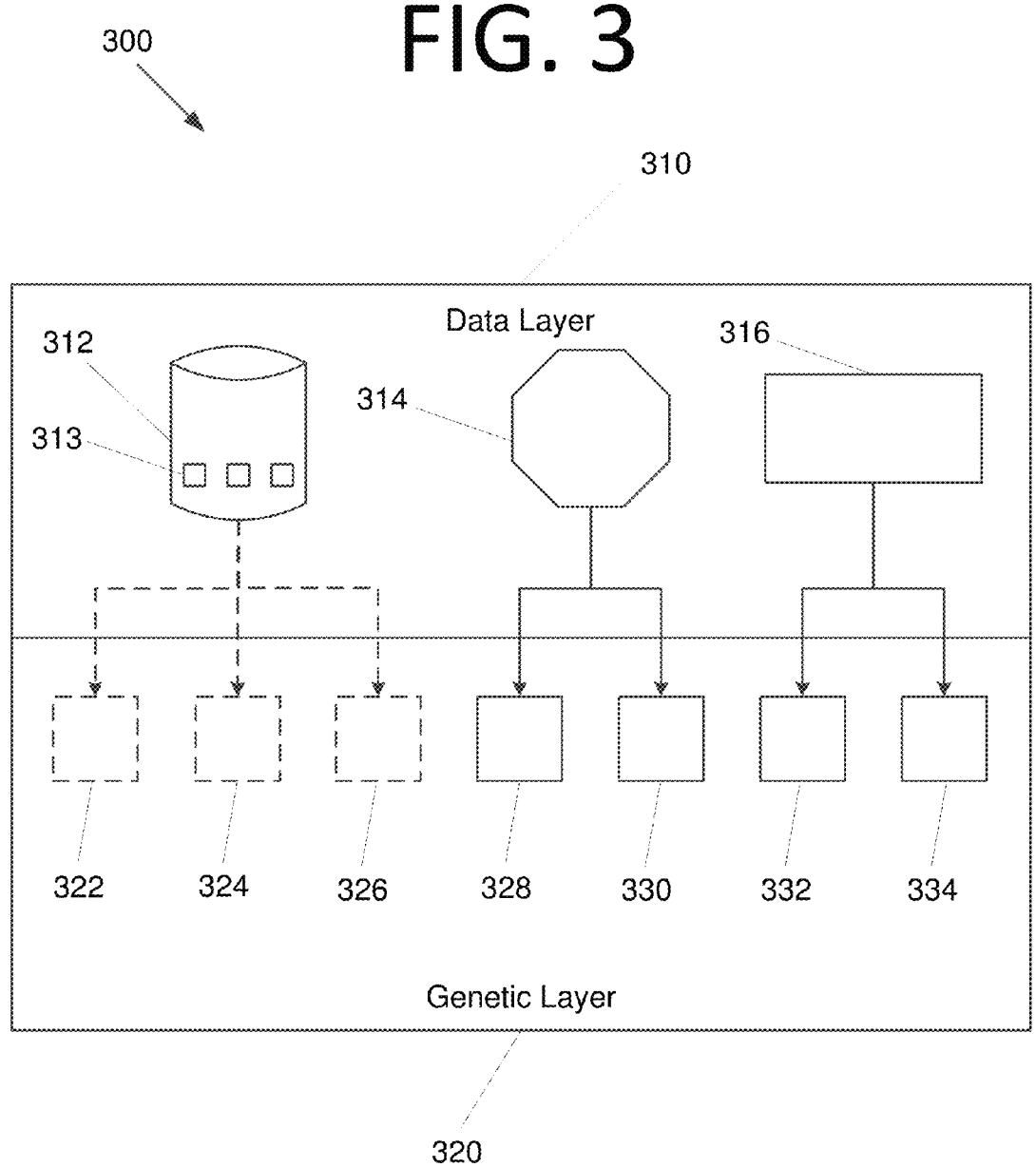
FIG. 3 is an architectural diagram illustrating layers for initialization of data schemas managing self-describing, non-descriptive, and implied data sources, according to an embodiment of the present invention.

FIG. 3 is an architectural diagram illustrating layers 300 for initialization of data schemas, according to an embodiment of the present invention. Layers 300 include a data layer 310 and a Genetic layer 320. Data layer 310 includes a self-descriptive database 312, a non-descriptive database 314, and no data source 316. Self-descriptive database 312 includes multiple schemas 313.

In some embodiments of DNA, the data source is a placeholder for the model definition. In that sense, DNA is not referring to any given data source in these embodiments. Rather, the data source could be used in other parts of the application, or not used at all (i.e., no data source).

Genetic layer 320 also includes data schemas 322-334. In the case of data schemas 322, 324, 326, schemas 313 in self-describing database 312 can provide the initial data schemas. The definition is dependent upon the reflective query provided to the database. In the case of data schemas 328, 330, 332, 334, these come from non-descriptive database 314, or no database 316 is present at all. No initial data schema is provided, and the definition needs to be supplemented. Typically, this is done with a manually constructed markup file.

Genetic Layer

The Genetic layer holds a templated version of the target application, such as a web application. However, other target applications may be used without deviating from the scope of the invention. Each project generated in the target application may be represented by a corresponding Genetic layer project. The controller project may be executed to trigger non-runtime code generation for the target application. Runtime code generation may be managed in the target application with components provided by the Genetic layer.

Application Layer

The application layer defines the application. The Genetic layer can inject code in a well-defined, tightly constrained space inside of the application layer. When the Genetic Framework targets the SAAP pattern, a custom layer provides an effective space to override and extend the generated logic.

Data Notation Architecture (DNA)

DNA provides a structure to identify and modify data schemas. In other words, DNA allows description of the "shape" of a data element (i.e., the complement of attribute/field references (e.g., name, data type and metadata) and relationships to other DNA elements). A data element can be made to describe any part component of the data schema for a database or other data source, including, but not limited to, a table, a view, a function, a procedure, an index, a key, a field, or a column. Schemas may be generated or manually assigned, and may be based on markup and code that can be generated as markup.

DNA resolution has two components which makeup a base pair: the origin and the complement. The origin refers to a starting component for a given step in resolution. The Complement refers to the component instructions on how to modify the origin. DNA may be manually created as well as generated from code or some other automated process, such as processes (1) to (4) described above. An example is a reflective query of a database that is based on its table, views, or other schema components. Using the genetic process, services and the user interface (UI) can be generated according to user-defined patterns. DNA resolution may use cascading inheritance to accomplish multiple layers of simultaneous modifications to a given source file.

A given DNA file may be either in a resolved or unresolved state. The state of resolution for a given origin file may be determined if there are any remaining commands. If there are no remaining commands, the DNA file is resolved and is ready to be processed by another DNA layer or as part of the RNA process, described in more detail below. An unresolved file may be processed until the all of the commands have been resolved. Resolving a given command results in a series of changes in some embodiments including, but not limited to, the addition of more commands.

DNA may be configured to describe each individual component and express the relationship toward other components. With the support of PRPL, these descriptive components may be appropriately broken up into separate readable files. This allows the files to be both human and machine-readable, rendering code that can be more easily isolated and tested.

A series of DNA templates may be used to qualify, split, multiply, and extend the initial data layer. Using the Genetic Framework, any component at any level can be overridden and extended in some embodiments. The object to be modified is defined as the "origin" herein. The resource origin is operated on with what is defined as the "complement" herein. The outcome of the origin being combined with the complement is defined as the "result" herein. Cascading inheritance diagram 400 of FIG. 4 shows an example of how the metadata of a given field can be modified in a relatively simple process.

Figure 4:
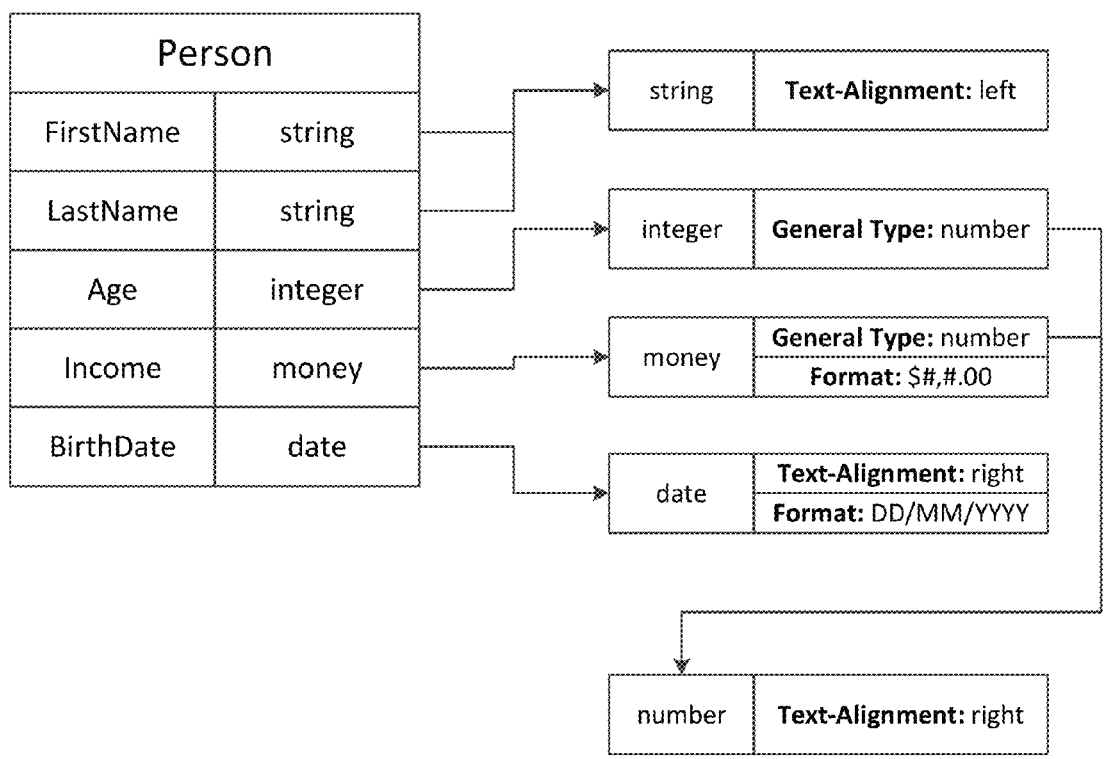
FIG. 4 is an inheritance diagram illustrating an example of cascading inheritance, according to an embodiment of the present invention.

In FIG. 4, the class Person includes the fields FirstName, LastName, Age, Income, and BirthDate. The FirstName field is identified as a string, and string is left-justified. However, the Age field is a bit more involved. Age is identified as an integer. An integer is defined as having the General Type number, and number is right-justified. FIG. 4 is intended to be for illustrative purposes only, and a myriad of other variations and applications of cascading inheritance are contemplated herein without deviating from the scope of the invention. The developer utilizing the Genetic Framework can modify the cascading behavior as he or she sees fit. Properties at the various layers are listed in Table 1 below.

TABLE 1

PROPERTY BEHAVIOR BY LAYER

| Layer: | Name: | Data Type: | General Type: | Text-Alignment: | Format: |
|---|---|---|---|---|---|
| Table | FirstName | string | Not Set | Not Set | Not Set |
| Table | FirstName | string | Not Set | left | Not Set |

TABLE 1-continued

PROPERTY BEHAVIOR BY LAYER

| Layer: | Name: | Data Type: | General Type: | Text-Alignment: | Format: |
|---|---|---|---|---|---|
| string | LastName | string | Not Set | Not Set | Not Set |
| string | LastName | string | Not Set | left | Not Set |
| Table | Age | integer | Not Set | Not Set | Not Set |
| integer | Age | integer | number | Not Set | Not Set |
| number | Age | integer | number | right | Not Set |
| Table | Income | money | Not Set | Not Set | Not Set |
| money | Income | money | number | right | $#,#.00 |
| number | Income | money | number | right | $#,#.00 |
| Table | BirthDate | date | Not Set | Not Set | Not Set |
| date | BirthDate | date | Not Set | right | DD/MM/YYYY |

"Person" can have an override defined in each successive layer. As such, Person is not itself a layer, but its definition can change from one layer to another. Multiple facets can change using complements, which is the basis of cascading inheritance in some embodiments.

A primary goal of DNA and cascading inheritance in some embodiments is to substitute complexity with simplicity. The can be done quite intuitively and the framework will handle it well. For example, small int(s), int(s), and big int(s) are all integers. Decimals, floats, and money are all decimals (i.e., floating point). Decimals and integers are both numbers. Numbers and dates are right-justified and can perform arithmetic expressions. The primary alternative is to examine and compare the corresponding data type to see if it is small int, int, big int, decimal, float, money, date, datetime, datetime2, etc. This is but one example, and there are any number of possible dimensions for a given schema fragment. Keeping track of one variable is relatively straightforward, but keeping track of fifty is considerably more complex.

Considerable simplification can be provided by using just one dimension. For instance, consider date as an example. The date is commonly represented as a masked entry field or some sort of calendar control. Putting the principal logic into the genetic components means that date can be described in one place and automatically applied everywhere. In the event that the calendar needs to be upgraded, one can simply replace the definition and move on. This framework can be extended to any computing system (e.g., personal computers, mobile devices, servers, consumer and industrial electronics, vehicle systems, etc.) without deviating from the scope of the invention by extending the framework using PRPL. This provides minimal complications.

Multiple dimensions for a single data point can be evaluated to create a new data point. If checkboxes are used to represent required fields, DNA could resolve to a new data point called "checkbox." Checkbox may be marked as "true" when a given field is both a bit and required. Even better, checkbox could be resolved to a data point called "input type" with a value of "checkbox." Now, a single data point can be used to perform a single, specific operation.

Figure 5:
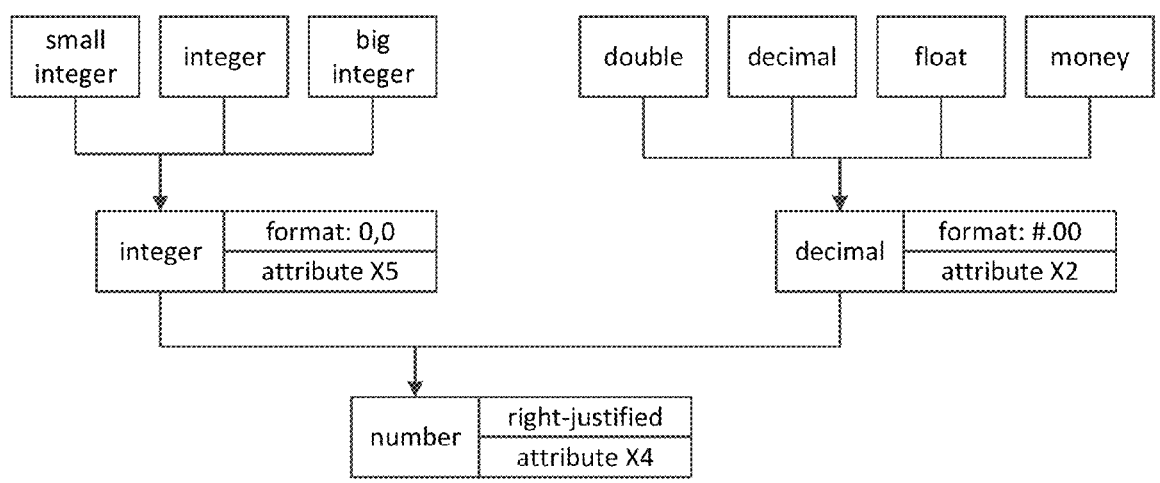
FIG. 5 is a hierarchy diagram illustrating an example cascading inheritance hierarchy, according to an embodiment of the present invention.

The example cascading inheritance hierarchy 500 of FIG. 5 further demonstrates the potential value of cascading inheritance in some embodiments. Take, for example, the big integer. Big integer inherits the integer general type. The integer general type provides a definition for the format, along with five other attributes, including number as a new general type. Number provides instructions for five attributes, including the text alignment, which is left-justified.

A resource or attribute may be called using various operators in some embodiments. An example 600 of various operators operating on money and decimal is shown in FIG. 6. In this example, the operators are: write, prewrite, overwrite, append, and prepend. Write assigns an attribute regardless of what the existing assigned value is. Prewrite assigns an attribute even if its value does not exist. Overwrite assigns an attribute only if the value does not already exist. Append will take the existing attribute value and append the complement value to the end of the attribute. Prepend will take the existing attribute value and append the complement value to the beginning of the attribute.

The operators may be defined using dynamic operators from the SAAP framework, and therefore, can be easily extended. "Apply operator" will pass an operator instruction to the origin structure to be processed as part of the product in due course. Apply affects the complement. After the complement is resolved, it would affect the origin document. The apply operator is analogous to a traditional function. The complement, while unresolved, behaves as the origin RNA until it is fully resolved. Ultimately, the origin gets resolved to the target application.

With respect to some embodiments, the operator [hlx-apply-overwrite:My Structure] would apply an overwrite using My Structure. It would then be converted to [hlx-overwrite:My Structure] in the corresponding place in the new structure. In the event that the data point already exists, it may be prepended the corresponding text or attribute.

Figure 7:
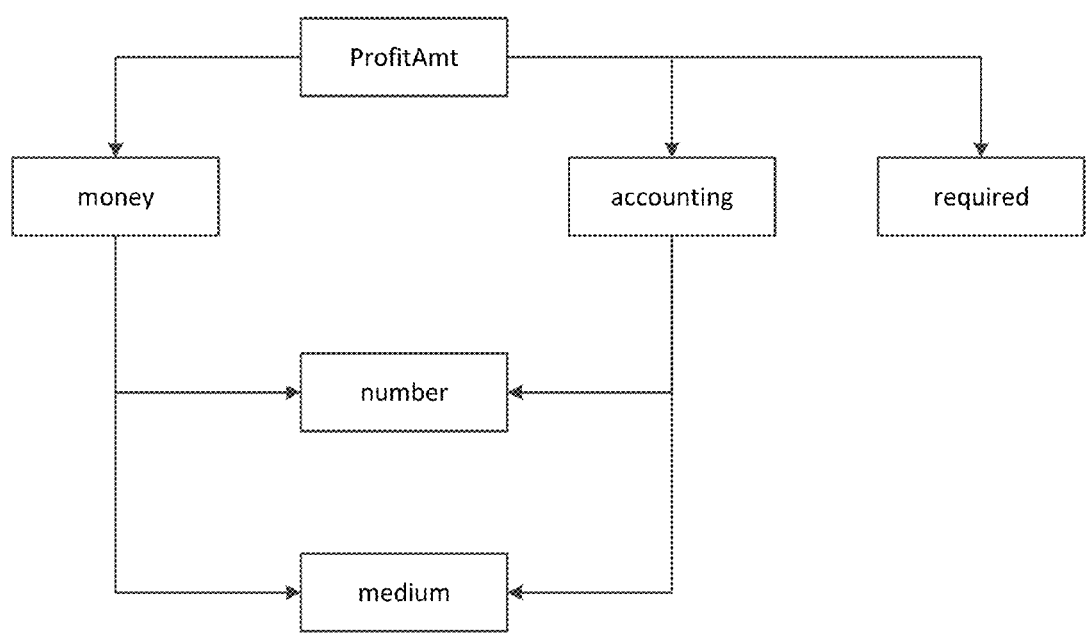
FIG. 7 is an inheritance diagram illustrating an advanced example of cascading inheritance, according to an embodiment of the present invention.

Advanced cascading inheritance pattern diagram 700 of FIG. 7 demonstrates how more sophisticated patterns can be constructed using the various attributes of metadata. ProfitAmt inherits from three different complements: money, accounting, and required. The complement money comes from the data type from the database. The complement accounting could be made to key off the Amt portion of the field name. The complement required comes from the "Is Null" attribute, also defined in the database. The complements money and accounting both inherit from number and medium.

Figure 8:
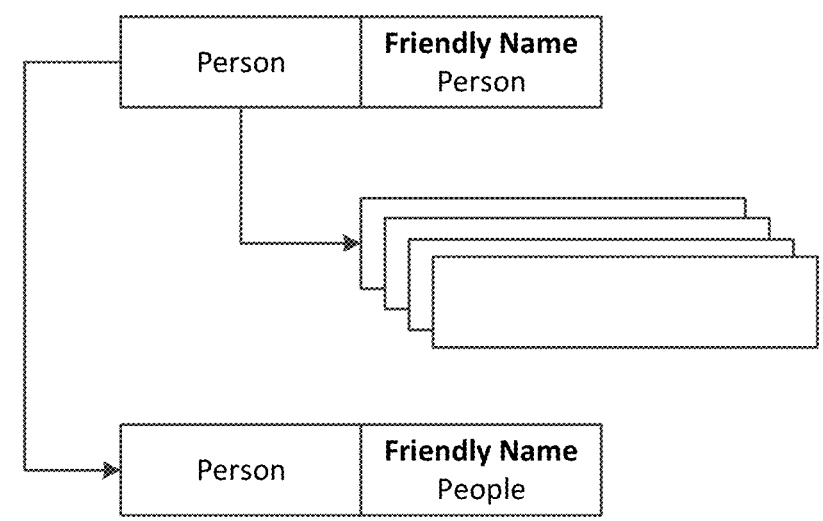
FIG. 8 is a model level DNA diagram, according to an embodiment of the present invention.

Model level DNA diagram 800 of FIG. 8 shows how a DNA complement can be used to override a table, and is not limited to field manipulation in some embodiments. In FIG. 8, the Person table is being modified. The fields of the Person table are ancillary. The Person table uses a Person complement to override the Friendly Name. This can be done with another markup file, or using a precompiled method. The distinction between a friendly name and a system name is shown here. An entity or field in code may be described in a particular manner that would not be intuitively identifiable by the user.

Figure 9:
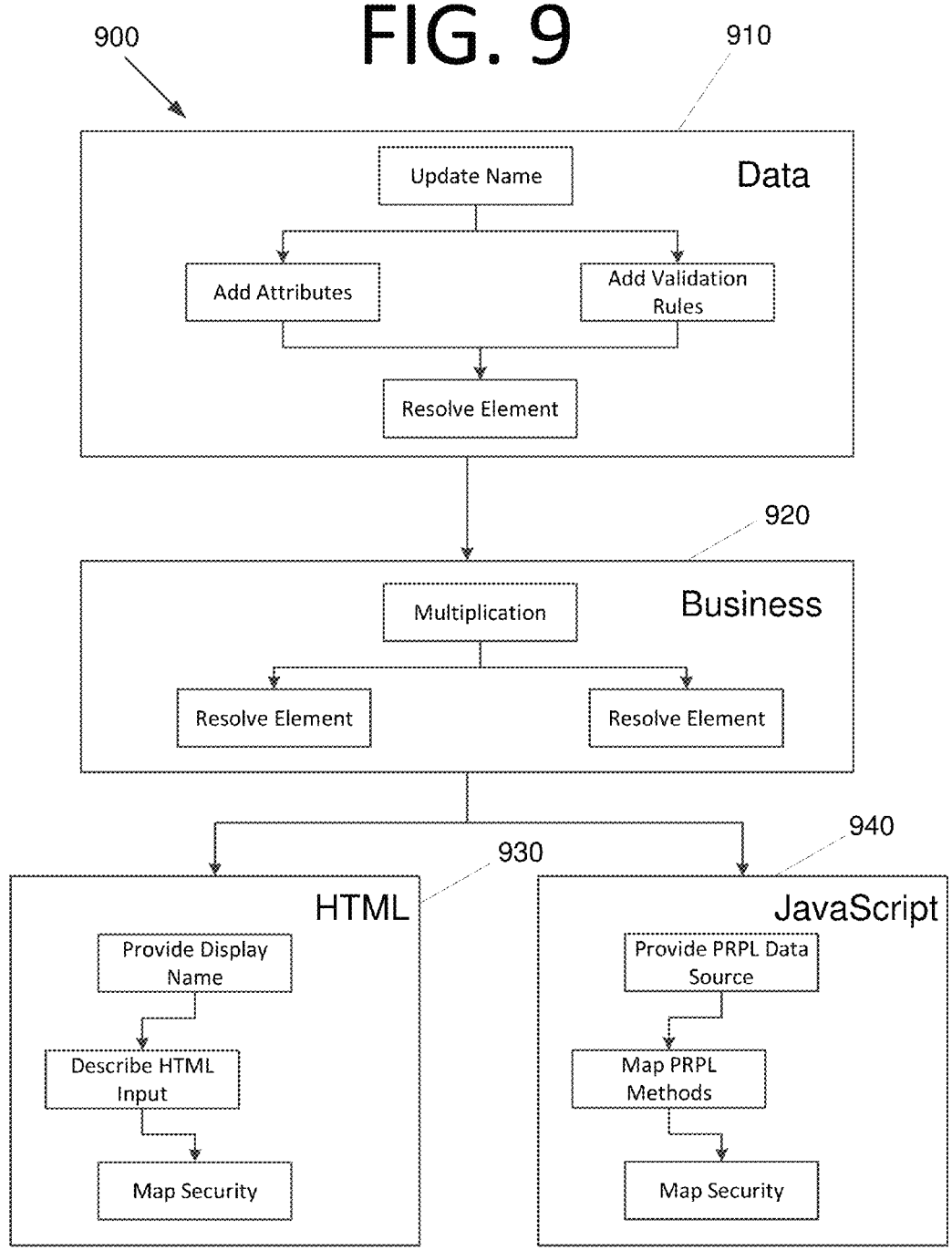
FIG. 9 illustrates cascading inheritance spanning multiple projects, according to an embodiment of the present invention.

Cascading inheritance spanning projects diagram 900 of FIG. 9 shows how a model/service may be modified or split to accomplish focused patterns for tasks. The patterns follow simple and flexible rules. They are fluid, not rigid. If the patterns or rules become inadequate, a developer can easily alter them.

In data layer 910, "Resolve Element" refers to implementing cascading inheritance. Resolve Element iteratively attempts to resolve the origin, continuing to reference corresponding complements, until there are no longer any "hlx-" nodes. Subsequently generated layers (e.g., business layer 920) have a series of template documents that are compared to the DNA products of the previous layer. These documents qualify which proposed DNA compliments apply. Because there can be multiple origin templates, and because a complement can qualify for more than one origin template, this can have an effect of multiplication. After multiplication, a step of resolution will occur for each successive file generated in the multiplication process.

Respective HTML 930 and JavaScript 940 is then generated for these files. For HTML 930, a display name is provided, the HTML input is described, and security is mapped in this embodiment. For JavaScript, a PRPL data source is mapped, PRPL methods are mapped, and security is mapped in this embodiment.

Example DNA Implementation

In some embodiments, the prpl-name attribute acts as a point of reference for identifying how the origin and complement should align. The PRPL language may also be used as a means to navigate through a given document. The name of the document, for instance, may be its controller. Using the "Person" example in FIG. 4 and the associated discussion thereof above, the element Person for a person named Peter Kotman may be referred to with Root~Peter Kotman.

```
<Root prpl-path="Root">
    <Person FirstName="Peter" LastName="Kotman" prpl-name="Peter
       Kotman" />
</Root>
```

The Person element can also be referred to by

```
<Root prpl-path="[tagname]">
    <Person FirstName="Peter" LastName="Kotman"
        prpl-name="[attr-FirstName] [attr-LastName]" />
</Root>
```

Note that the [tagname] command interjects the word "Root" into the path. The Phone Number element can be referred to with Root\Peter Kotman~(555) 555-5555 or Peter Kotman~(555) 555-5555. Note that the prpl-path restarts the name/path.

```
<Root prpl-path="[tagname]">
    <Person FirstName="Peter" LastName="Kotman" prpl-path="Peter
       Kotman">
        <Phone Number="(555) 555-5555" prpl-name="[Number]" />
    </Person>
</Root>
```

The data points of the origin and complement structures may be used as markers of how the origin structure should be altered in order to generate the product (i.e., the target application). A data point is defined herein as a text, element, or attribute node. The element can be referenced by putting the "hlx" prefix in front of it in some embodiments, e.g.:

```
<hlx-command>
    [htx-overwrite: value]
</hlx-command>
```

The best practice is to use the hlx-command to manage commands for a given element. While the "hlx" prefix is used herein, any desired prefix may be used without deviating from the scope of the invention.

Generating a product markup may involve the following. Resolved DNA structures from the previous generation may be identified. Generally, this will be the database for web applications, but there does not have to be a genetic point of origin. The complement may then be identified and loaded.

This can be done either uniquely or categorically. Unique qualification means that a specific base pair will behave in a given way. Its implementation is identical to that of the categorical qualification. The difference is that only one base pair is being targeted for acceptance or rejection.

The categorical qualifier may provide a means for determining which products will be generated. There will be two types of categorical qualifiers in some embodiments—pre-qualifiers and post-qualifiers, which will execute before and after mitosis (i.e., "resolution," described below) is attempted, respectively. An example of categorical qualification may be only implementing a service for a primary table. A primary table may be determined by examining whether a set of fields is present, such as: CreatedDate, CreatedBy, ModifiedDate, and ModifiedBy. Cascading inheritance may be used to create an attribute indicating whether these fields are present. The categorical qualifier of a given RNA file may then, in turn, refer to this attribute as opposed to identifying whether these four fields are present.

The origin structure may be searched for a data point that contains an operator. The operational marker may have a syntax of [hlx-type: value], for instance. The operator structure may be used as the default instruction for each data point that the prefix or the "hlx" label identifies as an operator. The operational marker type may determine which type of operator to be used. The value may resolve the complement to be used. The complement markup or method may then be loaded. The system may identify each markup using PRPL in some embodiments.

Resolution Notation Architecture (RNA)

While DNA describes the nature of the data, RNA does something with the data. RNA follows a similar pattern to DNA in some embodiments. RNA is based on markup and code that can be generated as markup. RNA is designed to generate scripted code for a given target language, e.g., C#, Java, JavaScript, CSS, HTML5, etc. by way of non-limiting example.

RNA and DNA are resolved differently in some embodiments. DNA is resolved using cascading inheritance, which requires base pairs. RNA makes use of DNA base pairs, but its methodology of resolution is functional and recursive (i.e., recursive descent). DNA is paired up with other DNA files, templates, and operators to produce DNA files and affect the outcome of RNA.

Recursive descent generally refers to recursive descent parsing, which is typically a key component of compiler algorithms. A compiler is a program that builds programs. In this case, more specifically, recursive descent refers to a specific path of resolution for hierarchy data structures. A common resolution method may call a corresponding operator method. That operator method could, in turn, call the common resolution method to resolve each of its children. Eventually, each node in the tree will be reached. The output from each operator may then be added to its parent node. The structure is considered fully resolved with the corresponding output for the root node.

DNA base pairs may be qualified for select RNA files. RNA can navigate through its assigned DNA base pairs using iterators, operators, filters, paging, and sorting, for example. Other RNA templates can be identified and resolved from an RNA library.

RNA resolution is done recursively—i.e., functions call functions. The resolved RNA is assigned to a code object type that has an open property (which is the dominate property), a closed property, and children object in some embodiments. The code object may create a natural tree structure, which is fragmented by modules. Modules (or code files) may contain root code, along with information needed to save the file to the appropriate location (e.g., file name and folder).

The Genetic Framework may be customized to support a variety of search patterns in some embodiments, including, but not limited to, AWK, PowerShell, reflection, and PRPL, to identify and appropriately pair the RNA and DNA files. Code may be generated based on any source with which a schema can be represented in markup in some embodiments. Code may be generated to provide both precompiled code and runtime code.

Each genetic project, representing code to be generated in the application solution, possesses a series of code templates in some embodiments. A code component can be constructed with a complement of markup, text, or C# methods in certain embodiments. Each code component represents a specific task to be performed, such as model composition, mapping, filtering, validation, etc. The DNA nodes are combined with a corresponding DNA complement. Each DNA node is qualified to determine the template that is applicable. This methodology can provide a means for engineering declarative automated tests.

DNA nodes refer to a part of a markup document. Origin and complement are contractually related documents and constitute the base pair. The origin may be thought of as the $1^{st}$ party and the complement may be thought of as the $2^{nd}$ party. The node is a generic term that refers to a specific portion of any DNA or RNA structure.

Figure 10:
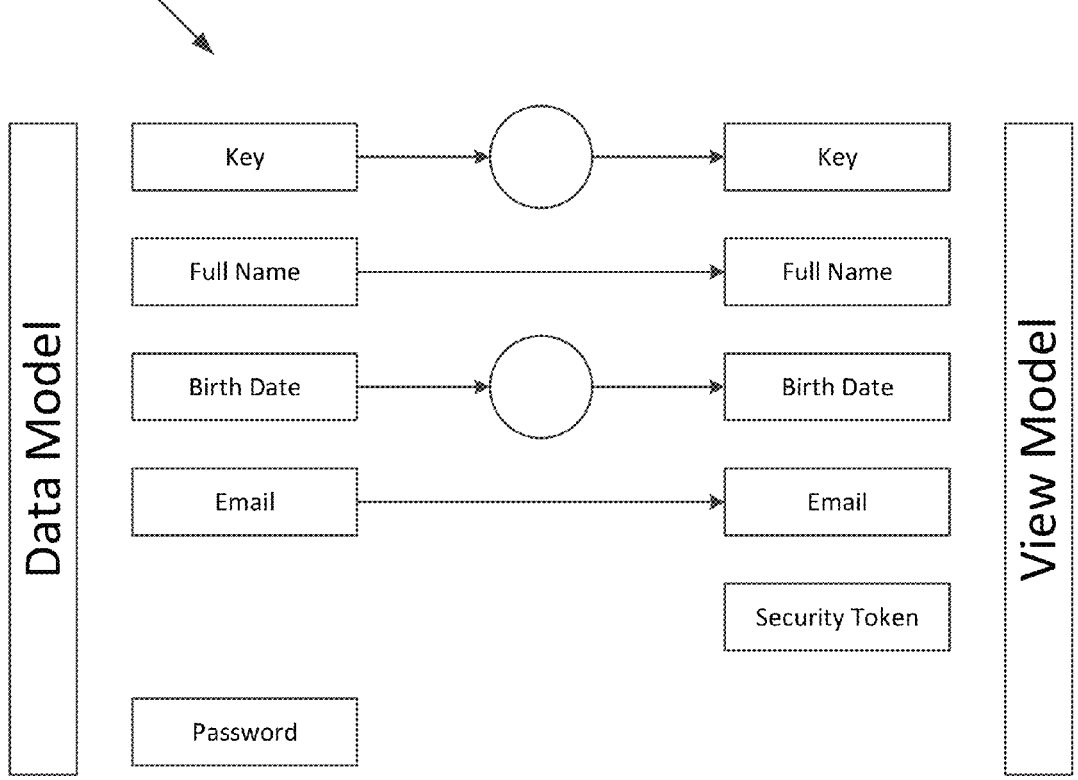
FIG. 10 illustrates explicit mapping between a data model and a view model, according to an embodiment of the present invention.

Mapping 1000 of FIG. 10 illustrates a sample pattern of explicit mapping. The data model and view model have a similar set of fields. The two fields Security Token and Password, one in each model, represent un-complemented fields. The RNA pattern may be programmed to ignore these items in this scenario. The Key and the Birth Date fields both have special logic associated with them, denoted by respective circles. In particular, the Birth Date is likely to be of a date type in the data model and a string type in the view model. These types may be processed into the appropriate format for the respective model. RNA may provide a natural set of tools to resolve such issues that may arise.

RNA can be broken into two categories: precompiled RNA and runtime RNA. Precompiled RNA transfers fully generated code, such as C#. Runtime RNA transfers DNA and RNA templates to be resolved as the target application is running.

Figure 11:
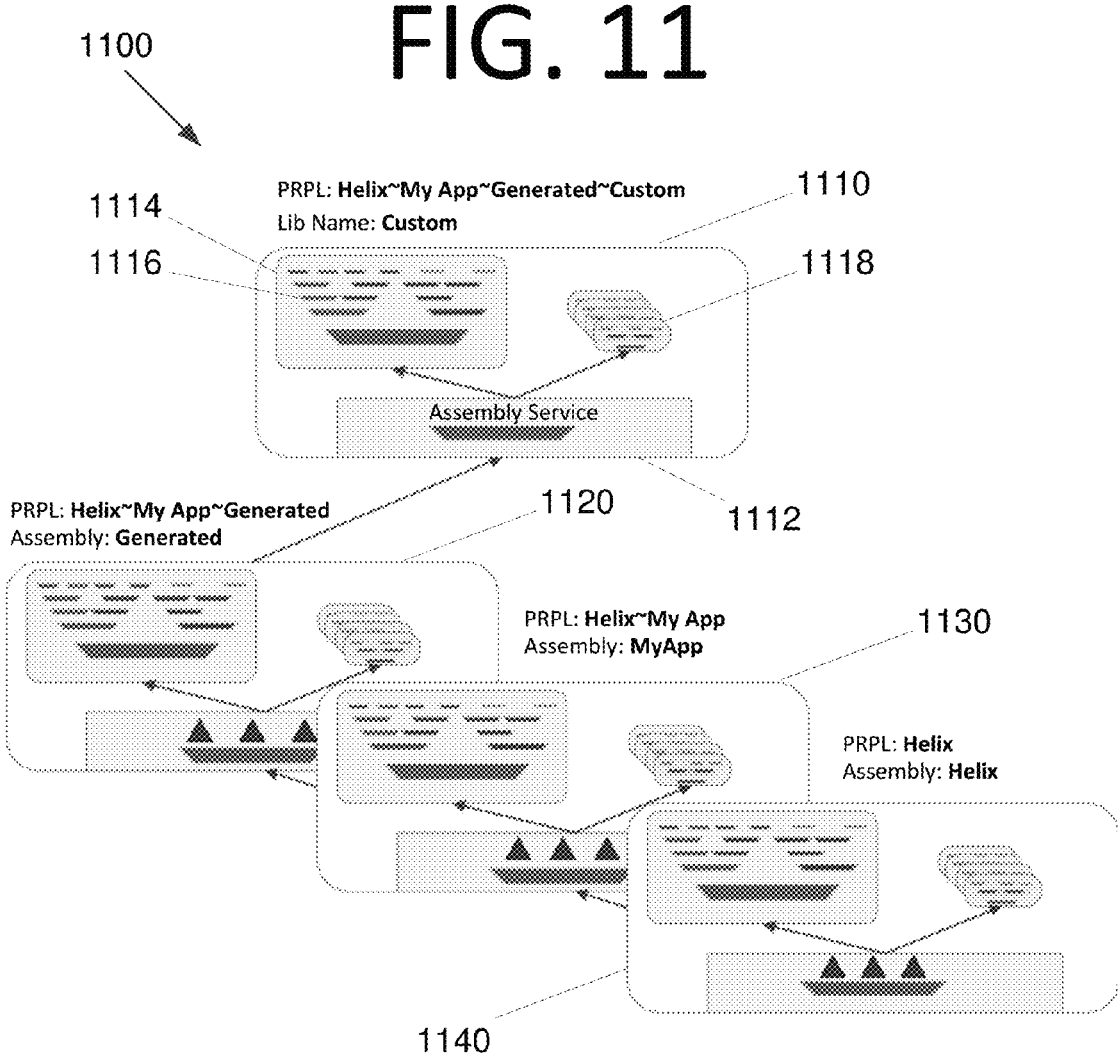
FIG. 11 is a SAAP service resolution diagram, according to an embodiment of the present invention.

FIG. 11 is a SAAP service resolution diagram 1100, according to an embodiment of the present invention. More specifically, SAAP service resolution diagram 1100 shows the general resolution path of a PRPL route to a .Net assembly. The last node in each PRPL string refers to that path. Other language platforms may use a similar language depending on what the respective language could support. The flow object type may determine the route for resolution based on information found in the general service. The general service provides PRPL nodes. Any libraries (dynamically linked libraries (DLLs)) referencing the parent project (i.e., MyApp) may be automatically synchronized in the generated project. Also, any libraries (DLLs) in the Genetic project may be included in the generated project.

Service resolution diagram 1100 includes assemblies or projects 1110, 1120, 1130, 1140, which represent generated layers in a hierarchy container following the SAAP pattern. Code may be confined to specific coding layers regardless of what pattern is used. This practice is rarely, if ever, followed conventionally. It ensures that code can be neatly organized and that custom code is safe from corruption.

Assemblies 1110, 1120, 1130, 1140 include services. Services are a more abstract concept in SAAP. There is a base definition that occurs either in the Genetic Framework or the target application. This core service concept may be extended in the current or subsequent assemblies. Furthermore, any given service may extend the definition of any nested context, or contexts assigned to a host context, in some embodiments.

A general service 1112 that has a container class is included in assembly or project 1110. General service 1112 is responsible for handling project level PRPL resolution tasks. A primary service 1114 may be inherited by the same primary service, as well as secondary services.

Nested contexts 1116 are included within primary service 1114. In some embodiments, it may be necessary to nest context 1116, as well as definitions. Nested branches may be used for testing and permissions differences. Nested branches also provide an economical way to perform small deviations of a given discipline.

Secondary services 1118 are also included in assembly or project 1110. Secondary services 1118 refer to services that are based on a different discipline than primary service 1114. The discipline is a focus of a given service. A file service, for example, would be interested in file operations. For instance, "taxes" may be an example of a primary service, which may become a secondary service when placed in a secondary context. For example, if there was an information technology (IT) budgeting service, "Taxes" methods would be of a secondary context. The methods that were specific to Taxes and defined in this context could be inherited by future generations using contextual inheritance.

Precompiled RNA

Precompiled RNA produces code that will typically be seated in a corresponding target application-generated layer. The controller project in the genetics solution may orchestrate the code generation. The following steps may be performed with each regeneration of the genetic layer in some embodiments.

(1) The Genetic Framework is an extension of the core framework in some embodiments. PRPL may hold references to text, XML documents, or other objects that can be resolved to text. These files may ultimately be saved during a commit process. An in-memory file library will be used in the construction of the generated code in some embodiments. The precompiled libraries may be used as a foundation of the application. At this point, the DNA and RNA may actually be combined together to generate projects and their corresponding components.

The SAAP pattern will be the principal target for services in some embodiments. SAAP may favor packaging variables inside of an object. In some embodiments, SAAP also requires that public methods be defined in the initial layer, even if the override service methods are defined in a different project in order to maintain a contract. This is important when defining the DNA/RNA as described below.

If there is a failure in the code generation, the application projects may not be updated unless otherwise flagged to do so. Diagnostic output, as well as tracing, may provide the developer with breadcrumbs to isolate and resolve the issue. The files can be re-routed to a new location for further examination. Files may be stored per iteration, which may consume a sizable amount of memory. The files may include all of the code and Genetic markup files (e.g., XML/JSON).

(2) File cleanup of the target location is performed, if necessary. All code and DNA files are deleted, unless flagged otherwise.

(3) The generated project file is updated for each layer to reflect any dependencies or third party frameworks present in the genetic layer.

(4) The generated code files are saved to the appropriate locations. It may be necessary to have multiple targets depending on what the debug process is. The primary target may be a web application in some embodiments.

(5) The application should be validated to ensure that it can be built.

Runtime RNA

Runtime RNA produces a resource that cannot be constructed in some embodiments until it is requested via HTML, JavaScript, CSS, etc. Each of these generated components may follow a similar methodology to precompiled RNA respective to the related display. The client request may indicate what the targeted model/service is. The DNA relationships may include DNA referencing other DNA files.

User privileges may be used to determine which components will be rendered or blocked. For instance, if "Delete" privileges are required for deleting a record, but not granted to the current user, the corresponding Delete HTML and JavaScript may be excluded from the rendered content. Additionally, the client may also determine what is rendered (e.g., browser, device type, language, etc.).

The HTML markup may include references to the corresponding binding frameworks (e.g., knockout, angular, backbone, etc.). The initial model-view-presenter (MVP) is targeted to be Aurelia™ in some embodiments, minimizing other web frameworks. The rendered JavaScript may mirror that of the C# namespace. The models and services may be decoupled, and targeted CSS may be contextually generated.

Figure 12:
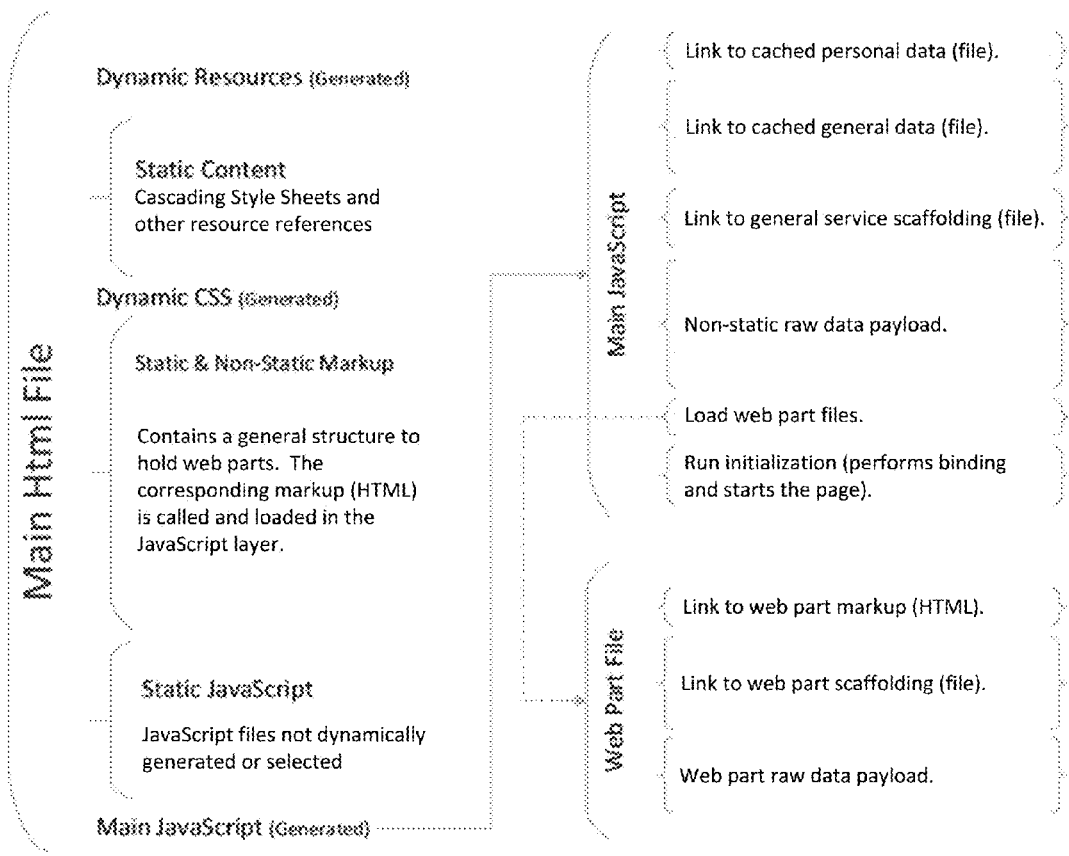
FIG. 12 is a SAAP client initialization diagram that indicates the manner in which web resource files will be requested, according to an embodiment of the present invention.

FIG. 12 is a SAAP client initialization diagram 1200 that indicates the manner in which web resource files will be requested, according to an embodiment of the present invention. CSS, HTML, and JavaScript may be generated. RNA may also be capable of calling runtime service methods. This allows for populating the raw data payload inside of the generated JavaScript file.

In FIG. 12, the main HTML file includes dynamic resources, static content, dynamic CSS, static and non-static markup, static JavaScript, and main JavaScript. The static content includes CSS and other resource references. The static and non-static markup contains a general structure to hold web parts. A web part is generally a visual representation of a server-side service. The corresponding markup (HTML) is called and loaded in the JavaScript layer. The client may cache the markup to reduce the memory footprint and web traffic. This will often increase the speed of the application. Static JavaScript files are not dynamically generated or selected.

The main (i.e., generated) JavaScript includes links to a cached personal data file, a cached general data file, and a general service scaffolding file. The cached general data file includes small lists of data for drop downs or radio buttons, captions, and labels used in a general context. The main JavaScript also includes a non-static raw data payload that includes data that should not be cached. The main JavaScript may be embedded directly into the page and compressed to reduce the number of round trips and increase the speed with which the page loads. The main JavaScript loads web part files and runs initialization.

Each web part file may include a link to a web part markup (HTML), a link to a web part scaffolding file, and a web part raw data payload. The content of the web part scaffolding file loads any client-side support needed for the respective web part. The content of the web part raw data payload loads data to be used for the given web part instance.

There are three major goals associated with this aspect of the framework in some embodiments:

(1) To provide the HTML, JavaScript, CSS, etc. with the means to represent a given service model and context.

(2) To optimize loading a given set of web resources. It is generally considered a best practice to minimize and bundle like resource files to improve how a resource is loaded. The SAAP pattern balances the needs of a resource load with the performance of the resource reload. By structuring resource packages as general or associated with a given service, this should limit the package sizes to only what is absolutely necessary, and also reduce redundancies in reloads. Caching static data should reduce the number of AJAX calls that are required in some embodiments. Caching should also increase the performance of loading a given resource and improve testability.

(3) To provide a relatively simple and automated interaction with the server side.

Initial RNA Implementation

RNA may include various element commands. The code command in some embodiments represents a relatively simple base methodology to define code not formally defined in any structure. It may also be the core building block of all structured RNA element types. The module command represents a file marker for a given code area. In the case where a module element is nested, the corresponding code type may also be defined in a nested file. The code hlx-product ="@complement[attr-prpl-name]" may indicate what the target name for the file is to be. The code hlx-origin="Origin Project" may indicate what the primary DNA structure is. The code hlx-complement="Complement Project" may indicate what the secondary DNA structure is.

The "import/item" command may represent the code location of a given library. The value attribute may contain the imported namespaces for a given module. The class command may produce the shell of the class definition. When passing an object reference for the given context, such as hlx-bind="@complement", the class command may automatically first write the defined class in the provided structure. The property command may produce the shell of the property definition. When passing an object reference for the given context, such as hlx-bind="@complement", the property command may first automatically write the defined property in the provided structure.

The interface command may produce a shell of the interface definition. When passing an object reference for the given context, such as hlx-bind, "@complement", the interface command may first automatically write the defined interface in the provided structure. The scope command may provide a simple open/close set of curly braces. For instance, the scope operator could be used as a subcomponent for other element types (e.g., class, property, interface, etc.), as well as for custom elements. The attribute command may provide structured support for implementing attributes associated with the current DNA data point context. This list of element commands only represents a partial, non-limiting list of element commands. Additional methods may be added to the Genetic Framework as desired. A developer can also easily extend this set with a custom method.

RNA Flow Control

The hlx-loop element may provide a means to iterate through a PRPL series. The source and complement DNA structures can be bound together with identical query prpl-name(s) in some embodiments. The origin and complement may have diverging controllers and paths in order for this to work. For example, Source Root\My Table\My Field:[children] and Complement Root\My Table\My Field:[children] may both be resolved with the name and query My Table\My Field:[children] in some embodiments. When the user is in the context of My Table, the query @Current-Name\My Field:[children] may be used to obtain records from the relative position.

The hlx-if element may provide a methodology to qualify if an item will be included in a set before the product is created. When the hlx-postpone="true" attribute is set accordingly, in some embodiments, the "if" statement may not execute until after the product has been created. Preforming this operation before the product has been created short circuits the execution. The hlx-else-if and hlx-else elements may be nested inside of the corresponding hlx-if.

The hlx-embed element may act as a macro or placeholder for a given RNA file. The execution may follow the current corresponding context.

```
<Module      hlx-product="@complement[attr-prpl-name]"
             hlx-origin="Origin Project"
             hlx-complement="Complement Project"
             hlx-pre-if="hlx-any:Current-Name:[children]">
   <Class Name="hlx-resolve:complement[attr-prpl-name]">
       <Class Name="Model">
           <hlx-loop query="@Current-Name:[children]">
               <hlx-if expression="Some Query">
                   <Property hlx-bind="@complement" />
               </hlx-if>
           </hlx-loop>
       </Class>
   </Class>
</Module>
```

Polymorphic Relational Path Language (PRPL)

PRPL is a simple path language that identifies a node and its relatedness inside of a given hierarchical tree structure. Generally, PRPL includes a set of tree structures linked with tree structures. PRPL provides a way to request data, and may be used to connect and relate data with disparate data sources. In some embodiments, the data is read only, with no means to update it. Updates may instead be accomplished through standard SQL queries. However, in other embodiments, PRPL may change data.

There are two aspects to modifying data in some embodiments:

(1) The underlying data structure to support data modifications. The PRPL infrastructure may be oriented around the concept of a node. A node typically has attributes and a source (i.e., where the node originated from). When an attribute is targeted for an update, it may be added into a separate "Dirty" attribute container, such as a Dictionary data type. The node itself could be targeted for deletion, or marked as inserted. This approach would allow the changes to be transactional with commits and rollbacks. It should be noted that some data sources would be limited in supporting transactions. This would affect the implementation and behavior. In a closed system, a data writer would typically need to be created to handle the various supported data sources, such as XML, file system folders, text data, or database(s). Compiled and interpreted code or executable components may also be managed, updated, and organized with a PRPL structure. An open system may employ the asynchronous service. See FIG. 21. In the event that the data source is modified for a given node, the node may need to be deleted from the original data source and added to the new data source.

(2) The underlying script to support the equivalent to insert, delete, and update operations. The script may need to support append, prepend, write, overwrite, prewrite, delete, and replace operations. The operation lists may need to be extendable.

PRPL has many uses in some embodiments, including, but not limited to: (1) providing a uniformed query language to be universally resolved for use with external data source components; (2) providing a way to retrieve common support data patterns, such as retrieving a selectable set for the UI (data entry and filters alike); (3) providing common support patterns and storage strategies for use inside of a database; (4) simplifying, identifying, navigating, and executing programmatic components (reflection); (5) providing a robust infrastructure to logically overlay disparate resources—for instance, a PRPL query could resolve an XML document or a .Net method to perform a similar task (DNA, RNA, and SAAP); (6) providing polymorphic behavior, inheritance, and masking patterns with a file structure; (7) providing a means to resolve nodes between differing data sources—a query may be used to navigate through a file structure, identify elements, and result in nodes that represent directories, files, and elements; (8) providing an infrastructure for code generation (DNA and RNA); and (9) providing an intuitive and encapsulated system for resolving security privileges. PRPL may be implemented using the SAAP architecture and be used extensively in SAAP and the Genetic Framework in some embodiments.

For code generation, PRPL can be used to correlate logically between related types. A data model may be related to one or more view models, for instance. A view model may be related to one or more views. This relationship may provide a means to inherit, modify, and operate on each layer of code generation.

Some of the use cases for PRPL include, but are not limited to, UI lists, service navigation, and code generation. UI lists may be used as a common source to select data out of a list. This list may be used for adding, editing, filtering, or reports in some embodiments. In some embodiments, UI lists could be used to enhance performance for other data sources. For example, a database, such as Microsoft SQL Server™, could be extended with better tree support. The list may be extended so specified end users can manage the list. Generally, a database may be employed for data storage.

Service navigation may navigate and resolve server-side method calls. A request may be able to identify the best service, method, and models, with the potential for multiple fallbacks based on various variables and permissions for the current user. Code generation may correlate logically related types. A data model may be related to one or more view models. The view model may be related to one or more views. This relationship provides a means to inherit, modify, and operate on each layer in some embodiments.

Partially related nodes may be delimited by a "/" character, or any other suitable character without deviating from the scope of the invention. The fully related nodes may be denoted by a "~" character, or any other suitable character without deviating from the scope of the invention. Each segment between the "/" character should be unique (excluding overrides, which are discussed later herein). The section between two "/" characters may be considered as a sort of namespace.

In some embodiments, tree data structures are used to create data sets also known as "volumes." Volumes may contain other volumes, and the root volume is referred to herein as the "library." Logical trees may be constructed when querying a given node. How a query is configured, which node is used, and which operator is employed may affect which nodes are included. See FIGS. 14A and 14B. A query in some embodiments may include: (1) multiple starting points for nodes as starting points and arbitrarily determined by the developer; (2) patterns for how to navigate a tree structure also known as iterators (see FIG. 15); (3) filters that qualify whether a given node will be included in given result set based on associated attributes; (4) paging that indicates how many records may be included in a given result set; (5) sorting that indicates the order in which records will be returned, based on the associated attributes; and/or (6) the operators employed to relate subcomponents together (see FIGS. 16-20). A tree can also have gaps in some embodiments. For instance, a given tree path might be described as Alpha→Beta→Gamma. Some or all of these branches might not actually be stored in the database. A resulting query may provide a virtual node where necessary.

Request Type

Initially, there may be two high level request types in some embodiments: data and execution. A data request may return a set of data in a table, XML, JSON, an object format, or any other suitable data format without deviating from the scope of the invention. An execution request may run a corresponding code type. Both the data request type and the execution request type may require a workflow. Each step of either workflow may be run end-to-end in tandem or independently as part of a modified workflow.

Workflow

In some embodiments, the workflow may generally operate as follows. For initial request processing, a request may be made to the system, the request may be parsed, and a controller list may be composed. Request calls may come from client and internal services. By way of non-limiting example, a web client may make a request via JavaScript, a service may make a business, database, or web request, and a SQL database may make a SQL request.

The request may then be parsed to separate and relate the various query components. Requests may be subdivided between quick and full requests. Quick requests may be relatively simple and represented as a single line in a command line. More complex queries may be expressed in a declarative format inside of a markup document (e.g., JSON/XML). For consistency, the system may convert simple requests to a common format that can support both request types.

Not all specifics of the language are included as part of this document in some embodiments. Aliases, variables, and macros may recursively replace the corresponding appropriate parts until all items are resolved. Various components may be represented by aliases. A given component, such as a script, may be represented by a variable using @My Script=My Node[Children]. This could be generalized further to functional behavior, e.g., @My Script=My Node[@My Iterator]. The @My Iterator would need to be resolved before the My Script could be resolved in some embodiments. If the @My Iterator could not be resolved, it may result in an exception.

Safeguards may be put into place to prevent recursion from crashing the system. For instance, a recursive safeguard may come in two forms: (1) there may be a maximum number of iterations allowed, similar to SQL server or a stack trace in .Net; and/or (2) there may be a "breadcrumb" left indicating that resolving a given variable was already attempted in a given context—if variable @A is required to resolve @A, this may result in an exception because recursive macros are not allowed in certain embodiments. A relatively simple request may appear similar to the structure in request 1300 of FIG. 13A. The parsed relatively simple request will conceptually appear similar to parsed values 1310 of FIG. 13B.

To compose the controller node list, a list of queries may be created that relate to the corresponding data set. Controller nodes refer to the relationship of nodes when using the extend left or right operators in some embodiments. This may be based on the controller portion of the query. Consider the instruction:

Alpha~Beta/Gamma~Delta

The result set in this case would be based on the placement of the "/" and "~" characters. In this example, there are four controller nodes:

Alpha
Alpha~Beta
Alpha~Beta/Gamma
Alpha~Beta/Gamma~Delta

This list represents all possible controller nodes in some embodiments. The same query may also be expressed without the namespace portion and yield the same result:

/Gamma~Delta

Once the list is obtained, it may be evaluated for the appropriate privileges. The privileges can either be granted or revoked in some embodiments. A controller node may be evaluated against a privilege type and a primary user (e.g., by user ID). For example, the system may determine a user Ben's Read access for a given set of controller nodes. Passing one or more secondary users as an additional request parameter may provide a mechanism for user impersonation. For example, the system could determine Ben's Read access for a given set of controller nodes while impersonating Tom. The system may provide multiple patterns of impersonation. The end result of privilege evaluation would potentially result in reducing or expanding the size of the result set.

A list of literal queries may then be constructed. The system may review the data sources mentioned in the configuration for PRPL data sources. Generally, the PRPL data sources should be clustered together in a given database for easy of management, but this is not required in all embodiments. The database may be relational, a No SQL database, or any other suitable data store without deviating from the scope of the invention. Initially, there may be two types of tables: a node table and a staging table. A node table is the same as a corresponding controller node found in the controller list. This segmentation convention should typically increase performance and make sets easier to work with and manage.

Not every node needs to have a table associated with it in some embodiments. The staging table may be referenced in every call. The staging table may have a static name with an extra field indicating what the controller node is for a given value. Users may be able to add, edit, or delete items based on permissions and configured policies. Items found in the staging table may take precedence over corresponding fields in a node table.

For the data request type, data queries are run. Each filtering criterion may be applied to each corresponding query result set. For the execution request type, "reflection" may retrieve the method or model and "invoke" may execute the corresponding request.

Consider the Query:

Question~Doubt[self+ancestors]→Answer[children]

Figure 14A:
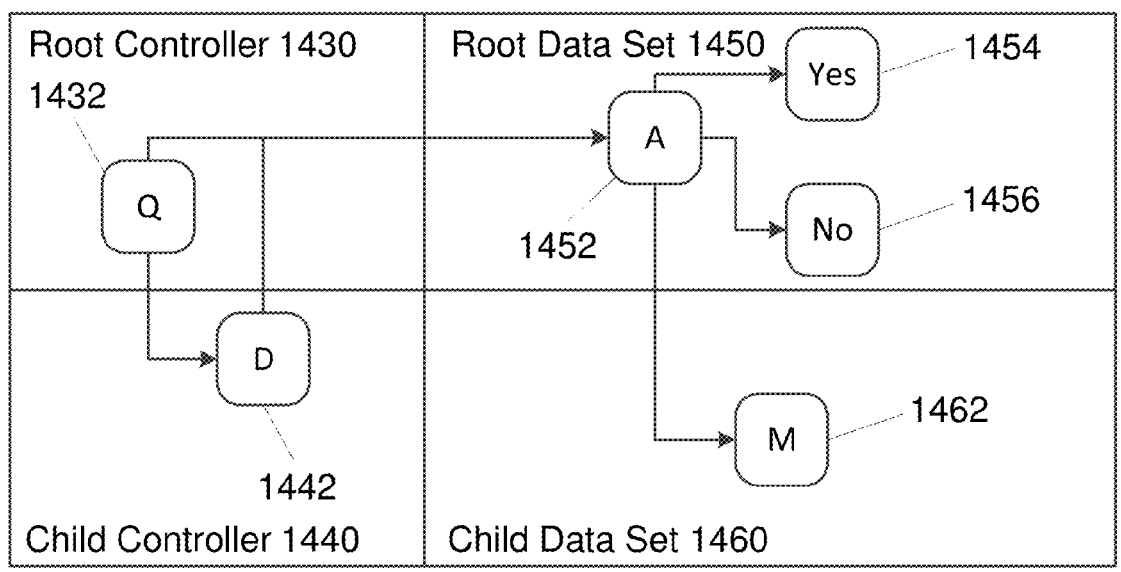
FIGS. 14A-C are PRPL structural diagrams illustrating PRPL structure for a question and answer set of information, according to an embodiment of the present invention.
Figure 14B:
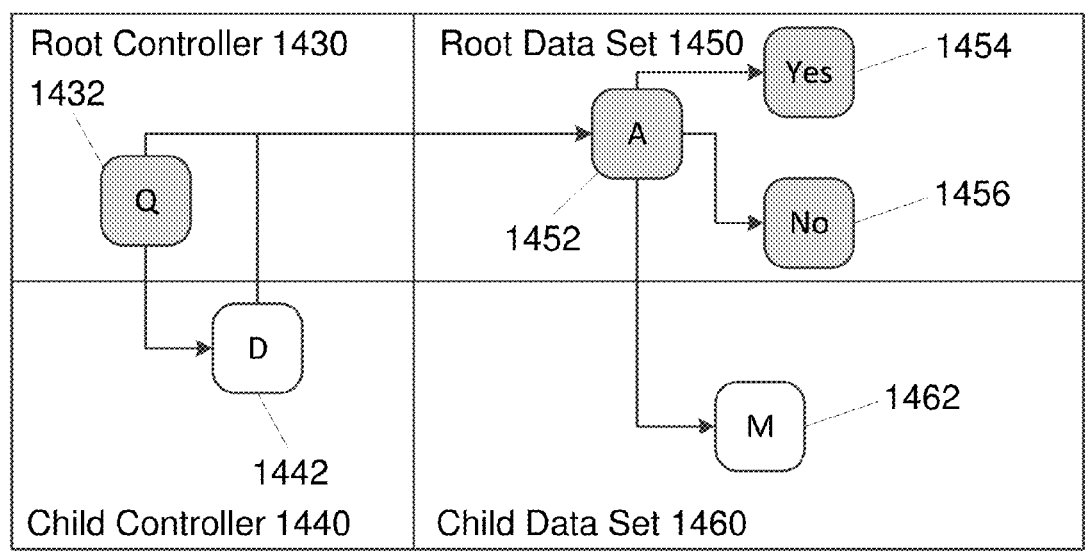
Figure 14C:
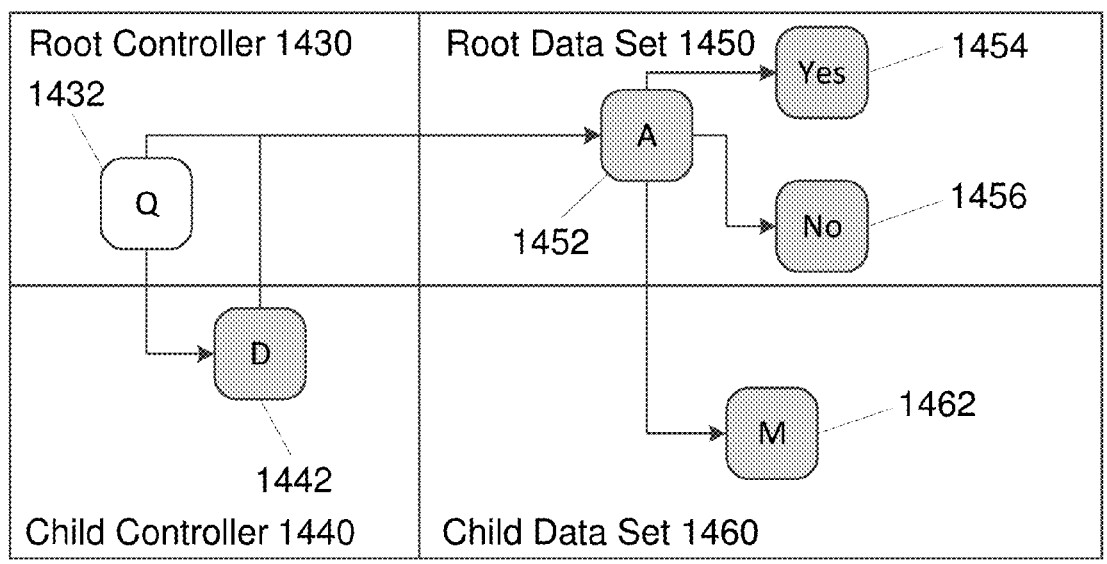
Figure 15:
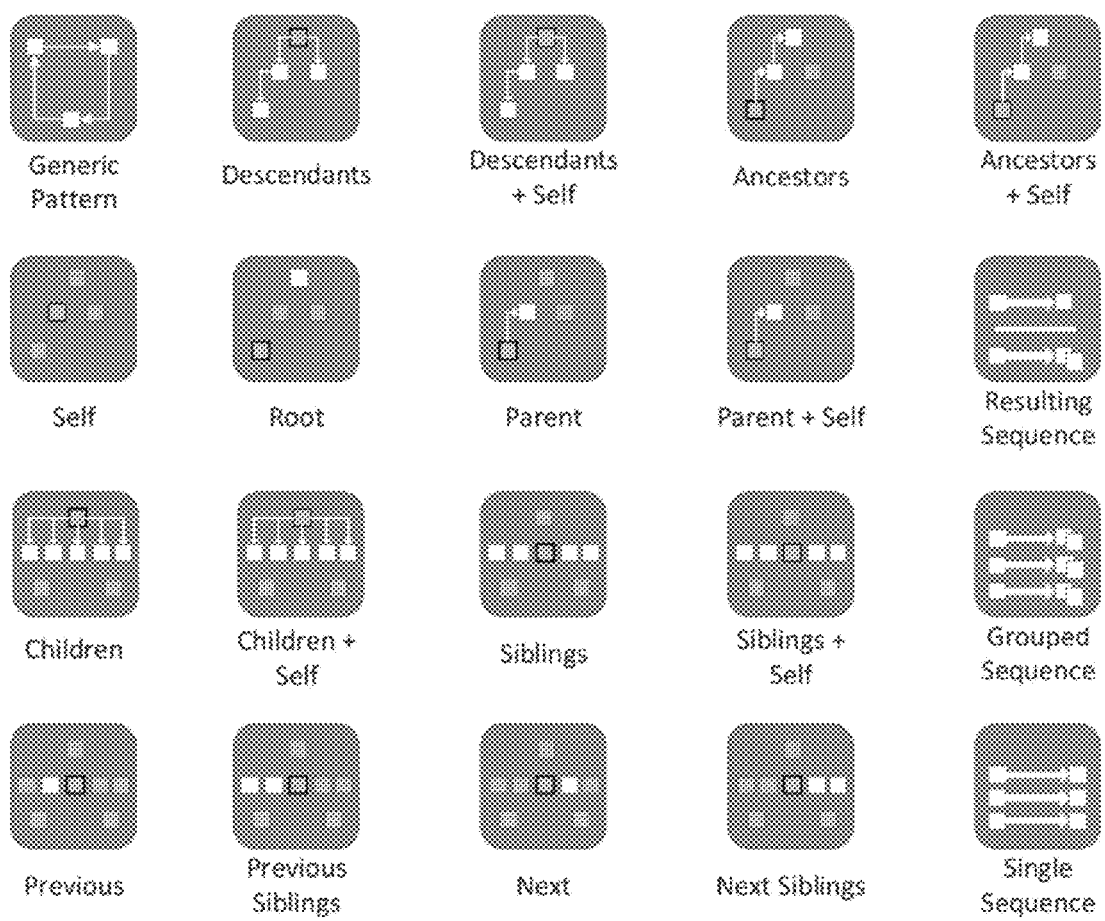
FIG. 15 is a list of core PRPL patterns, according to an embodiment of the present invention.

FIGS. 14A-C are PRPL structural diagrams 1400, 1410, 1420 illustrating PRPL structure for a question and answer set of information, according to an embodiment of the present invention. It should be noted that the example in FIGS. 14A-C, the names of the nodes are arbitrary and are provided by way of example only. Diagrams 1400, 1410, 1420 include a root controller layer 1430, a child controller layer 1440, a root data set layer 1450, and a child data set layer 1460.

The original root node Question 1432 in root controller layer 1430 is associated with the root node Answer 1452 in root data set layer 1450. Answer 1452 has two dependent nodes Yes 1454 and No 1456. Note that node Maybe 1462 is not visible to Question 1432. The visible nodes for Question 1432 are shown as gray nodes in FIG. 14B. The query for returning just the children of Answer 1452 is:

[Question]/Answer[children]

Question node 1432 is extended by a child node Doubt 1442. Doubt node 1442 adds a node Maybe 1462 as a child to Answer 1432. Nodes that are visible to Doubt 1442 are shown as gray nodes in FIG. 14C. The query for this node is:

[Question~Doubt]/Answer[children]

Which nodes are returned for a given request will depend on which node used in the controlling set: Question →(Yes, No) and Question~Doubt→(Yes, No, Maybe). Each node refers to a record of data. An example of what might be returned for a given PRPL request is included in Table 2 below.

TABLE 2

EXAMPLE PRPL DATA RECORDS

| Name: | Path: | Value: | Branch: | Type: | Sort: | Query: |
|---|---|---|---|---|---|---|
| Yes | Answer | 1 | Question | string | 1 | [Question]/Answer[children] |
| No | Answer | 0 | Question | string | 2 | [Question]/Answer[children] |
| Maybe | Answer | 2 | Question~Doubt | string | 3 | [Question~Doubt]/Answer[children] |

Queries can be oriented in various ways. For instance, queries may be oriented via operators, iterators, filters, sorting, and paging.

Syntax

The basic structural component of the PRPL language is the "route" in some embodiments. A route may include a stem and name. The stem includes everything before the last "/" character, and the name includes everything afterwards. Request 1300 of FIG. 13A is a route example illustrating how the route United States~Michigan~Holland~/Park~Beach should be parsed, according to an embodiment of the present invention.

The route is a subcomponent of the query. A query determines what nodes will be provided based on various factors. The pattern describes the relationship of which nodes will be returned. For examples of core patterns in some embodiments, see list of core patterns 1500 of FIG. 15.

A query of: United States~Michigan~Holland/Park~Beach [Parent] would result in the node of States~Michigan~Holland/Park.

One important aspect of many embodiments of PRPL is that they are minimalistic. There may be optional syntactical components. If one of these components is not provided, the meaning may be implied.

Unique to PRPL, these default meanings may be configurable. The queries above are shorthand for the more verbose syntax that other components follow. Request 1310 of FIG. 13B illustrates an example syntax of how the same query can be written more explicitly. The final product may be slightly different in some embodiments. The scripts have been formatted and labeled here for the purpose of illustration.

Variables may be supported by the PRPL language, and may be denoted via a leading "@" character or any other suitable character. The results of the example query may be stored as follows:

@Beaches=States~Michigan~Holland/Park~Beach[Parent]

Variables may resolve to multiple purposes. The purpose may be determined based on the context in which the variable is used. Context may be determined, for example, by query components and subcomponents. If a given variable is used in the wrong context, an exception may result. Variables may also have the ability to have variables themselves, which provides the ability to fashion functions.

Queries may be joined together using operators. The operators may generally correspond with a corresponding operator found in set theory. However, there are some differences in some embodiments. An initial set of target operators 1600 is shown in FIG. 16.

A query may be considered to be the simplest building block. A query is a representation of a symbolic record set. This is similar in nature to algebraic notation. A variable or formula may represent some number or set of numbers. A query may be resolved once it is operated upon. An example script is provided below.

Country[children]

@Country=Country[children]

Figure 17:
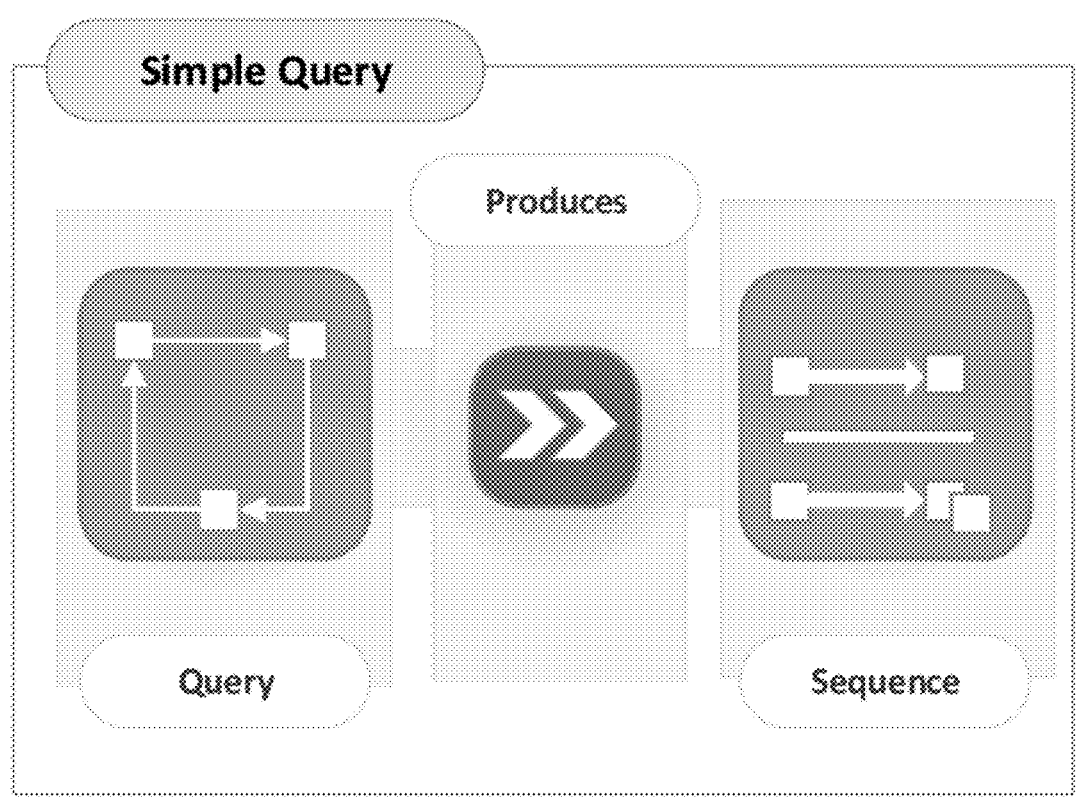
FIG. 17 illustrates general operation of a simple query, according to an embodiment of the present invention.

In this case, some arbitrary query is operated against with the assignment operator and results in a resolved sequence. The resolved sequence is assigned to the variable @Country. General operation 1700 of a simple query is shown in FIG. 17, where the simple query produces a resolved sequence.

Figure 18:
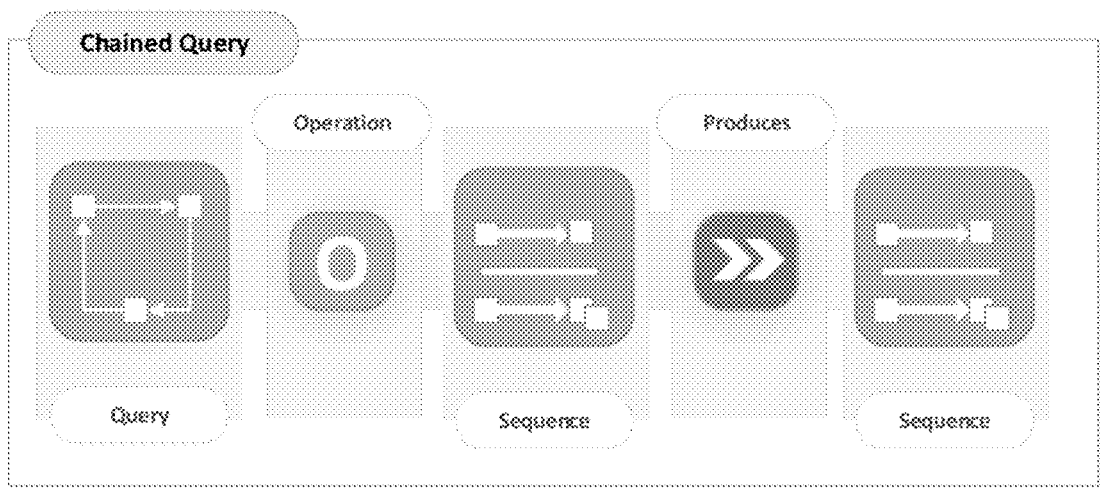
FIG. 18 illustrates general operation of a chained query, according to an embodiment of the present invention.

Chained queries are also possible, and variables may hold operators. General operation 1800 of a chained query is shown in FIG. 18. For instance, consider the sample script:

@AND={+}

@this@AND@that

The query @this is operated on by the operator @AND with the sequence @that.

Figure 19:
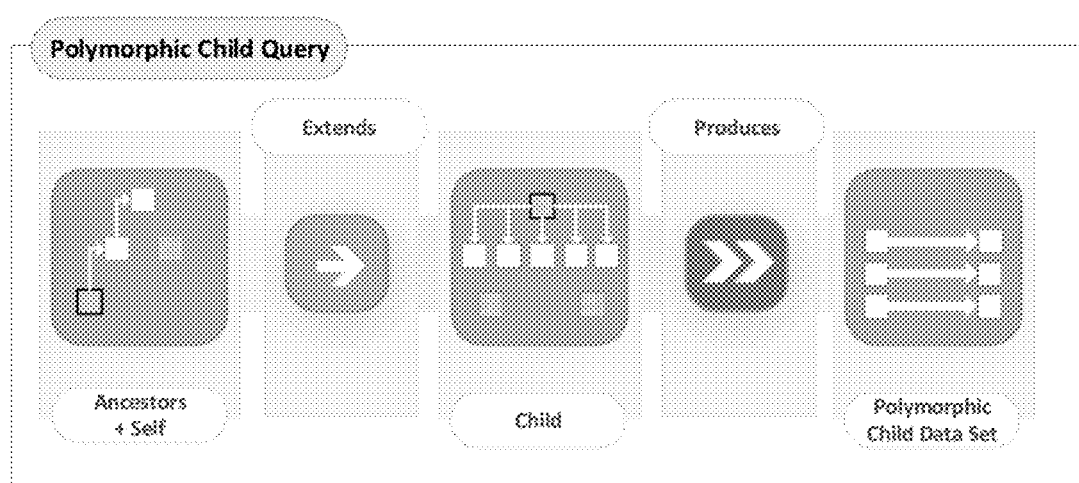
FIG. 19 illustrates general operation of a polymorphic child query, according to an embodiment of the present invention.

Polymorphic child queries are possible in some embodiments, where membership is represented. General operation 1900 of a polymorphic child query is shown in FIG. 19. The script:

@access=Gym~Bronze~Silver~Gold[ancestor+self]→Access/Amenities[children]

represents membership. The Bronze membership is the lowest level of membership. Silver has all of the access of Bronze, plus any of its own. Gold has all of Silver plus any of its own.

Figure 20:
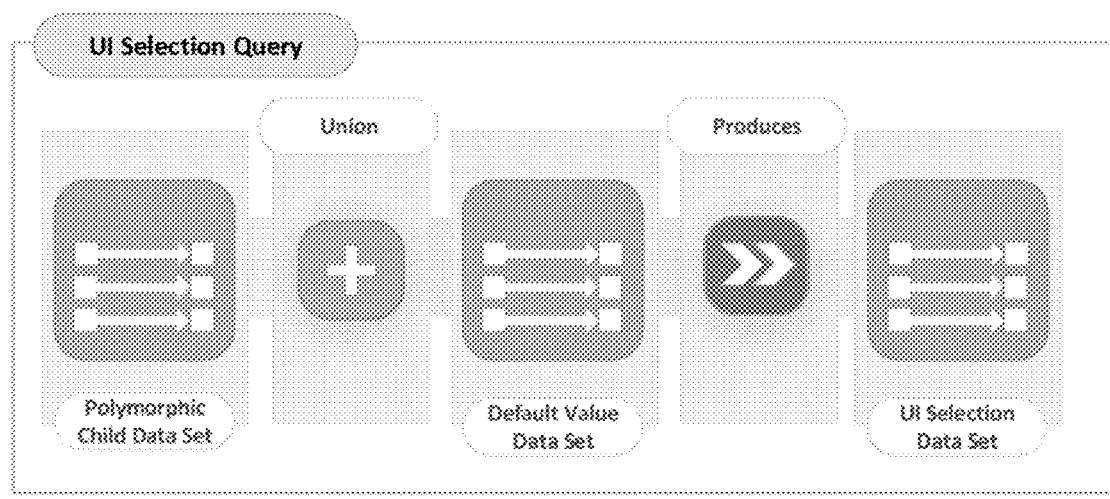
FIG. 20 illustrates general operation of a UI selection query, according to an embodiment of the present invention.

UI selection queries may be performed in some embodiments. General operation 2000 of a UI selection query is shown in FIG. 20. The script:

@statesUI=@states+@[Not Selected]

provides a list @statesUI to be used in the UI. @ statesUI includes a list of all states, including a header node of [Not Selected]. This is a simple way to add an empty node, or multiple nodes, to a given sequence.

Data Source Integration

There are two types of data source integration patterns in some embodiments: open systems and closed systems. An open system can connect and disconnect with any number of data sets. It is asynchronous by nature. The open system works with a pipeline that can adapt to the host technology. This pipeline may be somewhat similar to how database drivers work with object relational mappers (ORM(s)), such as Entity Framework. The open system is optimized to work with approximations of bigger data sets, in contrast to a closed system, which works with the precision of smaller data sets. PRPL pipeline 2100 of an embodiment can be seen in FIG. 21.

Figure 21:
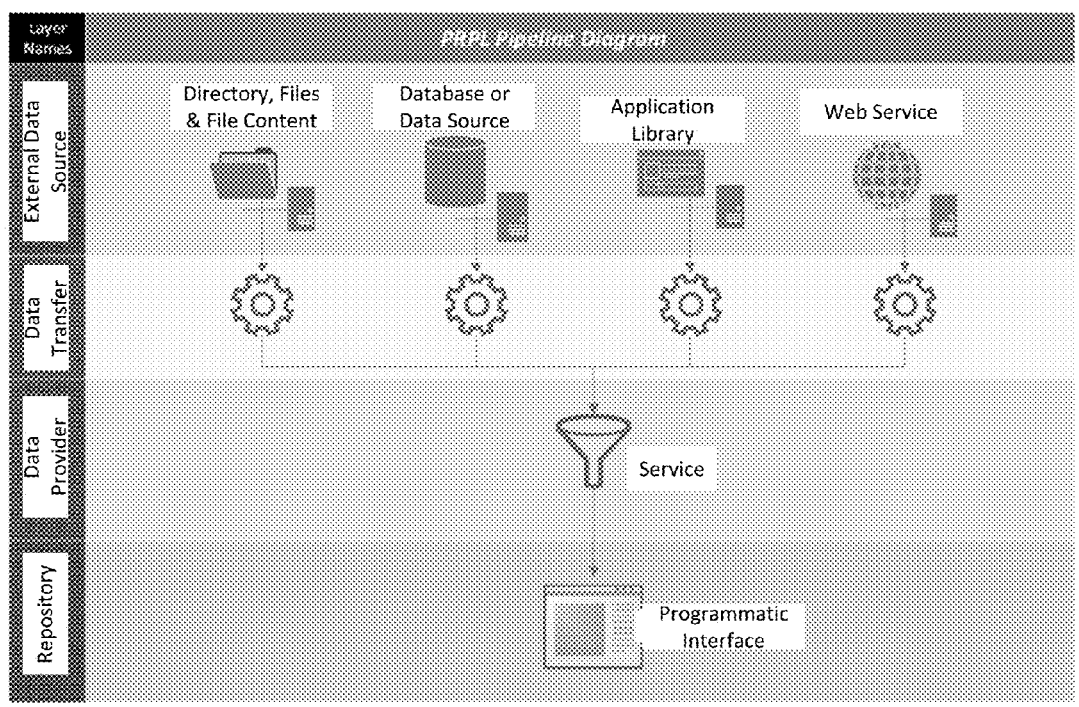
FIG. 21 is an architectural diagram illustrating a PRPL pipeline, according to an embodiment of the present invention.

The general process as illustrated in FIG. 21 is as follows. The programmatic interface takes a request and sends it to the service. The programmatic interface provides metadata required to resolve a given task, such as the relevant set of privileges. In the case where multiple users are represented, the privileges may need to be combined according to the associated strategy.

The service takes the query request, parses the query, and breaks it into corresponding linguistic tokens. The service also sends a serialized version of the linguistic tokens to each of the registered data translators. The data translator reads the organized request and looks at the request to see what the last route value was for the previous request, if there is a previous request. This will be the starting point for the current request. The data translator takes the tokenized query and converts the request to a format that is understandable by the data source. For instance, a file directory may use file paths, databases may use SQL, the application library may use reflection, and a web service may refer to the proxy.

The data source is then interrogated. Using the last query route value as the starting point, the data source will provide an ordered set of matches back to the translator method, not to exceed the page size. The translator interprets the results into something easily understandable by the service. The translator validates that it is at the end of the list or that sufficient results are being provided, taking into account the user privileges.

Figure 22:
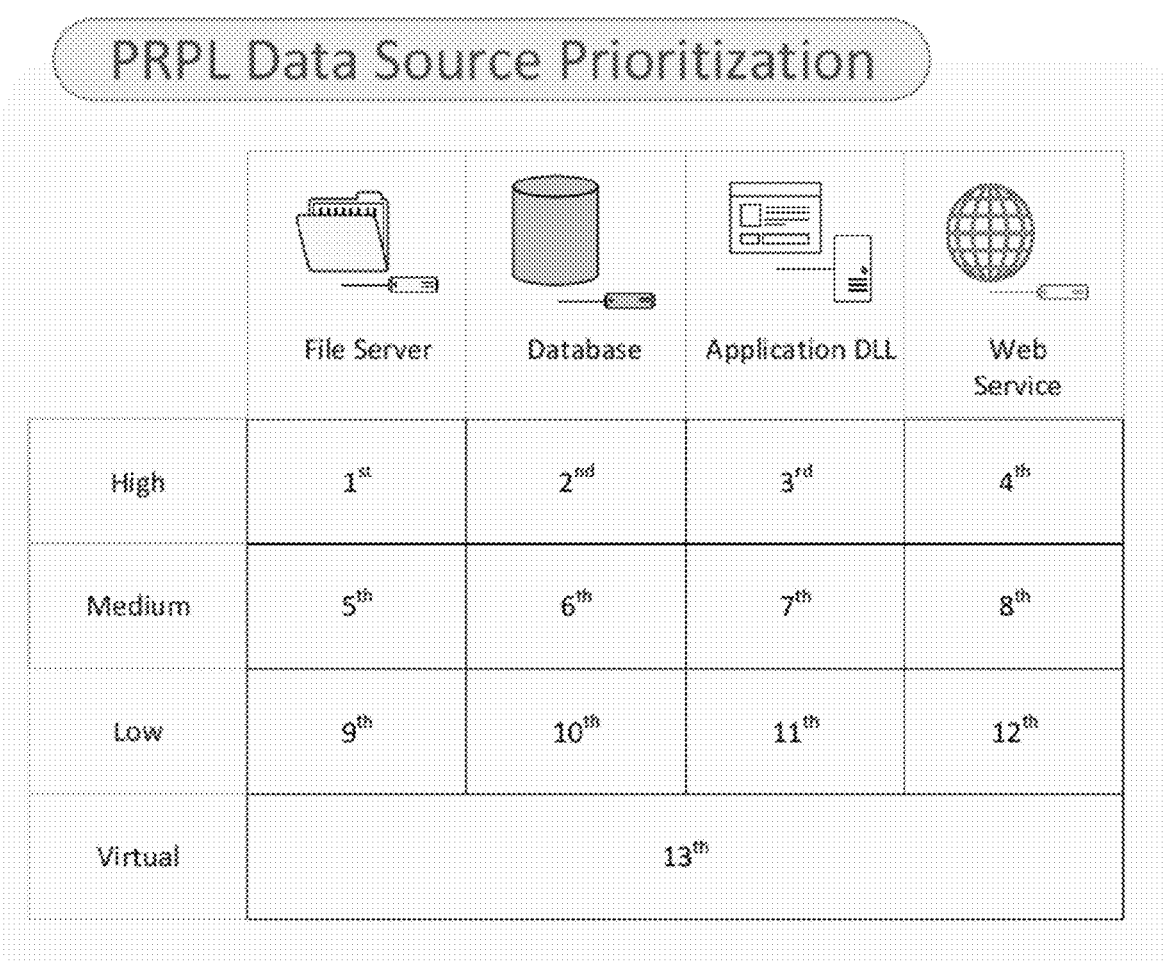
FIG. 22 illustrates PRPL data source prioritization, according to an embodiment of the present invention.
Figure 23:
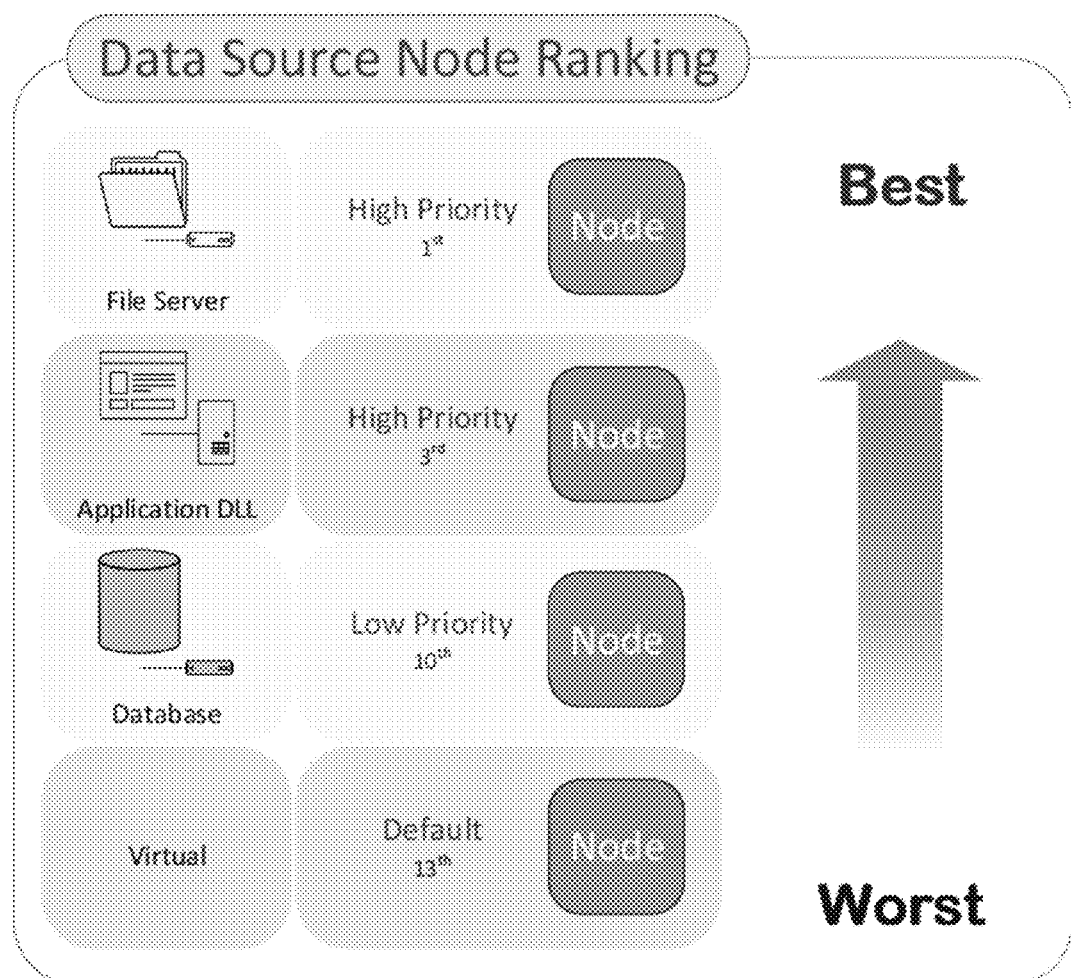
FIG. 23 illustrates data source node ranking, according to an embodiment of the present invention.

The service combines all data and waits for all of the translators that to respond. There will normally be rules on how to handle timeouts to determine what happens in the event of a failure. The service composes a response taking the best data sets. There may be competing nodes representing the same data nodes. When this is the case, the service may prioritize based on a configuration. See FIGS. 22 and 23, which illustrate PRPL data source prioritization 2200 and data source node ranking 2300, respectively, for an example of how these may be resolved in some embodiments. The programmatic interface provides the product to the requesting application.

The closed system uses a single layer framework resolution to combine all of the pieces. It is designed to work with fewer data sources since the data is generally static and in smaller data sets. The closed system may generally work similar to the open system, but perhaps the biggest difference is that all four layers are managed inside of a single framework. The flexibility of the data translator layer is implemented with dynamic operators or other dynamic mechanisms. This allows a closed system to be extended in the service or application in which it is seated. SAAP and the Genetic Framework both may make extensive use of a closed system.

Composition

PRPL is appropriately segmented in many embodiments to maintain is flexibility, testability, and simplicity. It is important to note that while the locale where these process steps occur may differ, or whether process steps happen redundantly may differ between the open and closed system, the processes themselves are conceptually similar. PRPL operation may be as follows in some embodiments.

The query context is called by the requesting object. If a non-structured query is provided, the interpreter is called to convert the PRPL query script into a structured query. Any order changes or augmentations will be part of this process, but this step is skipped if the query is structured.

The query context then generates the sequences, which provide the queried output. There are different types of sequences that can be created—e.g., resolved vs. unresolved, indexed vs. unindexed, etc. Sequence resolution is often dependent on other sequences. When this is the case, the topmost sequence may be resolved first. Tangentially, the dependent sequences are operated on by the operators. See, for example, FIG. 15. Symbolically, an operator will appear to be run once, but depending on the operator and the population of a given sequence, it may be run multiple times.

For instance, consider polymorphic child pattern 2400 of FIG. 24. In this example, the operator has the potential of generating three different sequences. The results of the gamma sequence will be preferred over beta, and the results of beta will be preferred over alpha. The operator relates to set of sequences together, meaning a comparison between a single or enumeration of sequences. An operator can work with linked and unlinked nodes. Linked nodes specifically reference a detached data source. An example of a detached data source is a file directory system referencing an XML file. Another example would be one XML file referencing another. An unlinked resource means that it is attached to a common root node (i.e., A~B~C→[children]). In this case, the same thing may be achieved by iterating through an ancestry and a filter of which parent to reference. This operator requires fewer node iterations and no filter, which is rarely or never cheaper and sometimes significantly more expensive and complex.

In some embodiments, data loaders are used to load portions of data sources or whole data sources into a PRPL data structure. Each data source type may require a data reader. This simplifies how the data reader is interfaced. Finding the ancestors, siblings, or descendants of a given data source may vary considerably. Strategically loading data into an optimized structure may greatly simplify other aspects of the PRPL query process, as well as improve performance.

The iterator is solely concerned with processing the routing pattern, and not with filtering, paging, or sorting in some embodiments (these are handled in different components). There are various different possible search patterns. An example list is found in FIG. 15. This list can easily be expanded or contracted provided the particular application and data source.

The PRPL node may contain the required information of how to fulfill a given request. It may have references to its parent, children, next and previous sibling, volume (and its root), and a link to a child volume (used to link structures together). The PRPL node may be responsible for assigning the identifying PRPL attributes (e.g., name, parent, value, etc.). It may also be responsible for providing the PRPL node attributes. The PRPL node generator does this by providing a special type of method —the iterator (or equivalent), as discussed above. The attribute list includes attributes and other key components of data provided in by the raw data of the data source. This data source provides a façade, generalizing the analysis of corresponding pieces of data for the filter operation to iterate through an otherwise jagged structure, and solely concentrate on including a given PRPL node for a given sequence.

Figure 25:
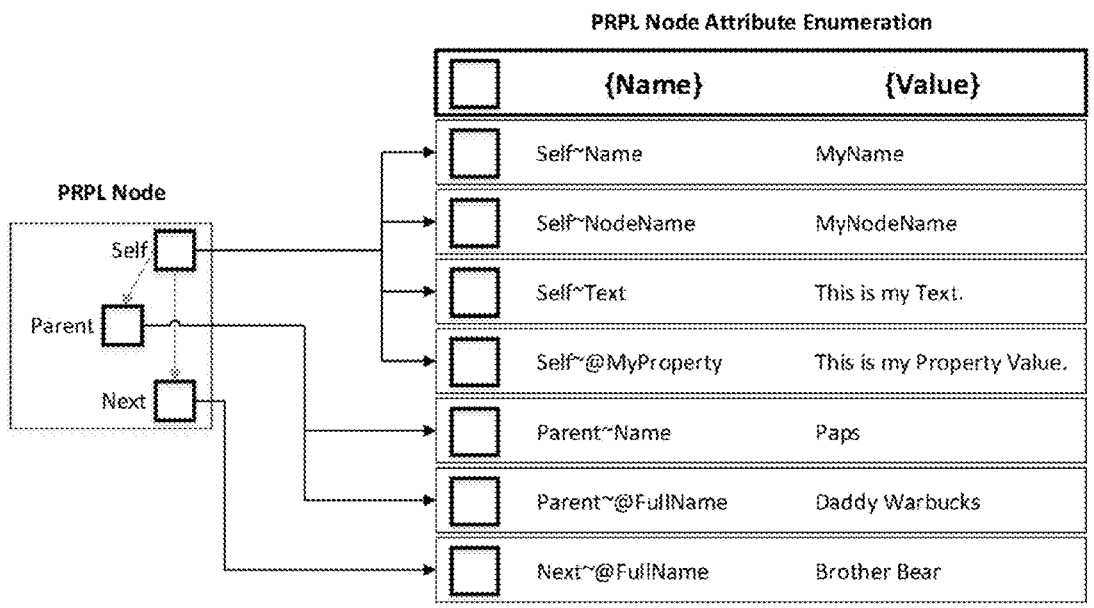
FIG. 25 illustrates PRPL node attribute composition, according to an embodiment of the present invention.

FIG. 25 illustrates PRPL node attribute composition 2500, according to an embodiment of the present invention. The {Name} is composed of the point of origin (Self refers to the current node, Parent the parent node, etc.), delimited by a tilde. Attributes are denoted with a "#" symbol. Property data is denoted with a "$" symbol.

The filter process is focused on determining whether a given PRPL node will be included in a given set. A filter is made up of a series of criteria that need to be met in order for a given record to be included. See PRPL node attribute criteria composition 2600 of FIG. 26. The set of criteria is compared against the set of PRPL node attributes.

The {Name} is a regular expression corresponding with the PRPL node attribute {Name}. The {Value} is also by default a regular expression. Another field could be added called Value Script type, for example, that would change the behavior of the {Value}. For example, if an attribute is needs to treat the {Value} as an integer, it could qualify the integer, indicating that the corresponding value must be within a given range. For instance, the Value Script for mandate that a file size must be larger than zero but smaller than 10,000 bytes. However, any size may be used without deviating from the scope of the invention.

{Is Match} is a true or false Boolean field. It indicates what the result of the {Value} evaluation should be if the {Name} field is met. {Match Group} indicates how a given group should be matched. If the value is a *, then it must be met in order for the record to be kept. One or more criteria must be met for records with a {Match Group} of a corresponding name (which is different from a * value). Security may also be applied at this time, which is discussed in more detail below.

The order process determines how a given sequence will be sorted. PRPL nodes can be sorted by their PRPL name or any other PRPL node attribute. The paging process is the last process that occurs in the processing of a sequence. It also indicates what the starting point should be when a starting specific starting point is provided. In an open system, where the number is not known and is volatile, the starting point refers a node reference. Anything on or after that reference is included. The open system will provide the last PPRL reference to indicate the next starting point. In a closed system, where all the nodes are known and static, the starting point refers to a numerical reference. The closed system will indicate what the last numerical index is to indicate where to start up again.

Security

Security is an important part of the PRPL framework in some embodiments. PRPL credentials can be stored in just about any kind of data source, and can be optimized for a variety of problem sets. PRPL credentials are themselves PRPL records. A given privilege (the PRPL security component) will refer to a route, a pattern (see FIG. 15), or a permission type, such as Read, Deny Read, or Block Read.

The security methodology of some embodiments is extremely flexible. It can be made to model how security behaves with other data sources. This is extremely beneficial for web applications that need to implement impersonation. Implementing impersonation will increase a web application's testability and supportability.

In order to resolve privileges, the following steps may be carried out: (1) a list of all of the principals is obtained; (2) all privileges are provided for each principal —the privileges may be stored alphabetically, so they are easily indexed for performance; (3) Each privilege is compared to the provided query requests to see if they are relevant—the basic rule is that if a query route starts like the privilege route or the other way around, it is a relevant privilege—indexing may be used to short-circuit this process and increase performance; and (4) the kept privileges for each user are compared to the other users, one at a time—this methodology can be customized, but there are three basic patterns: grow, shrink, and replace.

In a grow pattern, permissions can be extended so the user access can only grow or remain constant between users. If someone has access to a given node, the query has access. In a shrink pattern, permissions can be contracted so the user access can only shrink or remain constant between users. If someone is denied access, the query is denied access. In a replace pattern, permissions can be substituted from one user to another. This means that the current user can see identical permissions of another user. This is useful for testing how permissions behave between different users without having to know that principal's password.

Figure 27:
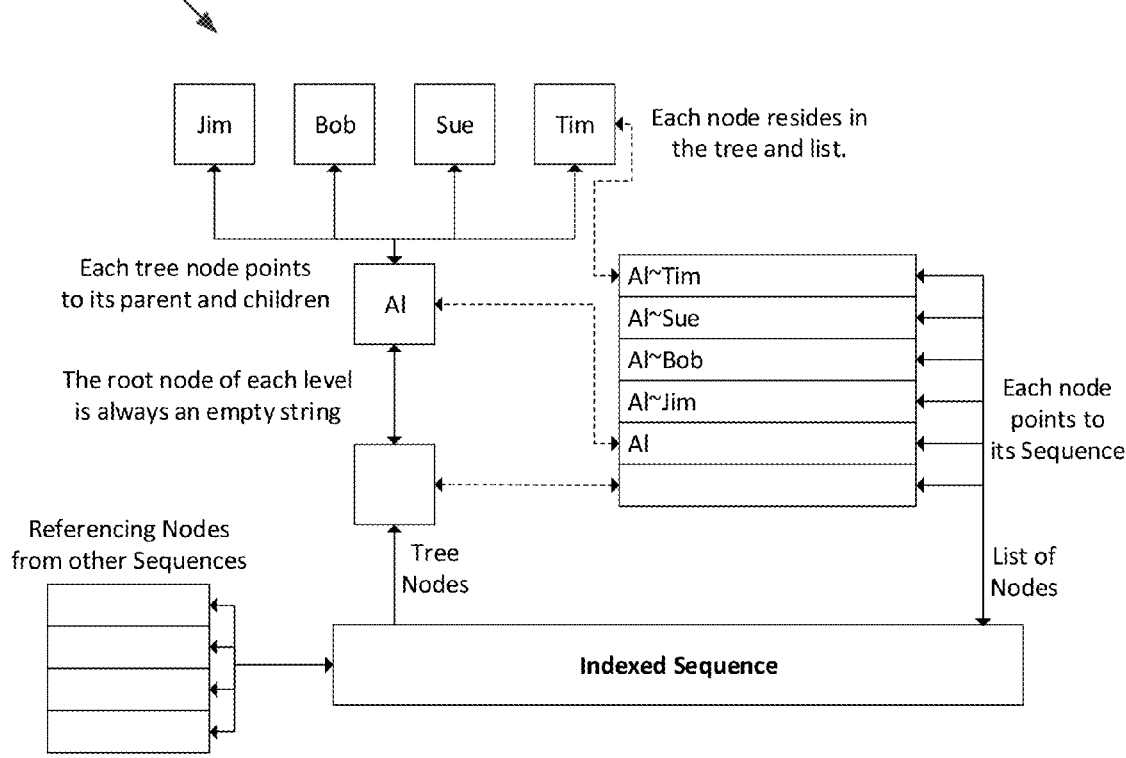
FIG. 27 is a tree diagram illustrating a tree node structure, according to an embodiment of the present invention.
Figure 28:
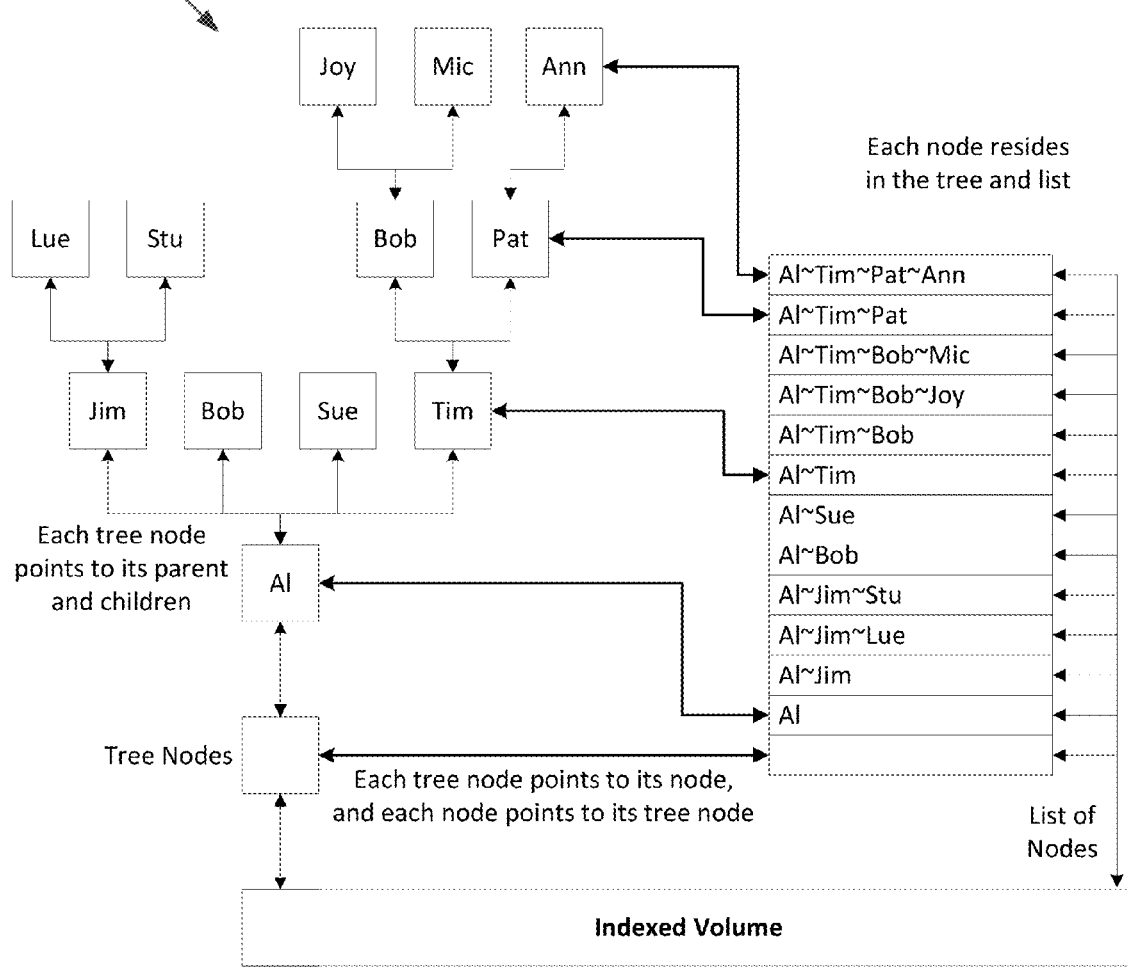
FIG. 28 is a tree diagram illustrating another tree node structure, according to an embodiment of the present invention.

Tree diagrams 2700 and 2800 of FIGS. 27 and 28 illustrate tree node structures, according to an embodiment of the present invention. FIGS. 27 and 28 show the storage structure of PRPL in an embodiment, and more specifically, the volume object model. The root volume is the library. The volume contains a link to: (1) the root node, which is linked to the other nodes in that volume as a tree; (2) a list of nodes that is ordered by the route alphabetically; and (3) a list of referencing nodes from other parent volumes.

A given route should be unique per list of nodes per sequence. Consequently, a tree node should have a unique name as well. Nodes and tree nodes should be maintained in an ascending alphabetical order. This method of indexing generally increases performance. Optimally, data should be inserted into a given sequence in an alphabetically ascending order.

Root nodes provide a node value of a blank string. A root node is at the base of a tree or at the beginning portion of a path with a "/". This resolves problems with dependences and uniqueness. Consider the following paths:

Alpha~Beta
Alpha/Beta

Both are valid, and both result in an Alpha ancestor and a Beta. Adding a blank between Alpha and Beta in the "/" scenario means that there is a unique path. It also means that Beta is not a sibling to another Beta node. This ambiguity is resolved without complexity. Additionally, having a common root node means that the nested root node is more easily severable into a separate indexed sequence. This structure readily lends itself to fast navigation using a combination of the list structure and the tree structure.

Reflection

PRPL provides a relatively simple way to be able to navigate through reflection as a universal protocol in some embodiments. PRPL may also be designed to go hand-in-hand with SAAP. The SAAP pattern itself is described in greater detail below. The pattern in some embodiments is optimized for creating workflows, communicates in a client-server relationship (such as a browser-web server), and is optimized for testability.

SAAP centers on a full decoupling of data and actions. Data is represented in model object types. In some embodiments, a metadata (or flow) model is used for managing routing, tracking history, etc. Actions are represented in service object types. The context object types contain references to models and actions (via delegates).

Services may be intended to act as self-contained programs. SAAP may make extensive use of nested types. General models may be stored in a general space. Service-specific models, contexts, and server/method definitions may be nested inside of the principal service class. The public facing methods may possess two parameters in some embodiments: data and metadata variables. Model and method definitions may be identified from the PRPL request described in the metadata.

Figure 29:
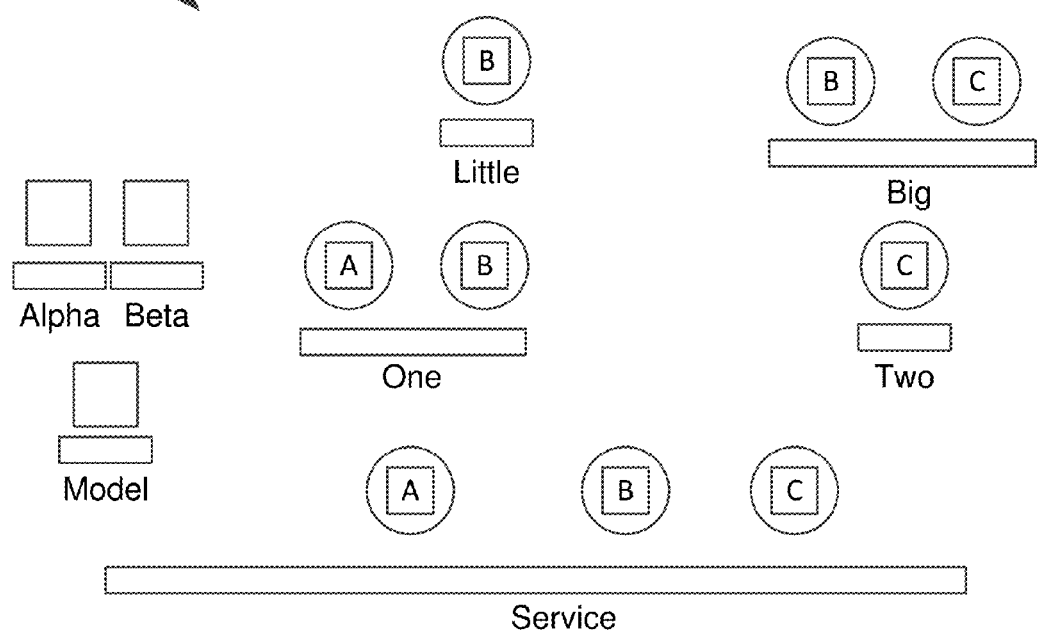
FIG. 29 illustrates an example service and model, according to an embodiment of the present invention.

FIG. 29 illustrates an example 2900 of a service and model, according to an embodiment of the present invention. The rectangles represent classes, the boxes represent models, the circles represent methods, the squares in the circles represent parameters corresponding to a given model type, and the letter in the box refers to the method name. The service is the lowest level class and is publicly facing. The models are also publicly accessible. Nested service classes should be considered inaccessible to direct outside calls.

Services may be related one another by using objects defined in their respective container objects. For example, a context from a host service may be assigned a guest context reference. A relatively simple example of common guest services would be a file folder service. If the file folder context is assigned to a domain context, the two services are now related. If the host service were to be used in testing, the file folder context methods could be overloaded with substitute methods to simulate a folder read or write.

To identify the method C in the class Big, the following query would be requested:

Controller Query: /Service~Two~Big
Data Query: /Service~C

To identify the method B in the class Little, the following query would be requested:

Controller Query: /Service~One~Little
Data Query: /Service~B

Since PRPL is discrete in nature in some embodiments, not every method needs to be represented on every branch. Note that there is no implementation of method B in class Two. If this is called, the developer should make a determination of what failover would happen. For instance, an exception may be thrown or a fallback method may be selected. Under this logic, if the following query were to be requested:

Controller Query: /Service~Two
Data Query: /Service~B method B of Service may be retrieved or an exception may be thrown.

To access the base model, the following query would be requested:

Controller Query: /Service~Model
Data Query: /Data/Model

To access the base model, the following query would be requested:

Controller Query: /Service~Model~Query
Data Query: /Data/Model

It should be noted that often times in the case of a web client request, the data type of the model needs to be determined upon reaching the service. If the objective is to dynamically determine the model type, this can be resolved by identifying the service method. The method signature may provide this information to the web layer and can assist in initializing the model.

Invoke

When the types are identified, reflective invocation can take place. Methods can use the "Invoke" command, along with the appropriate parameter arrays for proper execution in some embodiments. The model may be created and have the serialized content bound thereto. This would provide an opportunity to greatly reduce the size of the web layer for this example.

Service Area Architecture Pattern (SAAP)

SAAP provides a more robust methodology for workflow processes. It reduces the time of development, increases extensibility and testability, is fluid yet structured, and improves overall project organization in some embodiments. SAAP has the ability to extend and redefine service logic in successive layers and in ways not before possible. SAAP is powerful due, in part, to its simplicity and expressiveness—it is readable and writable for machines and humans alike.

The core concept of SAAP is to organize system and business layers of service descriptions. Each service layer has a uniform manner of construction and behavior in some embodiments. This starts with the container object type. The container object type provides a point of reference (i.e., an anchor point) for the server, as well as a relatively simple means to indicate what object types belong to a given service layer.

The context object type is the nucleus of a service. It provides a direct and explicit link for how the data and the behavior relate. A context can be redefined or reused between each successive generation. The actual method definitions may be in a dedicated location. The definition class and methods are static in some embodiments, and thus guaranteed to be stateless. The data may be stored in a relatively simple hierarchy package structure called a model. A context is associated with no more than one model in some embodiments. Structuring the service in this way provides a relatively simple way to reconstruct conditions, greatly streamlining testing and development.

Any subprogram can be partially or completely extended and redefined in some embodiments. Services may be constructed with generalized assumptions of behavior, which can be overridden in a subsequent layer. This type of behavior is similar to polymorphism, which is an object oriented programming concept that has existed for decades. However, the polymorphic methodology used herein significantly differs from conventional polymorphism. Conventional polymorphism is two dimensional, whereas contextual polymorphism in some embodiments is three dimensional or more, simultaneously spanning multiple class types.

Traditional polymorphism cannot span multiple classes simultaneously, and inheritance takes place sequentially in tandem. This is two dimensional. There are good reasons not to do inherit from multiple classes. For instance, there can be conflicts and seemingly unpredictable results.

The SAAP form of inheritance in some embodiments, however, can span multiple classes simultaneously in a fluid and organized manner. There is a clear order of precedence (e.g., PRPL) in which methods are resolved. The definition class can be used as a point of inheritance when assigning a method definition. Adding layers inside of the definition adds more dimensions.

Composition

The SAAP framework is made up of seven common component or object types in some embodiments: container, context, model, definition, flow, request, and response. These seven components provide predictability with a specific kind of behavior. This consistency results in intuitive workflows for the programmer to manage. Moreover, having a consistent pattern provides a uniform way for the various services to communicate.

Figure 30:
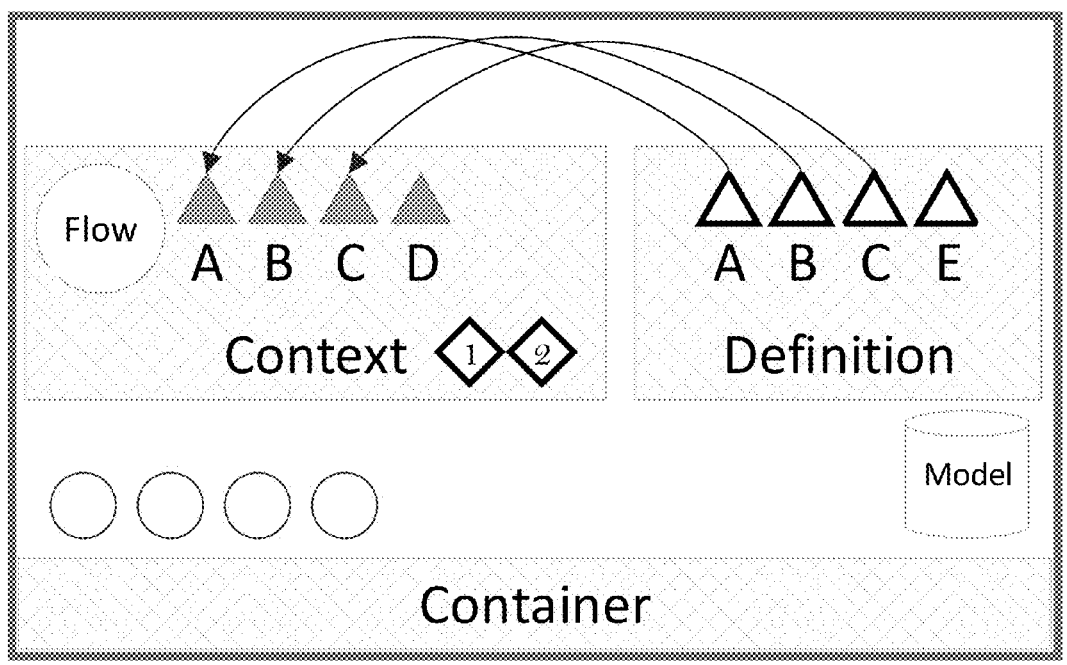
FIG. 30 illustrates a container, according to an embodiment of the present invention.

The container static object type encapsulates (or contains) the definition of the other object types. See container 3000 of FIG. 30. Solid triangles A, B, C, D on the left are delegates or method references, which are typically defined in the "definition" class. Hollow triangles A, B, C, E on the right are method definitions. Diamonds 1, 2 are nested context. The circles extend methods defined at the root container level.

This provides a basic and explicit way to describe how the other object types are defined. The container type can also expose shortcuts for common methods to be defined using class extensions (when implemented in .Net, for example). The class extensions are generally associated with a specific context or interface.

Figure 31:
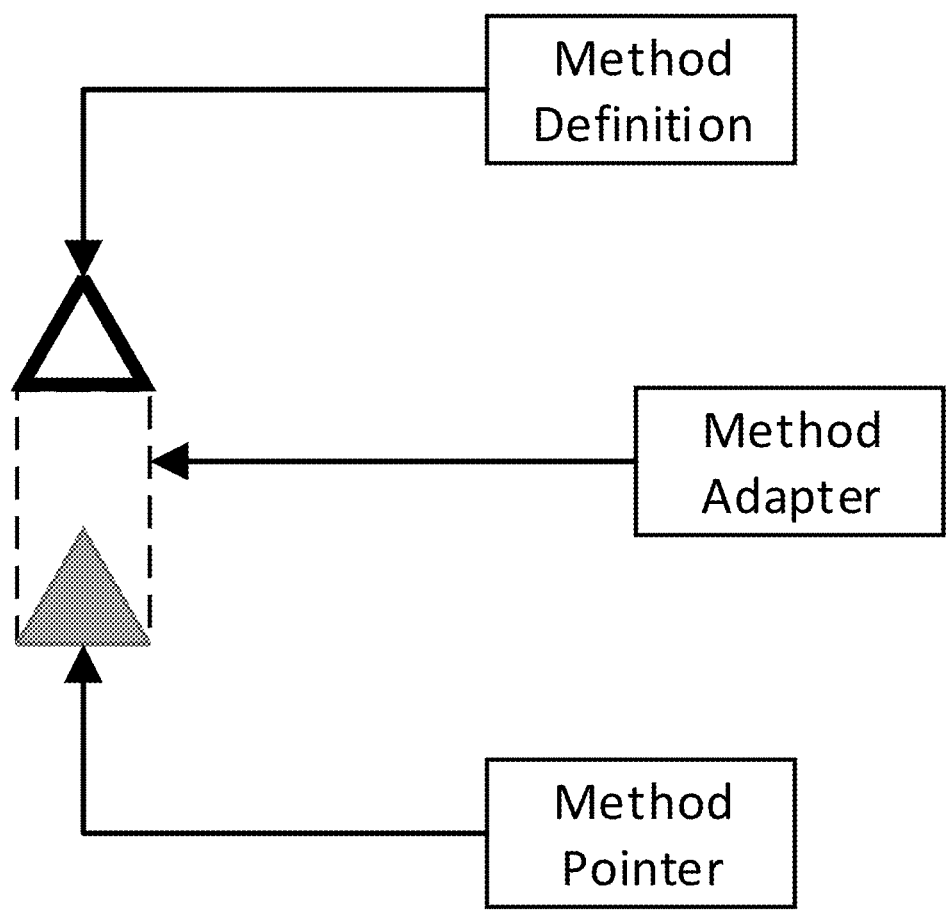
FIG. 31 illustrates a method adapter, according to an embodiment of the present invention.

The context is a non-static object type that provides references to anything that has state, such as flow methods, method pointers (the triangles), and references to contexts of other services. The data resides in the container's model. It is decoupled from, but tightly correlated with, the corresponding context. See method adapter 3100 of FIG. 31. Dynamic operators can be introduced to provide advanced support for workflow patterns.

Adapters can be added to aid in type conversion that the language cannot perform itself. These adapters may also be used in testing to track the path of execution of a given sequence of method calls (also known as tracing). However, the method names A, B, C, D in FIG. 30 may be replaced with friendlier, more descriptive names, such as Save, Update, Add, or GetData.

Figure 32:
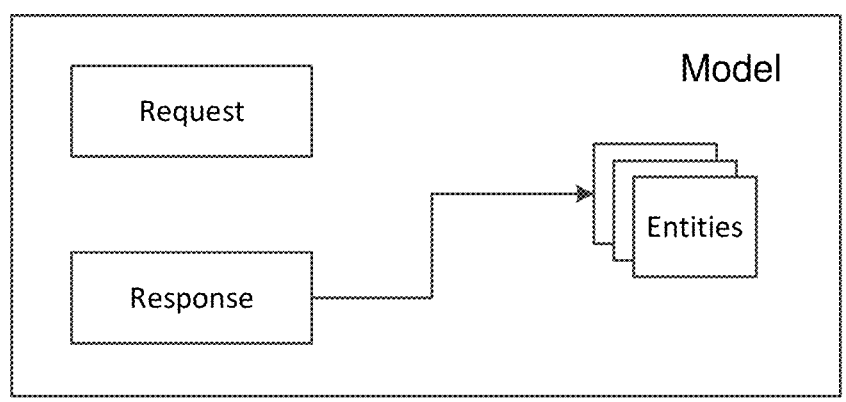
FIG. 32 illustrates a model, according to an embodiment of the present invention.

The model is a non-static object type that holds fields that contain other data objects along with primitives, such as dates, numbers, bytes, strings, and arrays. A model can often be segmented into two parts: a request and a response. See model 3200 of FIG. 32. The request contains data from the client and provides a set of data necessary to perform a given operation. The response provides an output set of data for a given operation to return to the client.

The model can be extended and continue to use the current branch of logic using contextual polymorphism. The context can refer directly to this new model with subsequent components. The method definitions can, in turn, refer to the new model using a strongly typed context without having to typecast the parameters from within a method definition. The framework will manage the type mismatch as long as it meets the appropriate constraints. From a technical standpoint, this would typically be done with generic constraints.

The definition is a static object type that contains a set of static method definitions to be assigned to the context method pointers by the flow object. The definition methods are divided into two groups: primary and secondary. Primary definition methods can be called with a single parameter of the context object. Secondary definition methods consist of all other methods that do not conform to the primary signature. In the case of asynchronous calls, multiple parameters may be required with a handle to the variable being operated on in parallel.

Figure 33:
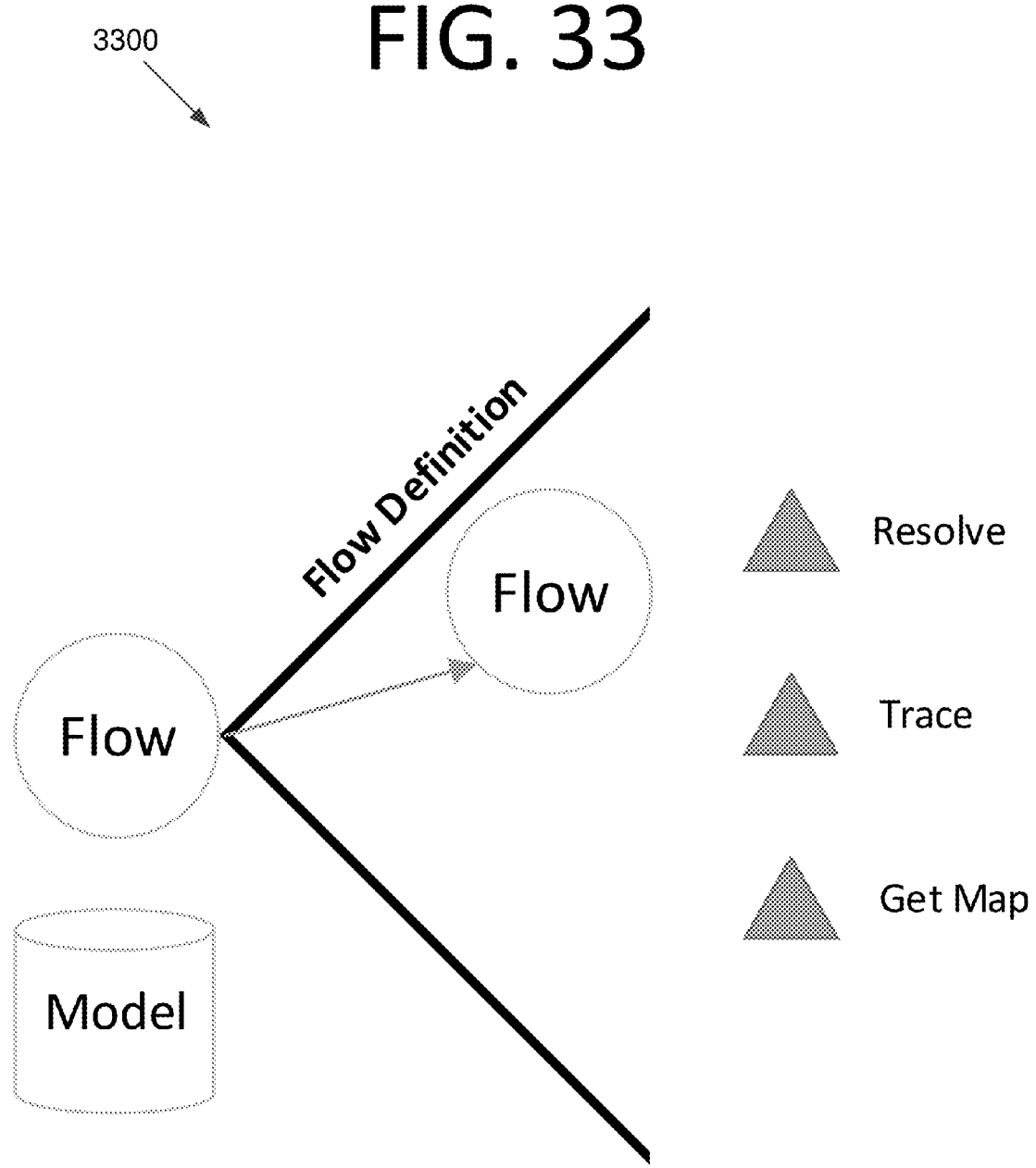
FIG. 33 illustrates a flow, according to an embodiment of the present invention.

The flow is a non-static object type that is designed to assign the context method pointers with the appropriate definition. The flow is itself a service, responsible for managing and monitoring calls. An example of a flow is illustrated in flow 3300 of FIG. 33. The flow object determines the point of origin, determines how the request of the host service resolution should be handled, and provides tracing and debugging information. The flow includes a reference to itself, and core behavior can be overwritten or replaced entirely.

The model is the box or container for the data that is to be operated upon. Separating the model from functionality provides portability, flexibility, and testability. Resolve accepts a given type parameter and traces through the type mapping to obtain an instance of an object or a method of the specified type. Trace records the activities of a given object. Get map provides a list of instructions compiled from the assembly code to produce a map used by the resolution method.

The flow has a number of operations it can perform. For instance, it can identify and assign the context pointer with the appropriate definition. It can also create instances of other context types. This allows injecting outside service logic inside of a given method definition, without employing $3^{rd}$ party injection frameworks. The flow can also dynamically call a sequence of one or more method definitions not explicitly defined in the context object type and provide a means to hot swap multiple methods from static method definitions or other method pointers.

Container Resolution

The service portion of the SAAP framework is made up of multiple layers. The various layers work in tandem, providing a space to successively define a service. Services can be defined as part of the general service, a primary service, a complement to another also known as a secondary service, or fragmented inside of a given service. With these tools, a service definition can be appropriately layered and redefined.

The final configuration of a given context may account for four major factors in some embodiments: (1) how the sequence of the service layer containers is described and what the method definitions are that are provided or omitted; (2) what permissions access a current set of users or principals have for a given method definition (see the PRPL disclosure above); (3) what the resolution of the provided PRPL script is (see the PRPL disclosure above); and (4) what the entry point is for the initial context (for instance, model-view-controller (MVC) generally calls surface level services from a controller that are defined in a web library (the calling web library is the entry level). Calls to nested services would reference the same flow context, and therefore would not be considered an entry point.

There are a number of deviations or strategies on how to resolve service tokens, but the overall result remains the same. The deviations or strategies are a forest in some embodiments, with trees of trees of trees. This is the basic premise upon which PRPL has been designed in some embodiments. PRPL may be an essential part in determining how service components are resolved. There are essentially three tree strata in some embodiments (although this could be expended to support more). See FIG. 11 and the associated discussion above.

The first service layer is the project, which is often referred to as an assembly. An assembly, when compiled into something usable by the computing system, is typically a DLL. A DLL has a base identifier name provided by the language. A general service is located in the root of each library that maps the native identifier with an appropriate and corresponding PRPL name in some embodiments.

The second service layer includes the container objects, which are the building blocks of a service. The route of the second layer includes the namespace of the service container, minus any redundancy of the first service layer. Class attributes can be used to manually assign the PRPL route in some embodiments. The third service layer includes the nested layer inside the container objects. The names of the nested layer inside of a container object consist of the identifier structure inside the container object. Again, class attributes can be used to manually assign the PRPL route.

Figure 34:
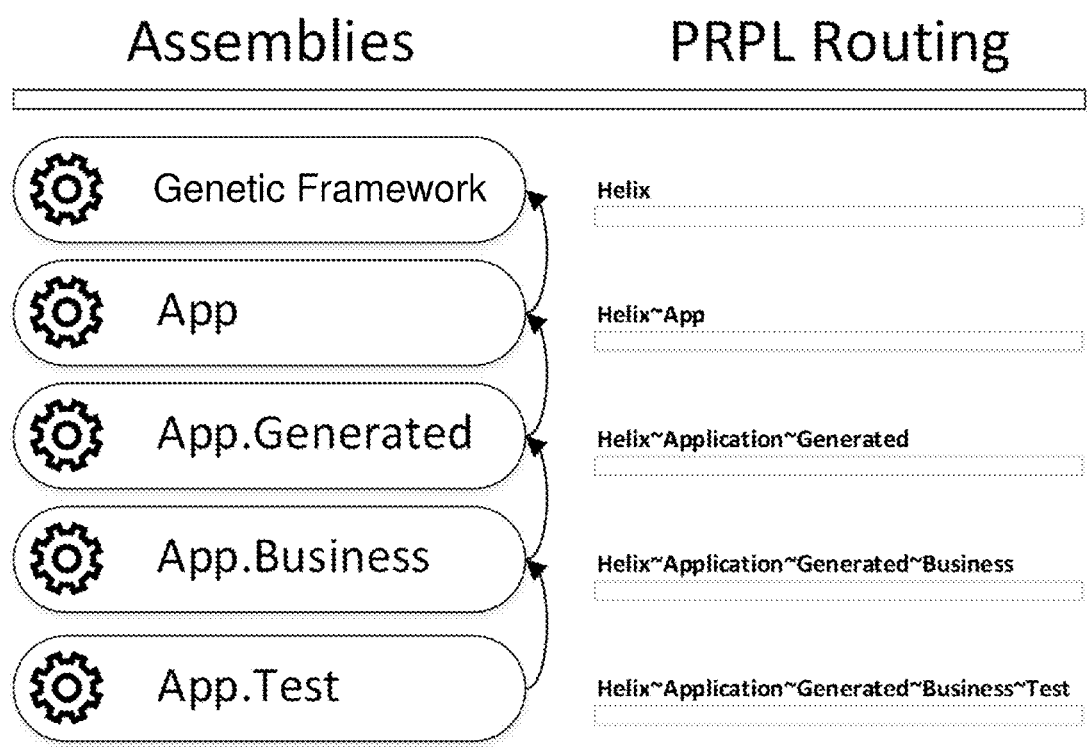
FIG. 34 is an example structure of a web application, according to an embodiment of the present invention.

An example structure 3400 of a web application is shown in FIG. 34. Example structure 3400 includes the assembly name and the corresponding PRPL route. The PRPL route is defined and mapped in the general service space, which is in a common place (e.g., the root of each assembly). The Genetic Framework layer acts as a foundation for a given application. The App layer represents a high level framework or base for a given application. The Generated layer represents generated code. The Generated layer is meant to be entirely defined through the automated genetic process. The Generated layer, however, is human readable. It can be modified in order to prototype how code should be generated. Any changes made in the Generated layer will not persist after code has been generated.

The Business layer provides a space to provide enhancements to the Generated layer. This code would not be practical to generate. The dynamic service method resolution can work to replace much of the functionality performed by the Microsoft™ MVC framework, for example. This methodology can convert JSON content, de-serialize it into a model, and call the corresponding service method. A fully integrated solution would provide a more testable, flexible, and sophisticated solution. The need to write code to manage routing and controller functionality is greatly reduced.

The Test layer represents a programmatic way of testing the application in order to validate that code is performing as expected. The testing is greatly enhanced using SAAP. Most of the structural work is defined in the bottom layers. Every successive layer generally requires fewer and fewer structural changes. The SAAP framework makes it possible to override methods in some embodiments. The ability to override methods is critical to isolating the functional components of an application in some embodiments.

Contextual Polymorphism

Polymorphism is a fundamental part of object oriented programming. An object type can be modified and extended into a new class type. Classic polymorphism refers to a programming language's ability to process objects differently depending on their data type or class (i.e., the ability to redefine methods for derived classes). One of the limitations of traditional polymorphism is that it is limited in how it can be applied. For instance, class structures cannot be effectively combined to work in concert with one another. In contextual polymorphism, however, polymorphism works in concert between multiple class types, and methods need not merely be redefined. Having this ability greatly expands flexibility and simplifies testing. Fewer lines are required to express an idea in code, reducing the chances for errors to be introduced. Simplifying code makes it easier for a programmer to detect and resolve defects. SAAP provides a clear and intuitive method of resolution for each service layer in some embodiments.

Figure 35:
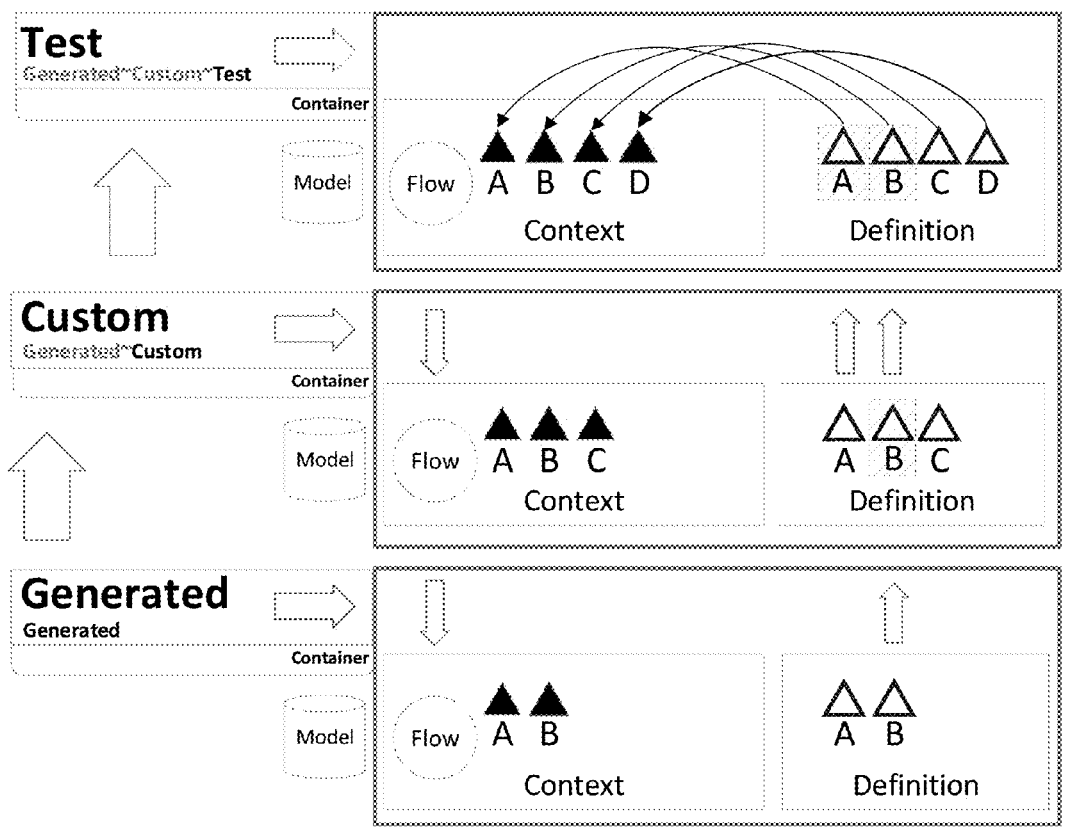
FIG. 35 illustrates an implementation where the service context is defined in the test assembly, according to an embodiment of the present invention.
Figure 36:
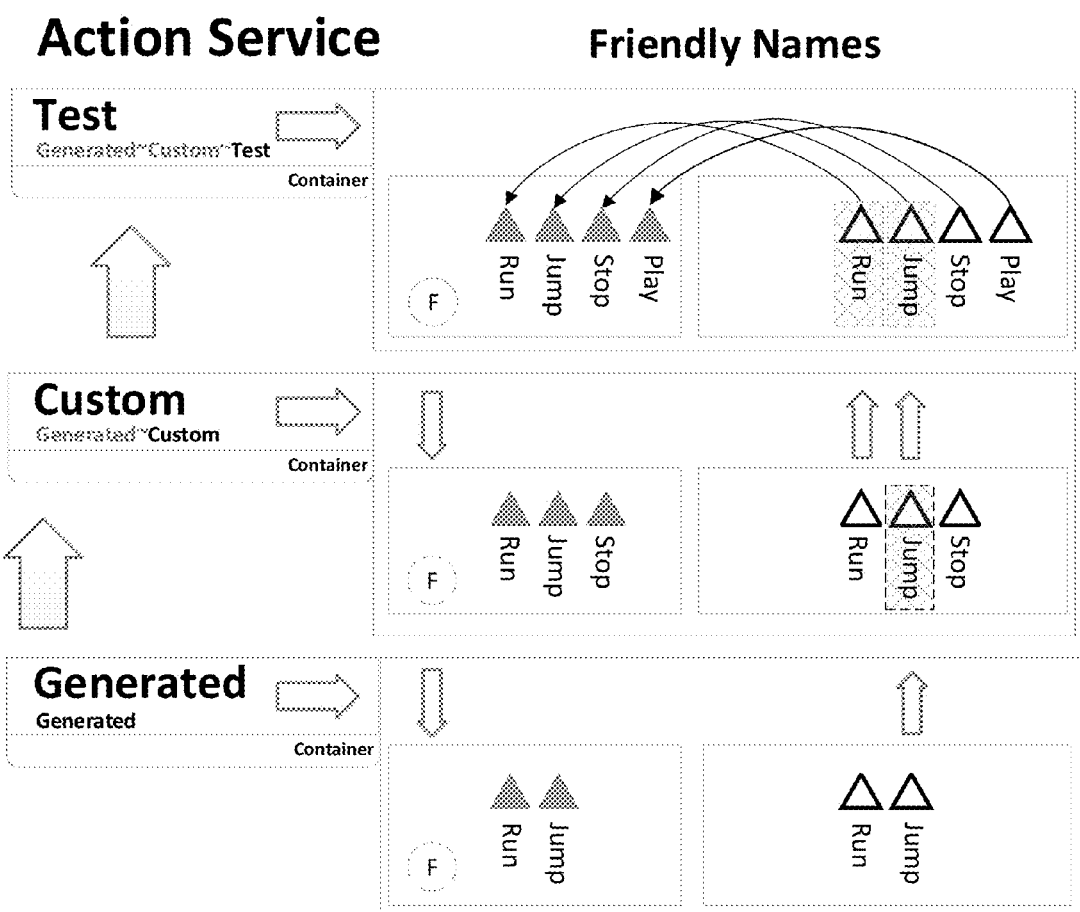
FIG. 36 illustrates an implementation of an action service, according to an embodiment of the present invention.

FIG. 35 depicts an implementation 3500 with three layers—test, custom, and generated. The behavior is affected by the point of entry, which is determined by where the flow is created. FIG. 35 depicts the service context being defined in the test assembly. This is important as depicted in this diagram, the context resolution with an entry point is at the custom layer, such as would be the case during the application's normal operation. Methods A, B, C will be available. During automated testing, the context methods will be A, B, C, D. Using the fields of A, B, C, D is by way of example only here. Generally, more reader friendly names are used (e.g., Run, Jump, Stop, and Play), as depicted in action service diagram implementation 3600 of FIG. 36. This diagram depicts different names from A, B, C, D in FIG. 35. The logic for resolving the method definitions for a given set of methods remains the same. Additionally, any number of method references and method definitions can be introduced at any given level.

If a secondary service is requested within a method definition, the flow determines what the point of origin is. This can be seen in service diagram 3700 of FIG. 37. In FIG. 37, the test layer of service A is the point of entry. A request to service B is made from the generated layer, which is at the lowest level of FIG. 37. Because the initial point of entry for the given flow object was in the test layer, service B will also be resolved as at the test layer. If, however, the method in the generated layer were to create a new flow object, service B's point of entry would be the generated layer.

The reason why the point of entry is designed this way is to provide a unified set of behavior that is not affected by which method or layer called it. Consider, for instance, an example of file access. File access generally differs in the test layer and the business layer because the test layer is written to test logic while the business layer needs to perform a business task. If the framework provides a methodology to save files, the save methodology could be called by the generated layer. When the business layer is the point of entry, it would perform normal file operations. When the test layer is the point of entry, the file activity would be simulated. This behavior would be automatically propagated no matter where the behavior is defined.

Figure 38:
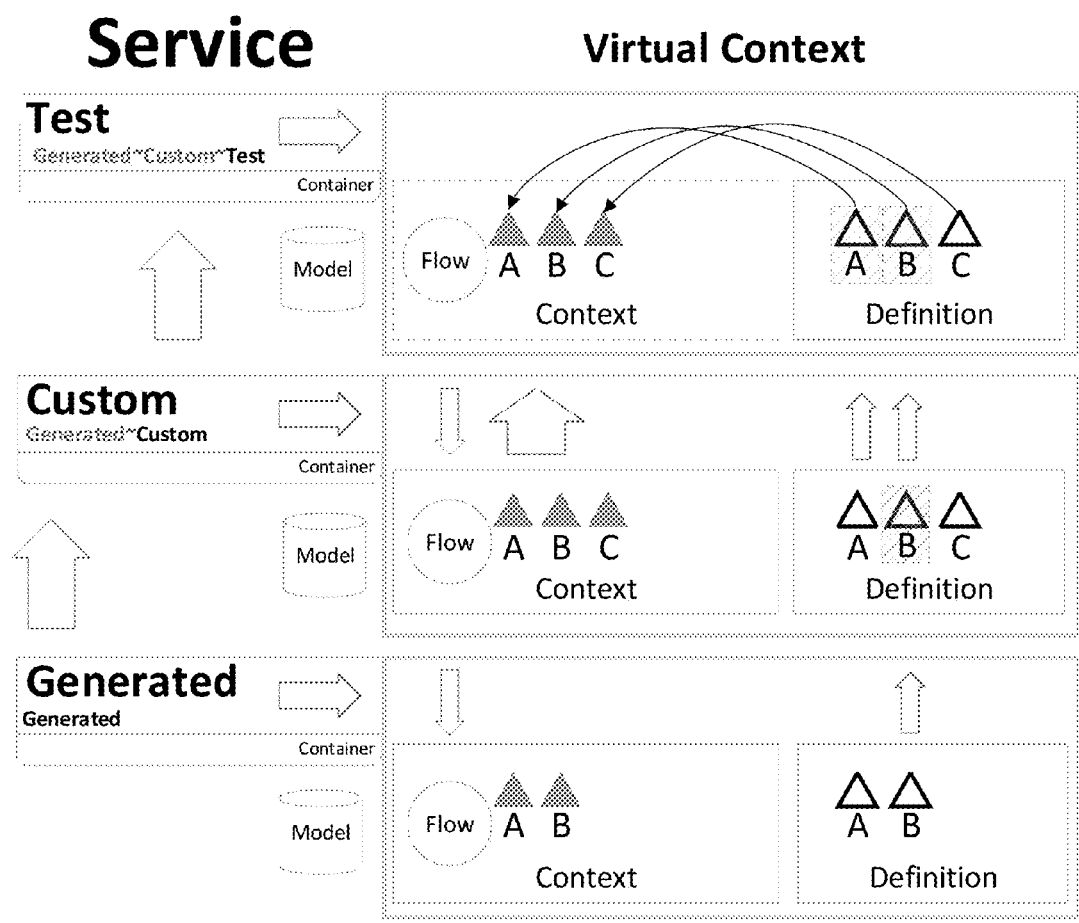
FIG. 38 illustrates virtual context, according to an embodiment of the present invention.
Figure 39:
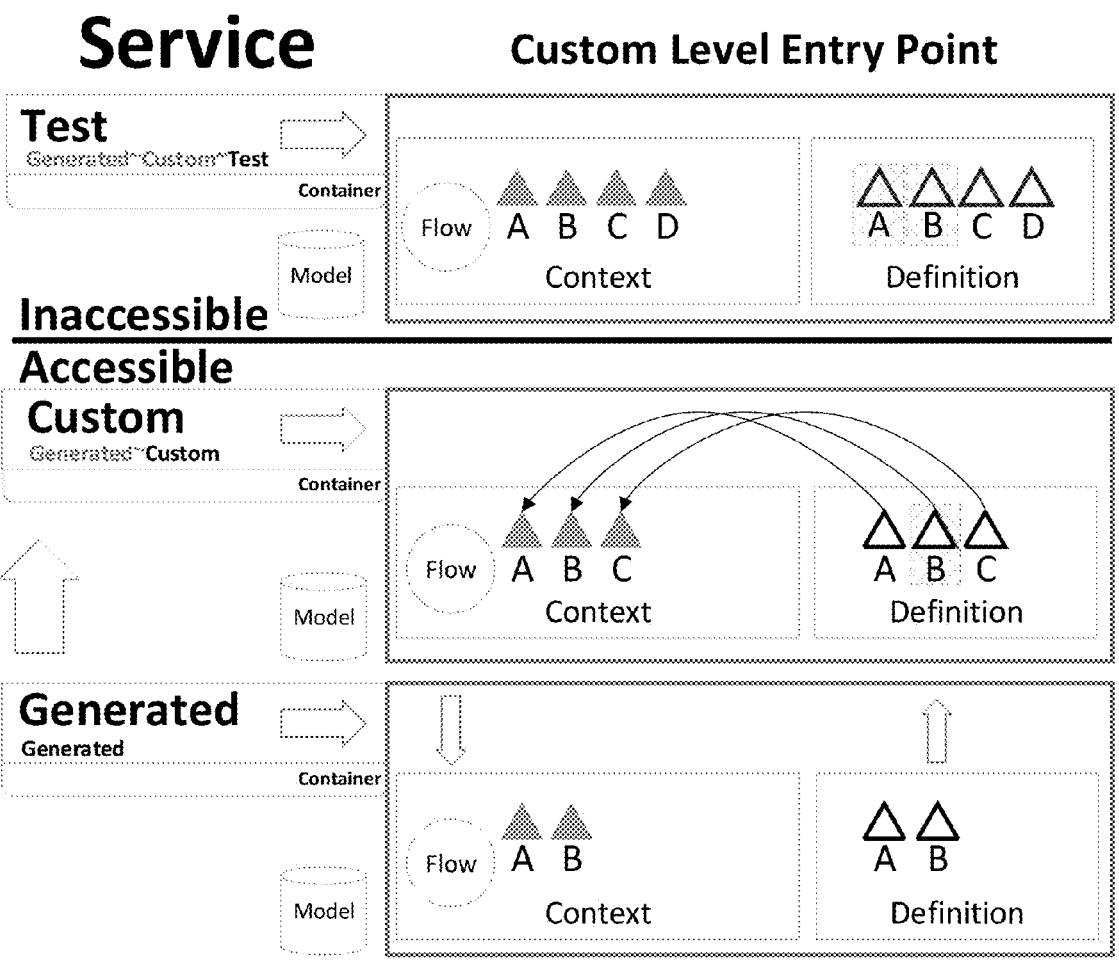
FIG. 39 illustrates an initial entry point in the custom layer, according to an embodiment of the present invention.

Overriding the service objects for a given layer is optional. As can be seen in virtual context diagram 3800 of FIG. 38, the test context object is reused from the Custom Context layer. If the initial entry point is instead in the custom layer, as shown in custom layer diagram 3900 of FIG. 39, the test layer would become inaccessible. Consequently, the test layer as defined will no longer have any effect on how the execution of any given process, as was illustrated in FIGS. 35-38.

Workflow

As discussed above, the context object type contains references to the model data and method references. By convention, the nested method calls reference the context reference as opposed to direct references. This is not out of necessity, but lends the given context increased flexibility and visibility (especially for testing). It is possible to access a method of a previous service layer. Doing so would serve to provide similar behavior to that of classic polymorphism. It is also possible for the flow object to provide the next available method dynamically in succession. This, in fact, could be done in succession until the flow reached the base of the method hierarchy. Workflow diagram 4000 of FIG. 40 shows how methods are called and able to be altered with each successive layer.

Figure 40:
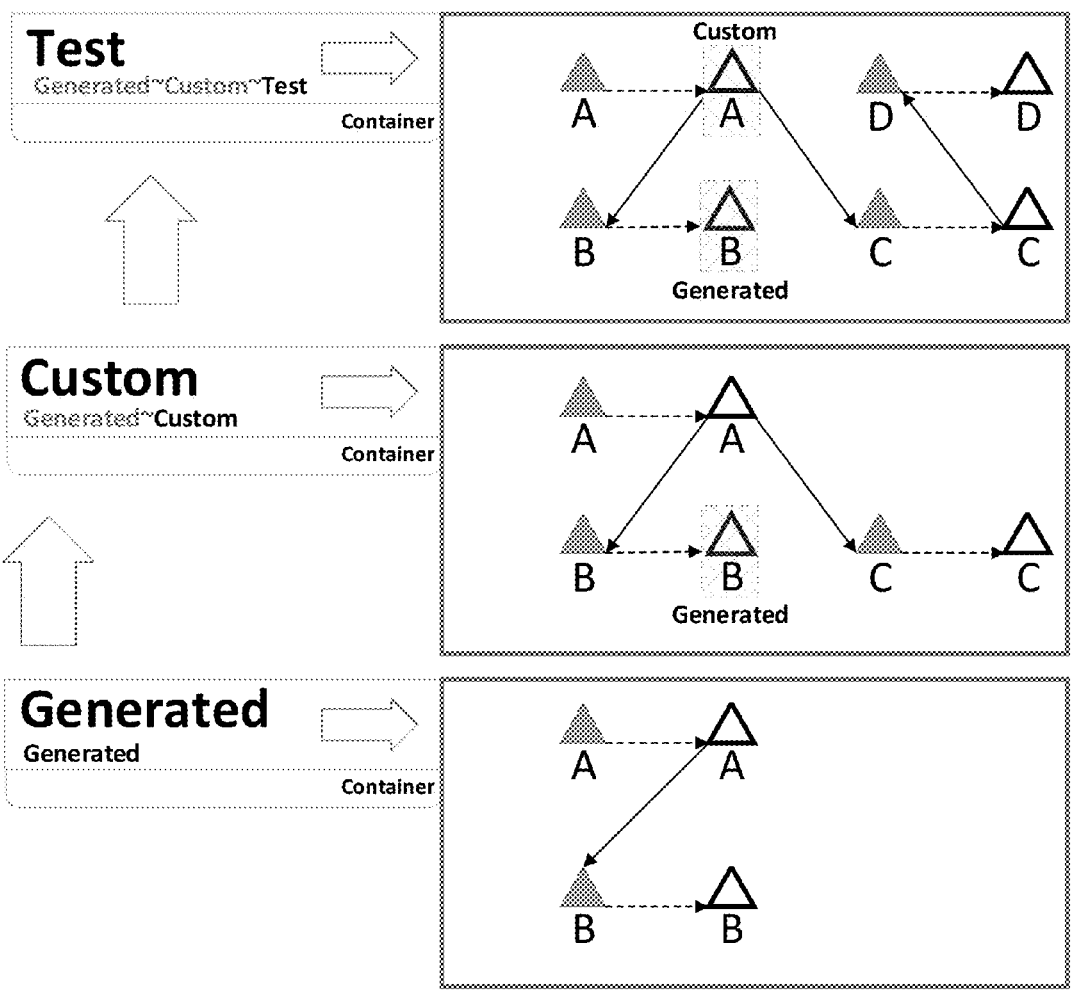
FIG. 40 is a workflow diagram illustrating how methods are called and able to be altered with each successive layer, according to an embodiment of the present invention.

It should be noted that FIG. 40 uses a pre-resolution strategy, which is effective for fast and repeatable calls. The method definitions are appropriately staggered according to the manner in which they are defined. In this case, method B stays constant, and it doesn't call any methods. However, if method B were to do so, it would call the respective method in accordance with how it was resolved, preferring the topmost layer first; just as classic polymorphism would. The behavior would be identical regardless of what kind of resolution strategy was employed. Again, resolution of any service request will be identical for a given path, regardless at what node in the path it is made. It is simple, however, to make calls that do not adhere to these guidelines. For example, a method in the custom layer may reference a method in the generated layer directly, bypassing the context object, which is similar to a base call in traditional polymorphism.

As mentioned above, a significant point of novelty of contextual polymorphism over conventional polymorphism is that the inheritance can span multiple classes. This may be analogized to game of chess. A one dimensional approach is move one piece and provide single lines of attack. However, this kind of play can be easily defeated when mastering a multi-piece coordinated attack.

Contextual polymorphism is somewhat similar conceptually to a multi-piece chess strategy. All of the core components can be overloaded in some embodiments: context, model, definitions, etc. The definition may be defined using the current model, type casting may be handled outside via the SAAP framework and may no longer be the concern of the developer.

Introducing the PRPL framework as part of the SAAP framework may provide simple and well integrated routing and workflow scenarios. The concept of the service can be loaded and modified at runtime. SAAP in conjunction with PRPL may provide an intuitive and simplified alternative to reflection.

Furthermore, SAAP may provide a simple means to blend a generated service component and a subsequent custom service component seamlessly. SAAP may be able to combine client-side requests into a single request to the server, begin a transaction, logically parse and route the request to the service methods, and commit or rollback the transactions. While this scenario may be involved, expensive, and perhaps impractical using native MVC functionality, the SAAP framework may be mostly automated and relatively simple to write and implement.

Dynamic Context

A context is not required to provide a named method reference in some embodiments. Primary methods, that have a single context parameter can be put into a dynamic method dictionary. When a method resides inside of this dictionary, methods can be called by their PRPL name.

Figure 41:
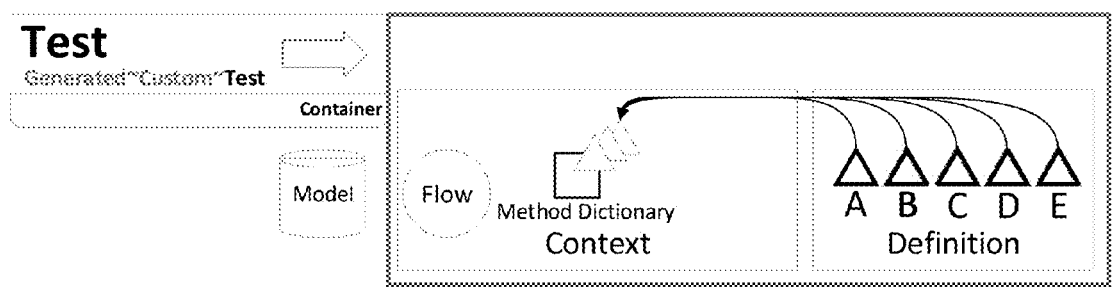
FIG. 41 illustrates dynamic context, according to an embodiment of the present invention.

In the case of an MVC web application, which service is called is based on the provided query information. Using a dynamic context, as shown in dynamic context 4100 of FIG. 41, a controller may be made into a pass through. The use of dynamic context can be seen in the client message diagram, specifically in resolve.

Figure 42:
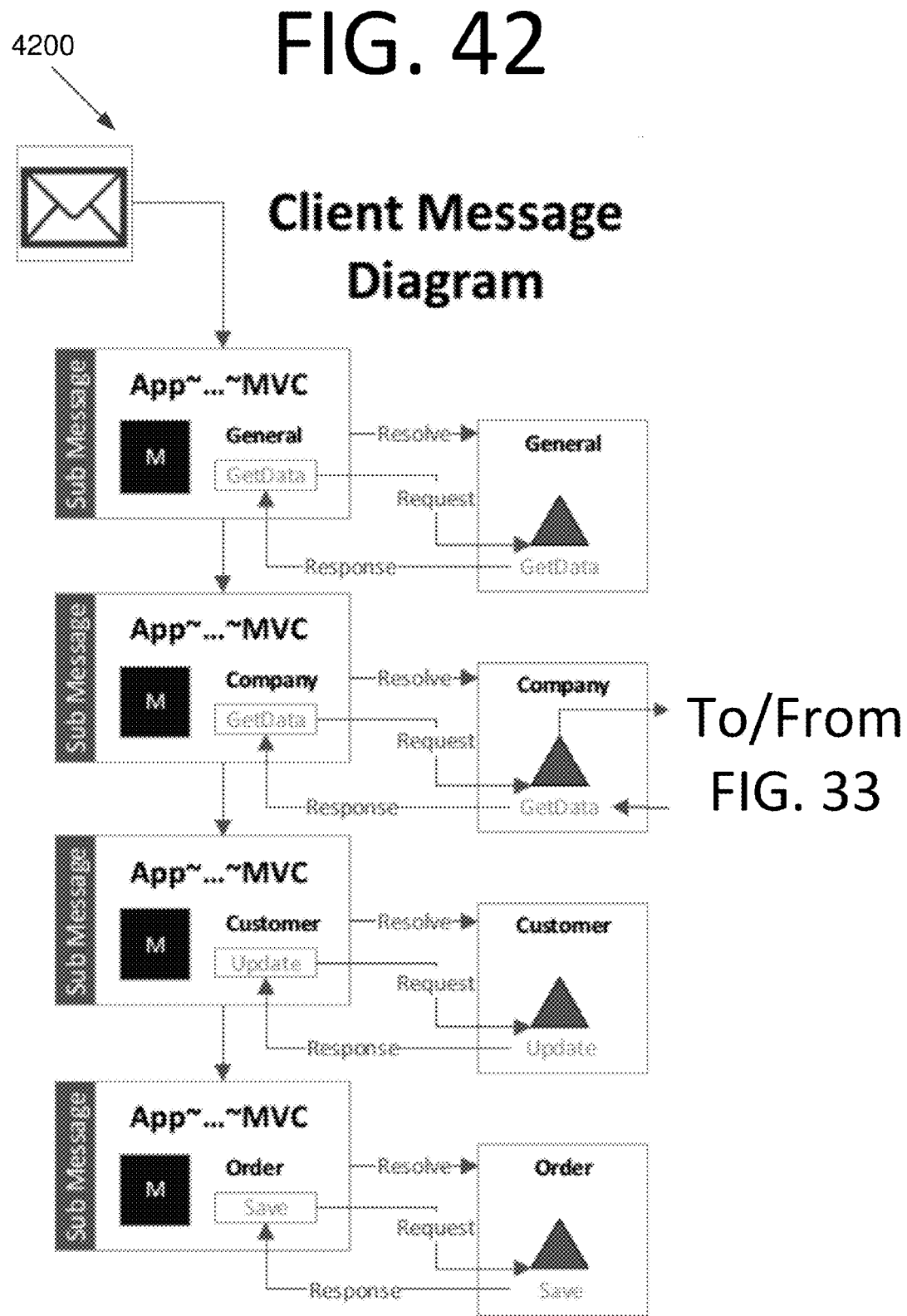
FIG. 42 is a client message diagram illustrating how multiple messages can be merged together and resolved sequentially using SAAP, according to an embodiment of the present invention.

Client message diagram 4200 of FIG. 42 shows how multiple messages can be merged together and resolved sequentially using SAAP. Moreover, services can remain distinct, having a clear and simple means to implement transactions across multiple disciplines. This may require having a begin, commit, or rollback transaction.

Services are called from common access to a web server. A general resolution service is called, which is the entry point. The model for the resolution contains the raw serialized data, meaning that it is not converted in to strongly typed object data.

Inside the resolution service, the message is broken down into sub-messages. To resolve the message, each sub-message contains a PRPL request to identify a corresponding service and method. Once the service is resolved, the sub-message data can be used to populate the appropriate model of the service context.

For the request, the resolved service method is called with the context as its sole parameter. The context is associated with its model via its request. The model of a service will generally a request object and a response object. The request data provides the necessary inputs for the service method to fulfill its operation.

The service method operation more often than not produces some sort of output. This is referred to at the response. A response can contain data from a database or some other data source (e.g., contained in call entities of objects), results from the operation performed (such as how many rows were affected), or both.

While SAAP supports other common patterns MVC routing patterns and page lifecycles in some embodiments, the SAAP client initialization pattern naturally extends the framework to the web client. See FIG. 12. The objectives of this pattern include to maximize reuse and to reduce traffic. This pattern improves the application's performance. Additionally, this pattern is easy to systematically replicate, meaning that there is a net reduction in the number of lines of code required.

In web implementations, SAAP may take advantage of how browsers naturally operate. One significant way that browsers can be optimized is through caching. When a web resource is called, it is stored on the client based on its URL. In order to save time, the client browser can store content from an identical URL (i.e., caching). If the URL is not identical, it will not be cached. The SAAP client may be designed to maximize reuse of these cached resources. The steps in FIG. 12 are sequentially described, left-to-right, top-to-bottom.

A few things not described in FIG. 12 are discussed here. For instance, the main JavaScript page is generated every time a user loads the page. It cannot be cached in some embodiments. Subsequently, for any JavaScript, file caching can be controlled at this time. Refreshing the page in the browser, which may often be done by pressing the [F5] key, should remove any stale content.

The generated JavaScript and HTML may be rendered using the Genetic Framework at runtime. It may correspond with the namespace, similar to that of the application. The URL query string is a strong determining factor if content is to be cached. Adding the version of the compiled library would remove the cache after a redeployment. Adding the current date and time would disable caching. Adding the security token would refresh the cache when the user's permissions have been changed. Security can modify the content of the markup and script, perhaps removing functions that are not permitted. The server will generally validate the permissions as well to ensure that the client hasn't been hacked.

The user info date may control the cache of client user info data. The last general data date may control the caching of general data content. The genetic encoding date, which is the last time the DNA or RNA was updated in the Genetic framework, can be used to govern the cached content.

Dynamic Operators

SAAP can be further extended using dynamic operators. A dynamic operator provides a means to sequentially and conditionally run a preset set of methods. Operators may follow the patterns depicted in dynamic operator flow patterns diagram 4300 of FIG. 43, and can be further extended to manage custom patterns. The operators can be extended to provide additional functionality, such as toggling the path of execution when the event is met or not met.

In FIG. 43, the All pattern provides the product of all nodes that meet the given criteria. It is the universal pattern from which all other patterns are derived. The All pattern may be oriented forwards or backwards, and may be configured to provide a default product.

The First Group pattern is based on the All pattern. It provides the product of all operators of a chain until an operator criterion fails to be met. It can be configured to start at the first operator criteria to be met.

The First pattern is a derivative of the First Group pattern. The only significant difference is that only one operator's product can be used. The Default fallback is the operation that executes if no operators in the normal chain met the criteria of a given request. The Default node is not required as part of a given operation chain. A given request can also be configured to ignore the operator request.

Figure 44:
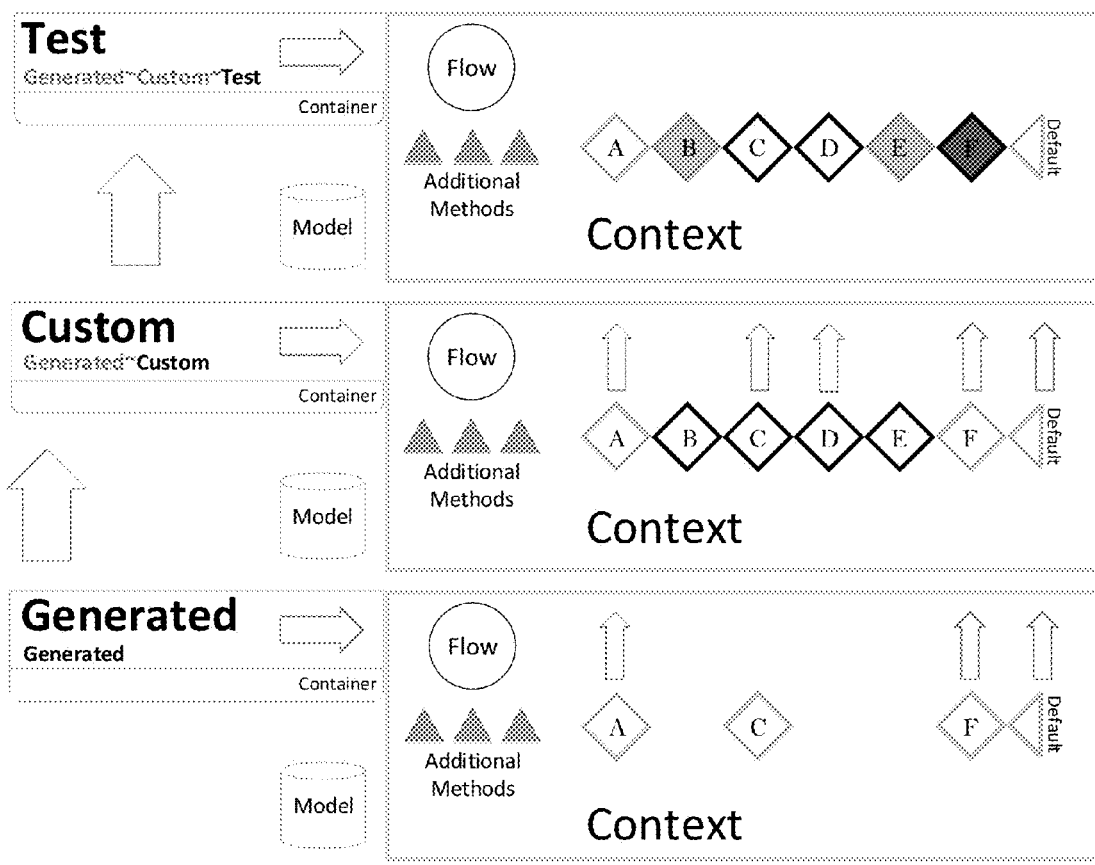
FIG. 44 illustrates dynamic operator construction, according to an embodiment of the present invention.

Dynamic operators may be constructed as shown in dynamic operator construction diagram 4400 of FIG. 44. The top layer represents what the final operating change will be, unless it is manually modified. FIG. 44 depicts how dynamic operators are constructed for a given context based on how the layering occurs. It is an extension of the core contextual polymorphism concept. Classes are associated or nested as children of a given context. The class must be constructible (not abstract) in some embodiments and of a compatible type of a chain (meet the constrains of generic parameters).

The custom context inherits from the generated context and is extended. Operators can be reused, replaced, or removed from the parent context. The test criteria might block or remove items to test how other operations in a given chain would handle an operation. The operators of A, C, F and Default are defined. The order can be defined by any orderable type (e.g., number, string, date, etc.). The operators A, F and Default are inherited. The operators B, C, D, and E are defined. The operator C overrides the Generated operators. The operators A, C, D, and Default are inherited. The operators B and E are defined. Operator F is either disabled or removed from the chain of operations.

Dynamic operators may be managed in a similar way to other structures using contextual inheritance. The definition of the dynamic operators can span multiple layers over a given service. Dynamic operators are defined in a corresponding container layer. PRPL is used to identify and override the type. Note the similarities for the path of resolution to that of other forms of contextual polymorphism. A dynamic operator is a context object type that follows the request/response pattern, as depicted in dynamic operator definition diagram 4500 of FIG. 45.

Figure 45:
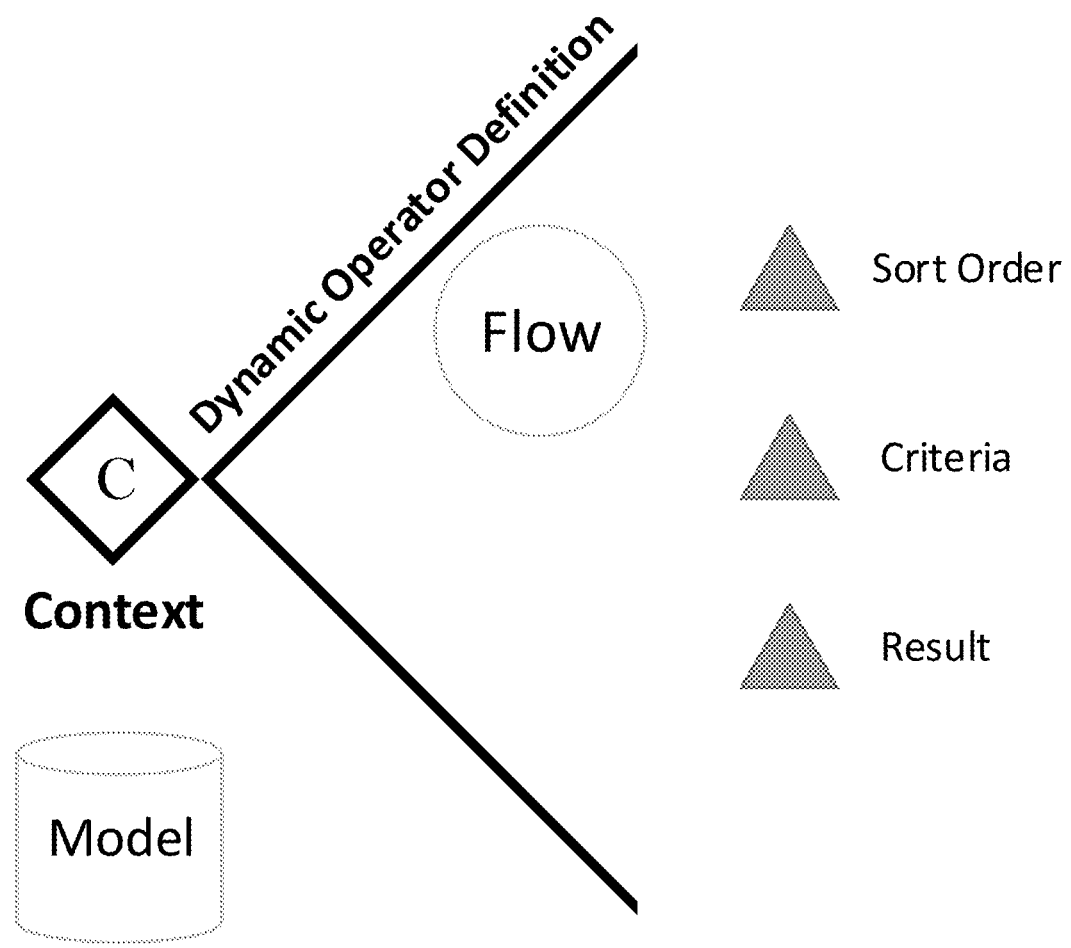
FIG. 45 illustrates dynamic operator definitions, according to an embodiment of the present invention.

In FIG. 45, the context is the container object that contains a point of reference for how components relate internally and externally. The flow object determines point of origin, determines how service resolution requests should be handled, and provides tracing and debugging information. The model is the box or container for the data that is to be operated upon. Separating the model from the functionality improves portability, flexibility, and testability.

The sort order method determines the order of the operators in a given chain. The product of the sort order must be an orderable type (e.g., numeric, strong, or date). The criteria method determines whether the criteria for a given operator have been met. If met, the operator will run the result method, which provides the product.

Execute Process

The execute process is the heart of the dynamic operator process. It is highly flexible, configurable, and extendable. Even the kernel itself can be swapped out with a streamlined or extended functionality in some embodiments.

Before the execute process can work, the list of effective operators should be added. This can be either done manually or with the get operator method. The get operator method is itself configurable. It can be altered to populate the operators list with a PRPL pattern, a simple reflective pattern, or some other custom pattern.

Figure 46:
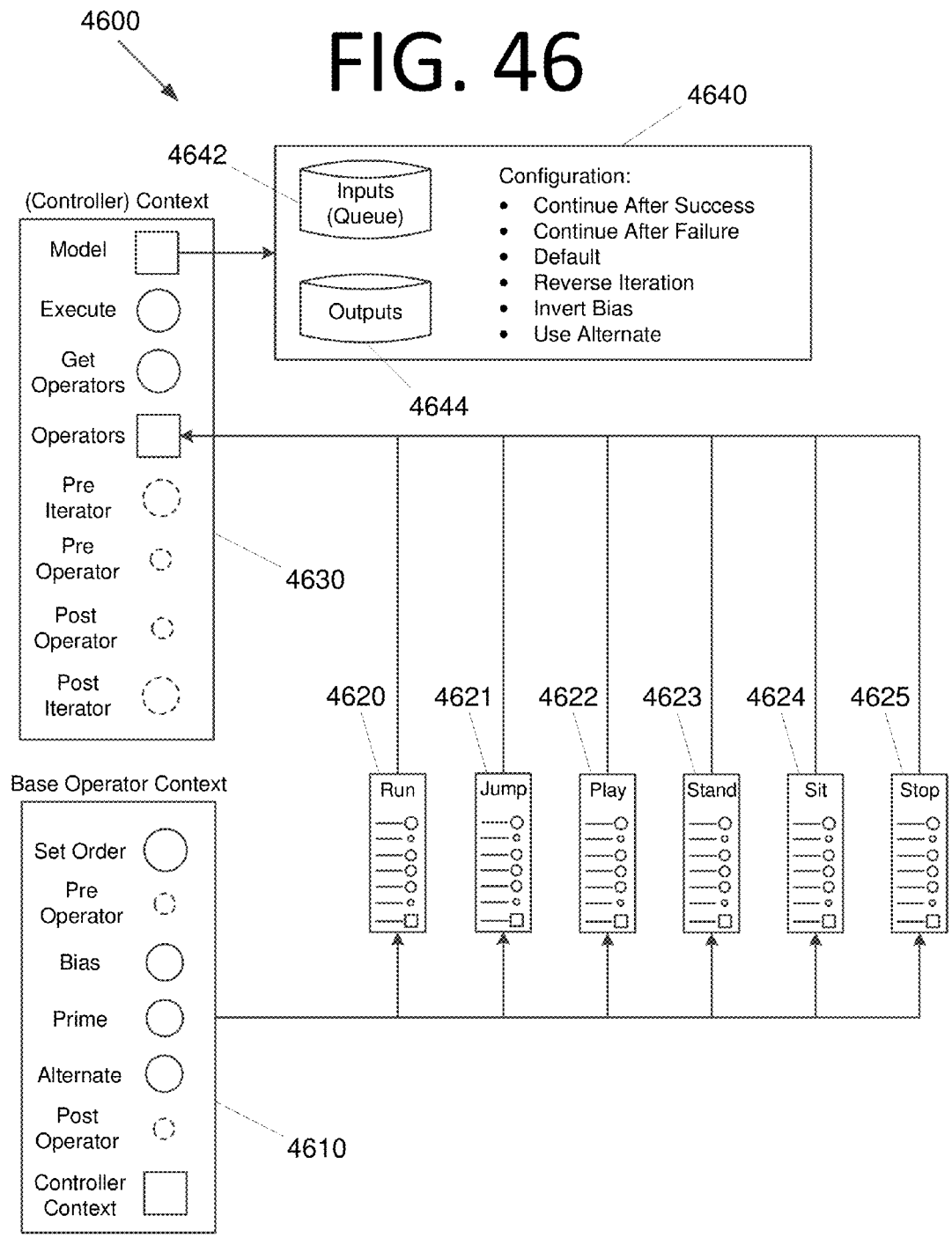
FIG. 46 illustrates detailed dynamic operator context, according to an embodiment of the present invention.

The controller context and model, base operator context, and a list of operator contexts should be defined as depicted in detailed dynamic operator context diagram 4600 of FIG. 46. Additional patterns can be constructed following similar or even differing without too much trouble. The general pattern is designed to be fluid and not rigid.

To better understand the components of FIG. 46, it is helpful to understand the definitions below.

Alternate: optionally run when bias criteria are not met.

Bias: provides criteria to determine whether the prime method should run (or alternate if the bias criteria are not met). Bias is meant to keep or invert the flow for the prime and alternate methods based on the criteria results. Typically, if the criteria result in "true," the prime method will execute. If the criteria result in "false," alternate will run. If bias is assigned false, the flow is inverted.

Controller Context: provides a reference to the controller context to provide access to its methods and model.

Execute: a method that starts the dynamic operator process.

Get Operators: a method that populates the operators list.

Model: a package that folds the data for any given context.

Operator Context: most not be abstract (i.e., must be creatable). Operator context can have additional methods, and subdividing the methods may make an operator more extendable and testable.

Operator Model: optional, but defined by the base operator context. Each operator model can be extended similar to other SAAP contexts.

Pre Iterator: optionally runs before a dynamic operator starts an iteration. The pre iterator can affect the processed data, accept the iteration, skip the iteration, or stop all iterations.

Pre Operator: optionally runs before an operator is called. The operator context method is run first when assigned. The pre operator can affect the processed data, accept the operator, skip the operator, break out of the iterator, or stop all iterations.

Post Iterator: optionally runs after a dynamic operator starts an iteration. The post iterator can affect the processed data, accept the iteration, repeat the iteration, or stop all iterations.

Post Operator: Optionally runs after an operator is called. The operator context method is run first when assigned. The post operator can affect the processed data, accept the operator, repeat the operator, break out of the iterator, or stop all iterations.

Sort Order: returns a value to sort the list of operators. If the values are equal between operators, the order does not matter.

In FIG. 46, base operator context 4610 has a set order, pre operator, bias, prime, alternate, post operator, and controller context. Each operator (i.e., run 4620, jump 4621, play 4622, stand 4623, sit 4624, and stop 4625) includes the operations of base operator context 4610. Run 4620, jump 4621, play 4622, stand 4623, sit 4624, and stop 4625 are operators of controller context 4630. Controller context 4630 has a model 4640, which includes various configurations.

Continue after Success: when false, this will end the current iteration when a bias is satisfied. When true, the iteration will continue.

Continue after Failure: when true, this will end the current iteration when a bias is not satisfied. When false, the iteration will continue.

Default: provides the result when no operators are satisfied.

Reverse Iteration: reverses the order in which operators are iterated through.

Invert Bias: flips the result of the bias (i.e., from false to true, or from true to false).

Use Alternate: indicates that the alternate method should be used as opposed to the prime method when the bias is not met.

Various events can be added. Per the above, a pre iterator happens before a given input is attempted to be resolved by any given operator. A post iterator happens after all resolution attempts have been exhausted. A pre operator occurs before a given operator attempts to process an input. This is assignable at both the controller and operator level. A post operator occurs after a given operator attempts to process an input. This is also assignable at both the controller an operator level.

Input Queue

Another requirement of some embodiments is providing one or more records from to the input queue, such as input queue 4642 of model 4640. Data can be added to input queue 4642 before and during the execute process. The execute process will continue to process until input queue 4642 is empty or an instruction is given to stop. Without data, the execute process will start and then stop. More data can be added to input queue 4642 after the execute method is finished processing. Processing can restart by calling the execute method. Restarting the execute process shouldn't require any additional setup, provided that the behavior is to remain the same. As the operators consume the data from input queue 4642, the data is paired with a corresponding output and put into an output list 4644. Output list 4644 can be used during and after the execute method is processing.

Execute Workflow

Figure 47:
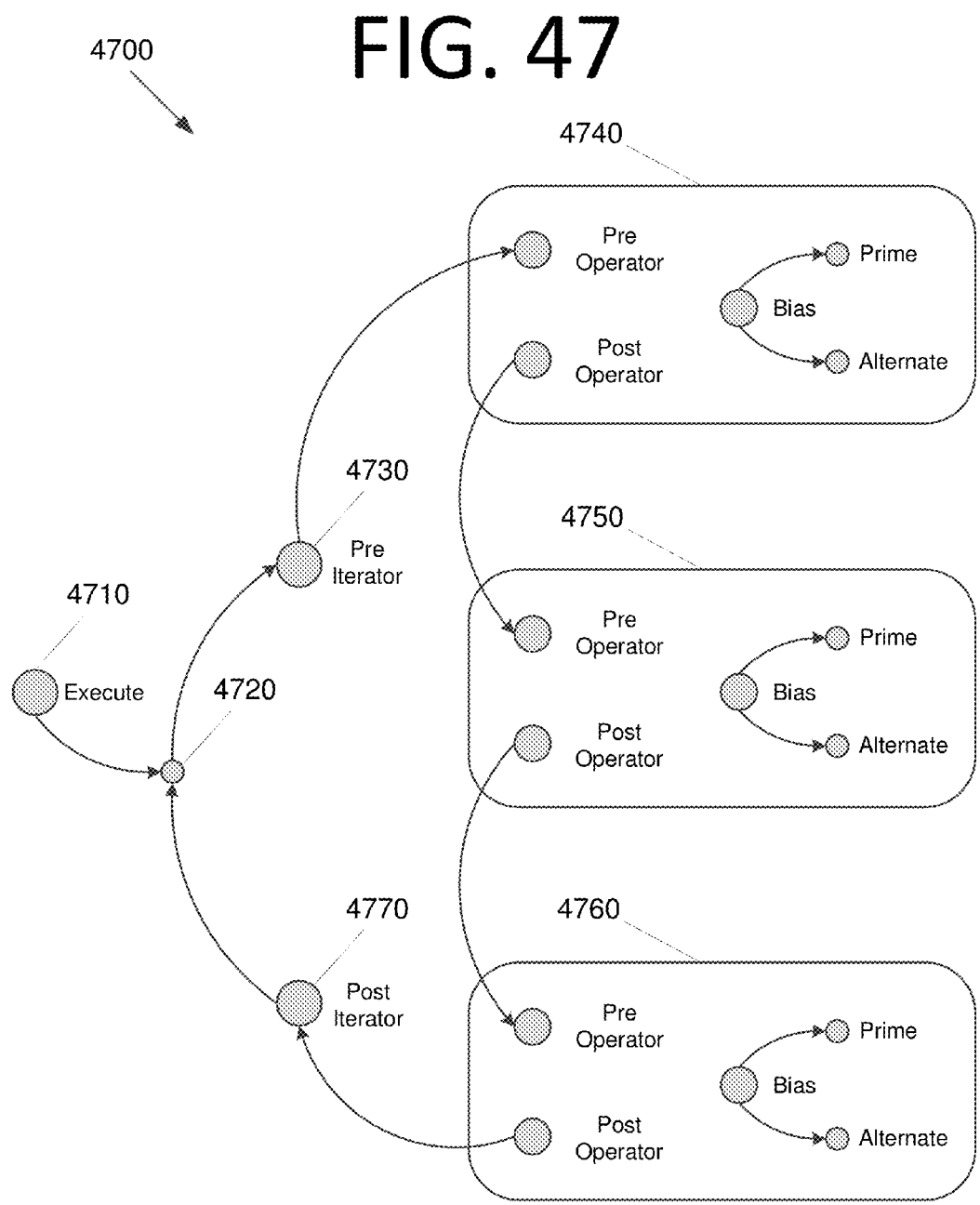
FIG. 47 is a flow diagram illustrating an execute workflow, according to an embodiment of the present invention.

FIG. 47 is a flow diagram illustrating an execute workflow 4700, according to an embodiment of the present invention. The process begins with calling the execute method at 4710. Get record from input queue 4720 is then called. When no data is present in the input queue, such as input queue 4642 of FIG. 46, execution is halted.

A pre iterator 4730 may optionally be run at the beginning of the iteration. An iteration refers to iterating through each of operators 4740, 4750, 4760 for each record of data from the input queue. Pre iterator 4730 can affect the processed data, accept the iteration, skip the iteration, or stop all iterations in some embodiments.

If the iteration is not skipped or stopped, a pre operator of operator 4740 may then optionally be run. This runs before methods of operator 4740 can execute. Per operator is optional and can be defined at the controller or operator level. The operator level method may be preferred if both are provided. The pre operator can affect the processed data, accept the operator, repeat the operator, break out of the iterator, or stop all iterations in some embodiments.

After executing methods of operator 4740, a post operator of operator 4740 may optionally be run. The post operator may be defined at the controller or operator level. If both are defined, the operator method may be preferred. The post operator can affect the processed data, accept the operator, repeat the operator, break out of the iterator, or stop all iterations in some embodiments. The iteration process then proceeds in the same manner for operator 4750 and then operator 4760.

The process finishes for operator 4760 for the current iteration, a post iterator 4770 may optionally be run. Post iterator 4770 can affect the processed data, accept the iteration, repeat the iteration, or stop all iterations in some embodiments. The process then proceeds to get record from input queue 4720, and a new iteration starts if there is data in the input queue.

The context may contain a flow object, a sort order, criteria, and a result. The model may reside outside of the context definition, but is generally defined in close proximity. The context may contain delegates that point to the defined static pointers. The flow may provide instructions for context creation and resolution. The sort order may determine the order in which a given context node for a given operation context of a dynamic operation. The criteria may determine whether a given operator should execute. In some cases, the criteria may cause the alternate method to be called. The result refers to what the outcome of prime is (or alternate, when applicable).

Comparison with Current Best Practices

SAAP takes the ideals of current best practices in the single responsibility, open-closed, Liskov substitution, interface segregation, and dependency inversion (SOLID) methodology and extends them. Extending is an organized methodology for modifying functionality.

Separation of Concerns

Current best practices define this as each class accomplishing one specific idea. However, conventionally, the structural tasks such as services, models, repositories, and interfaces are grouped as to what kind of type they are, rather than what task or purpose they fulfill. In SAAP, general types are grouped in a general space. Service types are grouped together with one of the service's respective container types.

Decoupling Data and Functions (i.e., Methods)

Current best practices direct users to separate data, service logic, and resources. Resources are data provider classes. In SAAP, data and functionality are not only separate, but also consolidated, and thus simplified. Because data is almost always packaged together, the functional behavior is more extensible. Fewer methods are required to be defined for the context, routing is simplified, and it is much easier to refactor code.

Contrary to current best practices, method definitions are static. This means that code will fail to compile if the decoupling principal is ignored. While data and functions are strongly decoupled, the context and container object types provide a clear point of reference as to how the data and functions relate. This will increase the overall maintainable of the code and simplify development.

There are no resources—only services—simplifying the architecture. The methods of resources services can be replaced with a predictable dataset, which is critical for development and testing. Furthermore, constructing code in this way lends itself to being extremely future proof. A constrained architecture provides a simple mechanism to isolate the usage of $3^{rd}$ party components. Migrating from one of these components in favor of another, perhaps due to technological advances, would mean simply replacing the current definition and testing the new behavior. Further, future proofing for more ubiquitous components may be further aided with a proper genetic implementation. Method references and their definitions are decoupled to maximize flexibility.

Substitution (Liskov Substitution Principle)

Current best practices in the SOLID methodology direct users to construct code so code parts can be substituted for other code parts. This is often done by assigning interfaces, which assures that a sort of coding contract is provided. An interface is a contract. The interface acts as a proxy that guarantees that a member or method is present.

Using interfaces means that code can be reusable in more places. To its detriment, it is common for testing to become expensive and prone to defects. For instance, when an interface containing five methods is implemented without using inheritance, all five methods have to be defined. Creation of classes and implementing methods is an extra expense. Each line of code is a liability and a chance for a bug to be introduced. A given interface may need multiple class implementations to test the various facets of the code. Furthermore, managing a well-tested application can become increasingly more expensive in that: (1) the volume of code will grow with the growth of the application; and (2) labor costs increase as it takes more time and expertise to manage the code base.

In SAAP, all functions defined in the context are replaceable. In contrast to the current best practices, working with a context is more economical by several orders of magnitude. There are a number of simple, optimal options for a variety of scenarios.

For instance, a given context can be extended or redefined in a similar manner to the custom layer. This is particularly useful in simulating operating system or resource tasks. An example of this would be simulating reading and writing files in a file structure. This would allow for testing of the system logic with fast, predictable data sets. Additionally, common redundant method assignments could be removed.

An object of a named or anonymous type could be implement provide a series of function definitions. Functions can feed into the flow item as quick step of resolution. The flow object could be configured through an except if binding was unsuccessful so as to ensure the validity of a test. A method pointer of a context type could be directly assigned inside the test method.

Interface Segmentation

Current best practices in the SOLID methodology direct users to design interfaces with a limited number of members as a mechanism for generalization and substitution. Generally, interfaces are used with service or repository object types. SAAP makes use of interfaces as well. Since the service in SAAP is an abstract concept, an interface cannot be applied here. Instead, interfaces can be applied to model and context types. Interface types are not used for substitution like in SOLID, using some sort of injection framework. Instead, interface types are used to categorize or associate a given creatable data type, perhaps between service containers or as a means of extendibility. Additionally, helper methods and shortcuts could be associated with a given interface, which is a quick way to access functionality from an outside context object.

Dependency Inversion

Current best practices of SOLID require a specific set of object relationships, which work with the interface. An injection framework will identify a given interface to inject mapped objects into method parameters. The injection frameworks are often awkward to work with. While there are similarities between the various injection frameworks, there is no real standard for implementation. Additionally, the mapping usually happens away from the code definition. This makes code harder to trace and harder to work with.

SAAP renders and manages its own dependency injection. The definition and injectable code are either in obvious succession or in close proximity. The flow object, which manages the injection, can be interrogated to understand how objects and definitions have been resolved in order to correct any issues that may have occurred. Consequently, dependency is more manageable and easier to work with.

Figure 48:
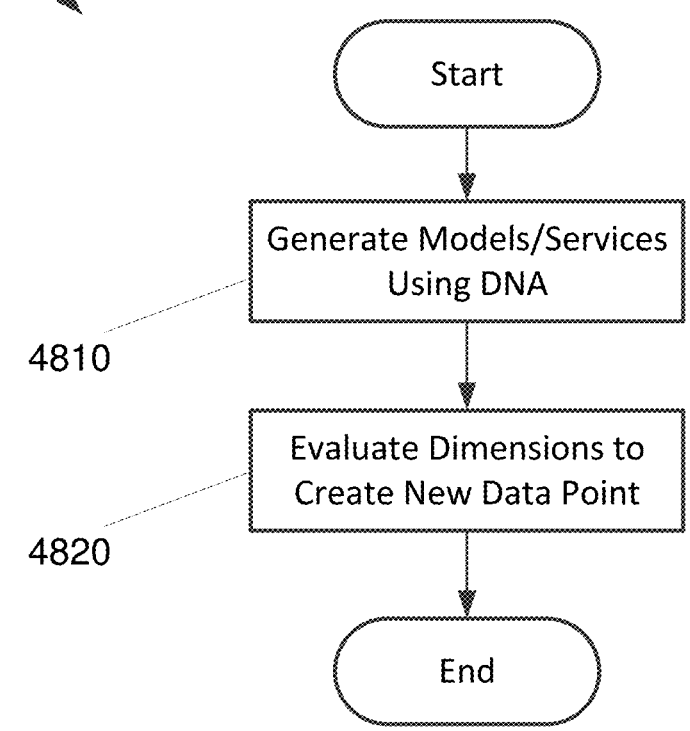
FIG. 48 is a flowchart illustrating a process for generating DNA, according to an embodiment of the present invention.

FIG. 48 is a flowchart 4800 illustrating a process for generating DNA, according to an embodiment of the present invention. The process begins with generating declarative script models with services using DNA at 4810. DNA may describe relationships between the models and services. The relationships between models and services may be defined by DNA files referencing other DNA files. The relationships between the DNA files themselves may be described using a PRPL tag.

A DNA layer file may be created for each successive layer. Each DNA layer may include a plurality of DNA files that are representative variations of a given data entity. Relationships between different entity types may be explicitly described in respective DNA files. DNA may provide instructions on how to build library references, information reflective of relevant database structures, declarative markup, and script templates. DNA may be paired up with other DNA files, templates, and operators to produce DNA files and affect an outcome of RNA. At least three dimensions for a single data point are evaluated to create a new data point at 4820. The data point may be a text node, an element node, or an attribute node in some embodiments.

Figure 49:
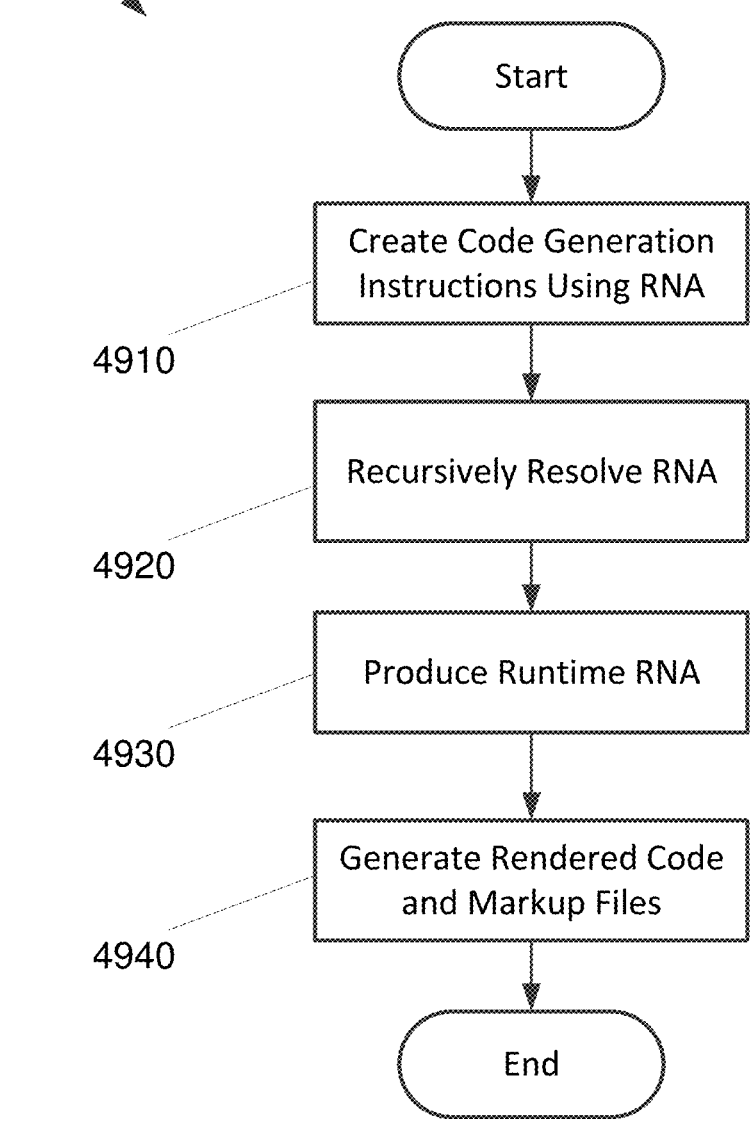
FIG. 49 is a flowchart illustrating a process for generating RNA, according to an embodiment of the present invention.

FIG. 49 is a flowchart 4900 illustrating a process for generating RNA, according to an embodiment of the present invention. The process begins with creating instructions on how corresponding target application code is to be generated using RNA at 4910. A given RNA file may categorically qualify and define how DNA base pairs are resolved in the corresponding target application code. When processing an RNA file, DNA may be related into base pairs, the RNA file may qualify which base pair can be used to generate a given code file resource, and each code file resource may represent a model, service, or visual resource. RNA may navigate through assigned DNA base pairs using iterators, operators, filters, paging, and/or sorting.

The RNA is recursively resolved using recursive descent at 4920. This may include executing a categorical pre-qualifier, a categorical post-qualifier, or both, and using recursive descent to include the categorical pre-qualifier, the categorical post-qualifier, or both, in a given RNA file. A categorical pre-qualifier may be executed before resolution and a categorical post-qualifier is executed after resolution. A given categorical qualifier refers to an attribute indicating whether certain fields are present. Runtime RNA code is produced at 4930. The runtime RNA code is organized for the target application to interpret ant runtime. Rendered code and markup files are generated for a corresponding target application as part of a Genetic layer to be executed by a computing system associated with the corresponding target application using the RNA to create precompiled RNA at 4940.

Figure 50:
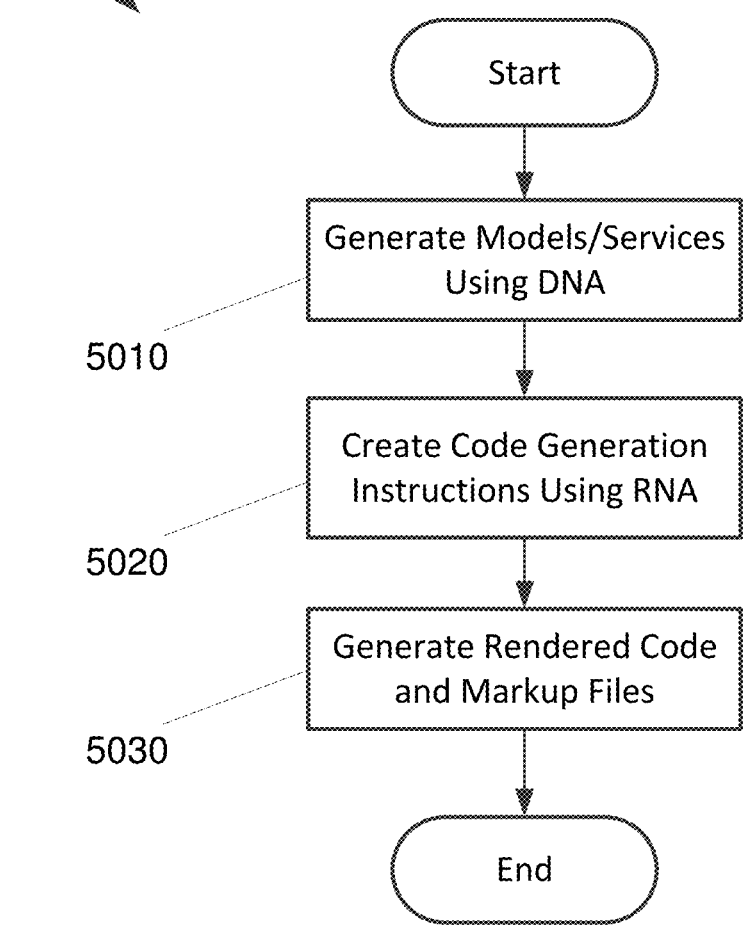
FIG. 50 is a flowchart illustrating a process for generating DNA and RNA, according to an embodiment of the present invention.

FIG. 50 is a flowchart 5000 illustrating a process for generating DNA and RNA, according to an embodiment of the present invention. The process begins with generating declarative script models with services using DNA, which provides a structure to identify and modify data schemas, at 5010. Instructions on how corresponding target application code is to be generated are created using RNA at 5020. A given RNA file categorically qualifies and defines how DNA base pairs are resolved in the corresponding target application code. Rendered code and markup files are generated for a corresponding target application as part of a Genetic layer to be executed by a computing system associated with the corresponding target application using the RNA to create precompiled RNA at 5030.

Figure 51:
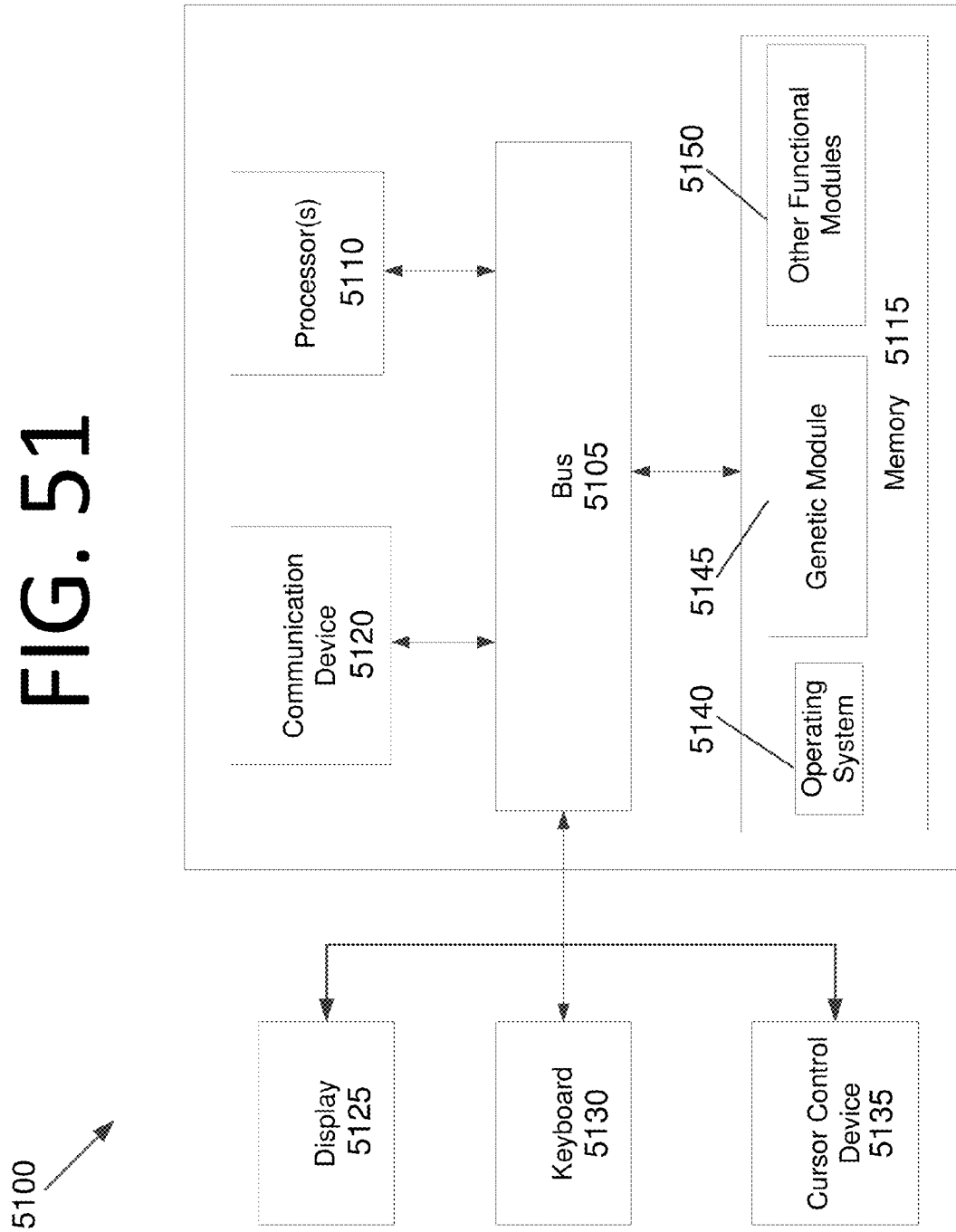
FIG. 51 is a block diagram illustrating a computing system configured to carry out various Genetic Framework, PRPL, and SAAP operations, according to an embodiment of the present invention.

FIG. 51 is a block diagram illustrating a computing system 5100 configured to carry out the various Genetic Framework, PRPL, and SAAP operations discussed herein, according to an embodiment of the present invention. Computing system 5100 includes a bus 5105 or other communication mechanism for communicating information, and processor(s) 5110 coupled to bus 5105 for processing information. Processor(s) 5110 may be any type of general or specific purpose processor, including a central processing unit ("CPU") or application specific integrated circuit ("ASIC"). Processor(s) 5110 may also have multiple processing cores, and at least some of the cores may be configured to perform specific functions. Multi-parallel processing may be used in some embodiments. Computing system 5100 further includes a memory 5115 for storing information and instructions to be executed by processor(s) 5110. Memory 5115 can be comprised of any combination of random access memory (RAM), read only memory (ROM), flash memory, cache, static storage such as a magnetic or optical disk, or any other types of non-transitory computer-readable media or combinations thereof. Additionally, computing system 5100 includes a communication device 5120, such as a transceiver and antenna, to wirelessly provide access to a communications network.

Non-transitory computer-readable media may be any available media that can be accessed by processor(s) 5110 and may include volatile media, non-volatile media, removable media, and/or non-removable media.

Processor(s) 5110 are further coupled via bus 5105 to a display 5125, such as a Liquid Crystal Display (LCD), for displaying information to a user. A keyboard 5130 and a cursor control device 5135, such as a computer mouse, are further coupled to bus 5105 to enable a user to interface with computing system. However, in certain embodiments such as those for mobile computing implementations, a physical keyboard and mouse may not be present, and the user may interact with the device solely through display 5125 and/or a touchpad (not shown). Any type and combination of input devices may be used as a matter of design choice.

Memory 5115 stores software modules that provide functionality when executed by processor(s) 5110. The modules include an operating system 5140 for computing system 5100. The modules further include a genetic module 5145 that is configured to the various genetic framework, PRPL, and SAAP operations discussed herein derivatives thereof. For instance, genetic module 5145 may perform various DNA, RNA, PRPL, and/or SAAP functionality. Computing system 5100 may include one or more additional functional modules 5150 that include additional functionality.

One skilled in the art will appreciate that a "system" could be embodied as an embedded computing system, a personal computer, a server, a console, a personal digital assistant (PDA), a cell phone, a tablet computing device, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration ("VLSI") circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIGS. 48-50 may be performed by a computer program, encoding instructions for the nonlinear adaptive processor to perform at least the processes described in FIGS. 48-50, in accordance with embodiments of the present invention. The computer program may be embodied on a non-transitory computer-readable medium. The computer-readable medium may be, but is not limited to, a hard disk drive, a flash device, a random access memory, a tape, or any other such medium used to store data. The computer program may include encoded instructions for controlling the nonlinear adaptive processor to implement the processes described in FIGS. 48-50, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method, comprising:
generating, by a computing system, declarative script models with services using a Data Notation Architecture (DNA), wherein the DNA provides a structure to identify and modify data schemas;
creating instructions on how corresponding target application code is to be generated, by the computing system, using a Resolution Notation Architecture (RNA), wherein a given RNA file categorically qualifies and defines how DNA base pairs are resolved in the corresponding target application code; and
generating rendered code and markup files for a corresponding target application as a part of a Genetic layer to be executed by a computing system associated with the corresponding target application using the RNA to create precompiled RNA.

2. The computer-implemented method of claim 1, further comprising:
producing runtime RNA code, by the computing system, wherein
the runtime RNA code is organized for the corresponding target application to interpret at runtime.

3. The computer-implemented method of claim 1, wherein
a client request indicates what a targeted model/service is, and
the DNA describes relationships between the models and services.

4. The computer-implemented method of claim 3, wherein the relationships between models and services are defined by DNA files referencing other DNA files.

5. The computer-implemented method of claim 4, wherein the relationships between the DNA files are described using a Polymorphic Relational Path Language (PRPL) tag.

6. The computer-implemented method of claim 1, wherein
a DNA layer file is created for each successive layer, and
each DNA layer comprises a plurality of DNA files that are representative variations of a given data entity.

7. The computer-implemented method of claim 6, wherein relationships between different entity types are explicitly described in respective DNA files.

8. The computer-implemented method of claim 1, wherein
when processing an RNA file, DNA files are related through the base pairs,
the RNA file qualifies which base pair can be used to generate a given code file resource, and
each code file resource represents a model, service, or visual resource.

9. The computer-implemented method of claim 1, wherein the DNA provides instructions on how to build library references, information reflective of relevant database structures, declarative markup, and script templates.

10. The computer-implemented method of claim 1, further comprising:
resolving the RNA recursively, by the computing system; and
assigning the resolved RNA, by the computing system, to a code object type comprising an open property, a closed property, and a children object.

11. The computer-implemented method of claim 10, wherein
the code object creates a tree structure, the tree structure fragmented by modules that are code files, and
the modules comprise root code and information needed to save their respective code files to a location.

12. The computer-implemented method of claim 10, wherein the resolving of the DNA by the RNA comprises using recursive descent.

13. The computer-implemented method of claim 1, wherein
the DNA is paired up with other DNA files, templates, and operators to produce DNA files and affect an outcome of the RNA.

14. The computer-implemented method of claim 1, wherein the RNA navigates through assigned DNA base pairs using iterators, operators, filters, paging, and/or sorting.

15. The computer-implemented method of claim 1, wherein resolving a given command results in addition of further commands.

16. The computer-implemented method of claim 1, further comprising:
using a plurality of DNA templates, by the computing system, to qualify, split, multiply, and/or extend an initial data layer.

17. The computer-implemented method of claim 1, wherein components of any level can be overridden and extended.

18. The computer-implemented method of claim 1, further comprising:
evaluating at least three dimensions for a single data point, by the computing system, to create a new data point, wherein
the data point is a text node, an element node, or an attribute node.

19. The computer-implemented method of claim 1, further comprising:
executing a categorical pre-qualifier, a categorical post-qualifier, or both, by the computing system; and
using recursive descent, by the computing system, to include the categorical pre-qualifier, the categorical post-qualifier, or both, in a given RNA file, wherein
a categorical pre-qualifier is executed before resolution and a categorical post-qualifier is executed after resolution, and
a given categorical qualifier refers to an attribute indicating whether certain fields are present.

20. A computer program embodied on a non-transitory computer-readable medium, the program configured to cause at least one processor to:
create instructions on how corresponding target application code is to be generated using a Resolution Notation Architecture (RNA), wherein a given RNA file categorically qualifies and defines how Data Notation Architecture (DNA) base pairs are resolved in the corresponding target application code;
recursively resolve the RNA using recursive descent; and
generate rendered code and markup files for a corresponding target application as a part of a Genetic layer to be executed by a computing system associated with the corresponding target application using the RNA to create precompiled RNA.

21. The computer program of claim 20, wherein the program is further configured to cause the at least one processor to:
produce runtime RNA code, wherein
the runtime RNA code is organized for the corresponding target application to interpret at runtime.

22. The computer program of claim 20, wherein
when processing an RNA file, the DNA is related into base pairs,
the RNA file qualifies which base pair can be used to generate a given code file resource, and
each code file resource represents a model, service, or visual resource.

23. The computer program of claim 20, wherein the RNA navigates through assigned DNA base pairs using iterators, operators, filters, paging, and/or sorting.

24. The computer program of claim 20, the program further configured to cause the at least one processor to:
evaluate at least three dimensions for a single data point to create a new data point, wherein
the data point is a text node, an element node, or an attribute node.

25. The computer program of claim 20, wherein the program is further configured to cause the at least one processor to:

execute a categorical pre-qualifier, a categorical post-qualifier, or both; and use recursive descent to include the categorical pre-qualifier, the categorical post-qualifier, or both, in a given RNA file, wherein a categorical pre-qualifier is executed before resolution and a categorical post-qualifier is executed after resolution, and a given categorical qualifier refers to an attribute indicating whether certain fields are present.

26. A computer-implemented method, comprising:

generating, by a computing system, declarative script models with services using a Data Notation Architecture (DNA), wherein the DNA provides a structure to identify and modify data schemas; and using a plurality of DNA templates, by the computing system, to qualify, split, multiply, and/or extend an initial data layer.

27. The computer-implemented method of claim 26, wherein the DNA describes relationships between the models and services.

28. The computer-implemented method of claim 27, wherein the relationships between models and services are defined by DNA files referencing other DNA files.

29. The computer-implemented method of claim 28, wherein the relationships between the DNA files are described using a Polymorphic Relational Path Language (PRPL) tag.

30. The computer-implemented method of claim 26, wherein a DNA layer file is created for each successive layer, and each DNA layer comprises a plurality of DNA files that are representative variations of a given data entity.

31. The computer-implemented method of claim 30, wherein relationships between different entity types are explicitly described in respective DNA files.

32. The computer-implemented method of claim 26, wherein the DNA provides instructions on how to build library references, information reflective of relevant database structures, declarative markup, and script templates.

33. The computer-implemented method of claim 26, wherein the DNA is paired up with other DNA files, templates, and operators to produce DNA files and affect an outcome of a Resolution Notation Architecture (RNA).

34. The computer-implemented method of claim 26, further comprising:

evaluating at least three dimensions for a single data point, by the computing system, to create a new data point, wherein the data point is a text node, an element node, or an attribute node.

* * * * *